(12) United States Patent
Shelton, IV et al.

(10) Patent No.: US 12,213,675 B2
(45) Date of Patent: Feb. 4, 2025

(54) IMPLANTABLE SPHINCTER ASSISTANCE DEVICE WITH HOLDING, ALIGNING OR CLAMPING FEATURES INTEGRATED INTO HOUSING

(71) Applicant: Cilag GmbH International, Zug (CH)

(72) Inventors: Frederick E. Shelton, IV, Hillsboro, OH (US); Kevin M. Fiebig, Cincinnati, OH (US); Glenn W. Ellison, Maineville, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 118 days.

(21) Appl. No.: 17/552,477

(22) Filed: Dec. 16, 2021

(65) Prior Publication Data
US 2023/0190290 A1 Jun. 22, 2023

(51) Int. Cl.
*A61B 17/12* (2006.01)
*A61B 17/00* (2006.01)
*A61F 5/00* (2006.01)

(52) U.S. Cl.
CPC .. *A61B 17/12099* (2013.01); *A61B 17/12013* (2013.01); *A61B 17/1204* (2013.01);
(Continued)

(58) Field of Classification Search
CPC .......... A61B 17/1114; A61B 17/12163; A61B 17/12; A61B 17/12009; A61B 17/12013;
(Continued)

(56) References Cited

U.S. PATENT DOCUMENTS 6,100,618 A * 8/2000 Schoeb ................... F04D 5/001
                                                               310/90
7,175,589 B2 2/2007 Deem et al.
(Continued)

FOREIGN PATENT DOCUMENTS

DE 3011742 A1 10/1981
EP 2182885 B1 3/2015

OTHER PUBLICATIONS

U.S. Appl. No. 17/552,469.
(Continued)

*Primary Examiner* — Brooke LaBranche
*Assistant Examiner* — Mitchell Brian Hoag
(74) *Attorney, Agent, or Firm* — FROST BROWN TODD LLP

(57) ABSTRACT

An apparatus includes a plurality of beads a linking assembly joining the beads together. The beads and the linking assembly are arranged in an annular arrangement and sized to form a loop around an anatomical structure in a patient. The loop may move between a contracted and expanded configuration. The loop is magnetically biased toward the contracted configuration by a magnetic bias of the beads. Each bead includes a housing having a first piece and a second piece that together define a magnetic chamber. A magnetic is within the magnetic chamber. A weld joins the first piece and the second piece while hermetically sealing the magnet chamber. The first piece of the housing includes a mounting feature integrated with a surface of the first piece. The mounting feature mates with a fixture to constrain the first piece of the housing as the weld is formed.

17 Claims, 42 Drawing Sheets

(52) U.S. Cl.
CPC .... *A61B 17/1215* (2013.01); *A61B 17/12163* (2013.01); *A61B 2017/00827* (2013.01); *A61B 2017/00876* (2013.01); *A61F 5/0063* (2013.01); *A61F 5/0079* (2013.01)

(58) Field of Classification Search
CPC .............. A61B 17/22; A61B 17/12036; A61B 17/1204; A61B 2017/00827; A61B 2017/12004; A61F 5/005; A61F 5/0053; A61F 5/0056; A61F 5/0059; A61F 5/0063; A61F 5/0066; A61F 5/0076; A61F 5/0079; A61F 5/0003; A61F 6/20; A61F 5/003; A61F 5/0006; A61F 5/0009; A61F 5/0013; A61F 2005/0016; A61F 2005/002; A61F 2005/0023; A61F 5/0033; A61F 5/0036; A61F 5/004; A61F 5/0043; A61F 5/0046; A61F 5/0069; A61F 5/0073; A61F 5/0083; A61F 5/0089; A61F 6/204; A61F 2/0031; A61F 2/005; A61F 5/0086; A61F 6/202; A61F 6/206

See application file for complete search history.

(56) References Cited

U.S. PATENT DOCUMENTS

| | | | |
|---|---|---|---|
| 7,695,427 B2 | 4/2010 | Kugler et al. | |
| 8,070,670 B2 | 12/2011 | Deem et al. | |
| 8,734,475 B2 | 5/2014 | Ekvall et al. | |
| 8,870,898 B2 | 10/2014 | Beisel et al. | |
| 10,245,133 B2 | 4/2019 | Alharmi et al. | |
| 10,405,865 B2 | 9/2019 | Shelton, IV et al. | |
| 10,517,600 B2 | 12/2019 | Beisel et al. | |
| 10,543,074 B2 | 1/2020 | Frigstad et al. | |
| 10,716,570 B2 | 7/2020 | Shelton, IV et al. | |
| 10,813,737 B2 | 10/2020 | Auld et al. | |
| 10,828,064 B2 | 11/2020 | Flakne et al. | |
| 10,842,496 B2 | 11/2020 | Shelton, IV et al. | |
| 10,945,738 B2 | 3/2021 | Auld et al. | |
| 11,071,619 B2 | 7/2021 | Shelton, IV et al. | |
| 11,076,856 B2 | 8/2021 | Kopelman | |
| 11,207,173 B2 | 12/2021 | Popescu | |
| 11,298,136 B2 | 4/2022 | Shelton, IV et al. | |
| 11,350,946 B2 | 6/2022 | Dobashi et al. | |
| 11,399,928 B2 | 8/2022 | Shelton, IV et al. | |
| 11,478,347 B2 | 10/2022 | Fiebig et al. | |
| 2001/0011543 A1* | 8/2001 | Forsell | A61F 5/0053 604/909 |
| 2005/0197715 A1 | 9/2005 | Kugler et al. | |
| 2009/0222028 A1* | 9/2009 | Dlugos, Jr. | A61F 5/0059 606/151 |
| 2011/0098731 A1* | 4/2011 | Whitbrook | A61F 2/0018 606/151 |
| 2011/0270016 A1* | 11/2011 | Snow | A61F 5/0033 600/37 |
| 2011/0306824 A1* | 12/2011 | Perron | A61F 5/0056 600/37 |
| 2012/0063942 A1* | 3/2012 | LaRose | A61M 60/824 418/152 |
| 2013/0053874 A1* | 2/2013 | Ekvall | A61B 17/12013 606/157 |
| 2013/0331641 A1* | 12/2013 | Huang | A61F 5/0056 600/37 |
| 2014/0088342 A1 | 3/2014 | Djurovic | |
| 2015/0164508 A1* | 6/2015 | Hernandez | A61B 17/11 606/153 |
| 2015/0374906 A1* | 12/2015 | Forsell | A61M 27/002 604/151 |
| 2017/0112650 A1 | 4/2017 | Hingston et al. | |
| 2018/0325643 A1* | 11/2018 | Kappus | A61F 2/0004 |
| 2019/0117230 A1* | 4/2019 | Hays | A61M 25/0147 |
| 2019/0274687 A1 | 9/2019 | Wang et al. | |
| 2019/0274689 A1* | 9/2019 | Auld | A61B 17/12013 |
| 2020/0078158 A1* | 3/2020 | Popescu | A61F 5/0059 |
| 2020/0113720 A1* | 4/2020 | Jacobs | A61F 2/0063 |
| 2020/0188079 A1* | 6/2020 | Fiebig | A61B 5/4233 |
| 2020/0188081 A1* | 6/2020 | Shelton, IV | A61F 2/04 |
| 2020/0197015 A1* | 6/2020 | Shelton, IV | A61B 17/12013 |
| 2020/0197154 A1* | 6/2020 | Shelton, IV | A61B 17/12099 |
| 2021/0330443 A1* | 10/2021 | Berg | A61B 17/12013 |
| 2022/0087678 A1* | 3/2022 | Gagner | A61B 17/1114 |
| 2022/0346794 A1* | 11/2022 | Gagner | A61B 17/1114 |
| 2023/0062862 A1* | 3/2023 | Forsell | A61N 1/0509 |
| 2023/0190275 A1 | 6/2023 | Shelton, IV et al. | |
| 2023/0190276 A1 | 6/2023 | Shelton, IV et al. | |
| 2023/0190281 A1 | 6/2023 | Shelton, IV et al. | |
| 2023/0190282 A1 | 6/2023 | Shelton, IV et al. | |
| 2023/0190296 A1 | 6/2023 | Shelton, IV et al. | |
| 2023/0190299 A1 | 6/2023 | Shelton, IV et al. | |
| 2023/0190443 A1 | 6/2023 | Shelton, IV et al. | |

OTHER PUBLICATIONS

U.S. Appl. No. 17/552,474.
U.S. Appl. No. 17/552,481.
U.S. Appl. No. 17/552,483.
U.S. Appl. No. 17/552,485.
U.S. Appl. No. 17/552,488.
U.S. Appl. No. 17/552,494.
U.S. Appl. No. 17/552,780.
U.S. Appl. No. 17/552,793.
U.S. Appl. No. 17/552,800.
U.S. Appl. No. 17/552,810.
U.S. Appl. No. 17/552,796.
U.S. Appl. No. 17/552,502.
U.S. Appl. No. 17/552,503.
U.S. Appl. No. 17/552,506.
U.S. Appl. No. 17/552,508.
U.S. Appl. No. 17/552,510.
U.S. Appl. No. 17/552,514.
U.S. Appl. No. 17/552,520.
U.S. Appl. No. 17/552,522.

* cited by examiner

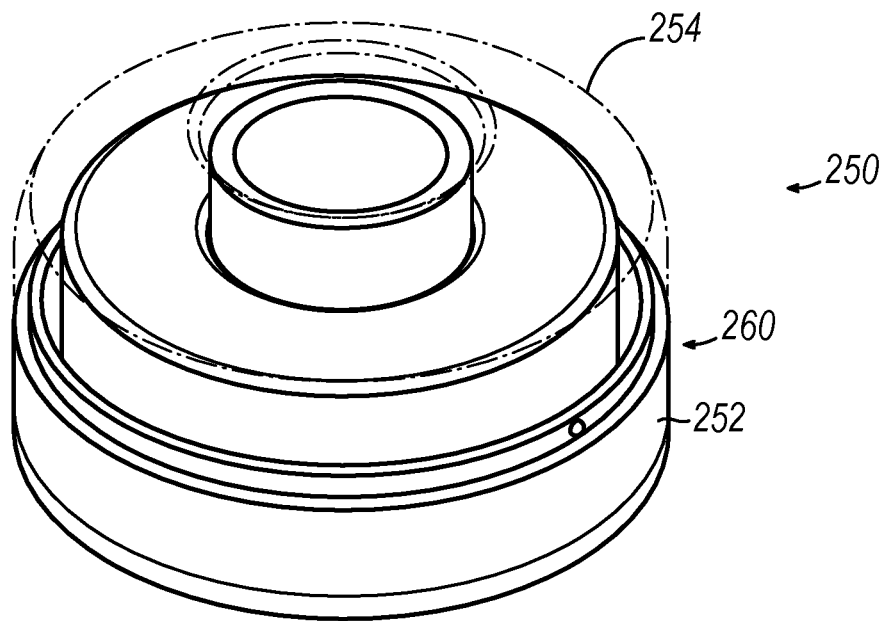
FIG. 26
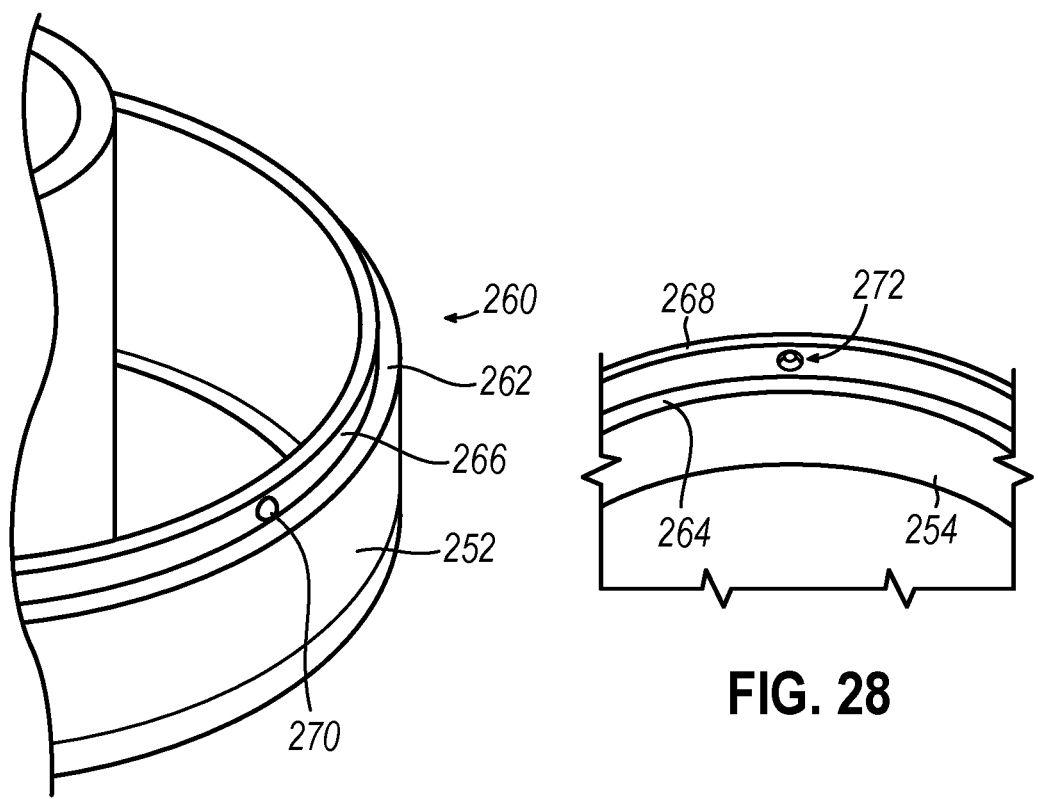
FIG. 27
FIG. 28

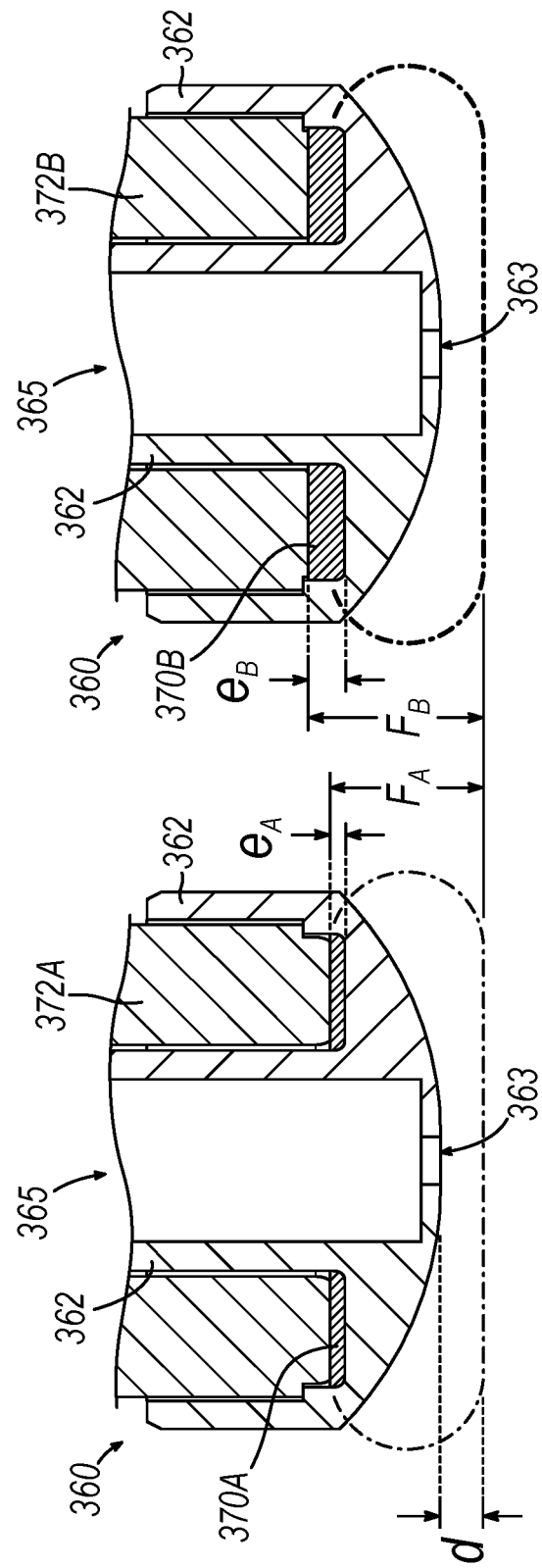

IMPLANTABLE SPHINCTER ASSISTANCE DEVICE WITH HOLDING, ALIGNING OR CLAMPING FEATURES INTEGRATED INTO HOUSING

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, heathy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes the stomach relative to the lower esophagus; or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein, in its entirety; U.S. Pat. No. 7,695,427, entitled "Methods and Apparatus for Treating Body Tissue Sphincters and the Like," issued Apr. 13, 2010, the disclosure of which is incorporated by reference herein, in its entirety; U.S. Pat. No. 8,070,670, entitled "Methods and Devices for Luminal and Sphincter Augmentation," issued Dec. 6, 2011, the disclosure of which is incorporated by reference herein, in its entirety; and U.S. Pat. No. 8,734,475, entitled "Medical Implant with Floating Magnets," issued May 27, 2014, the disclosure of which is incorporated by reference herein, in its entirety.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 26 depicts a perspective view of another exemplary bead;

FIG. 27 depicts a perspective view of a first housing of the bead of FIG. 26;

FIG. 28 depicts a perspective view of a second housing of the bead of FIG. 26;

FIG. 38 depicts a cross-sectional view of alternative unibody beads of FIG. 37A having epoxy surfaces with different thicknesses;

Figure 1:
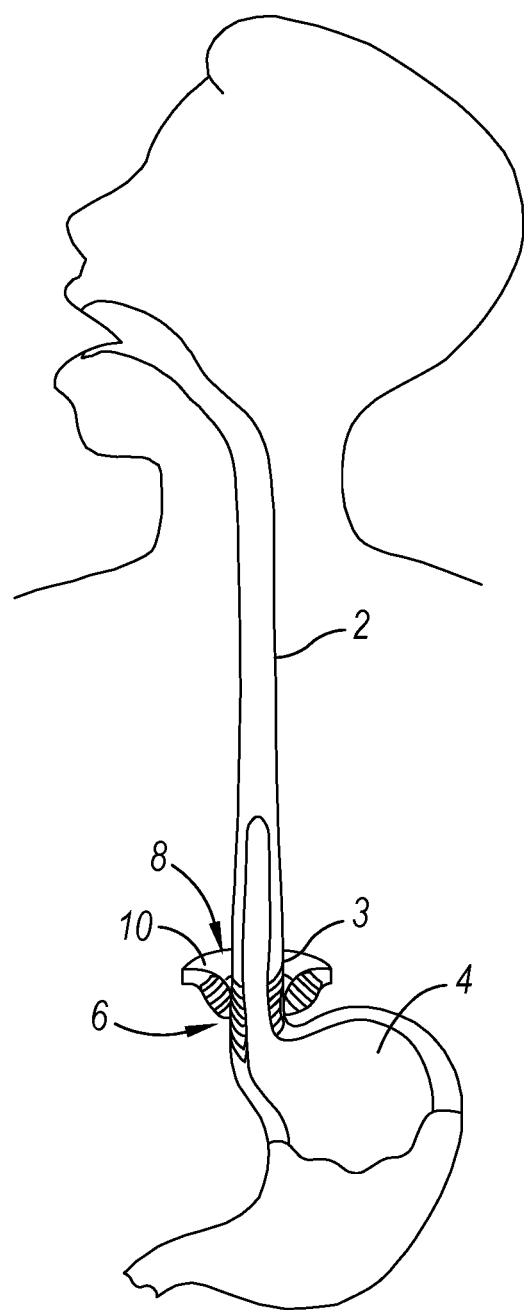
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Example of Sphincter Augmentation Device

Figure 2:
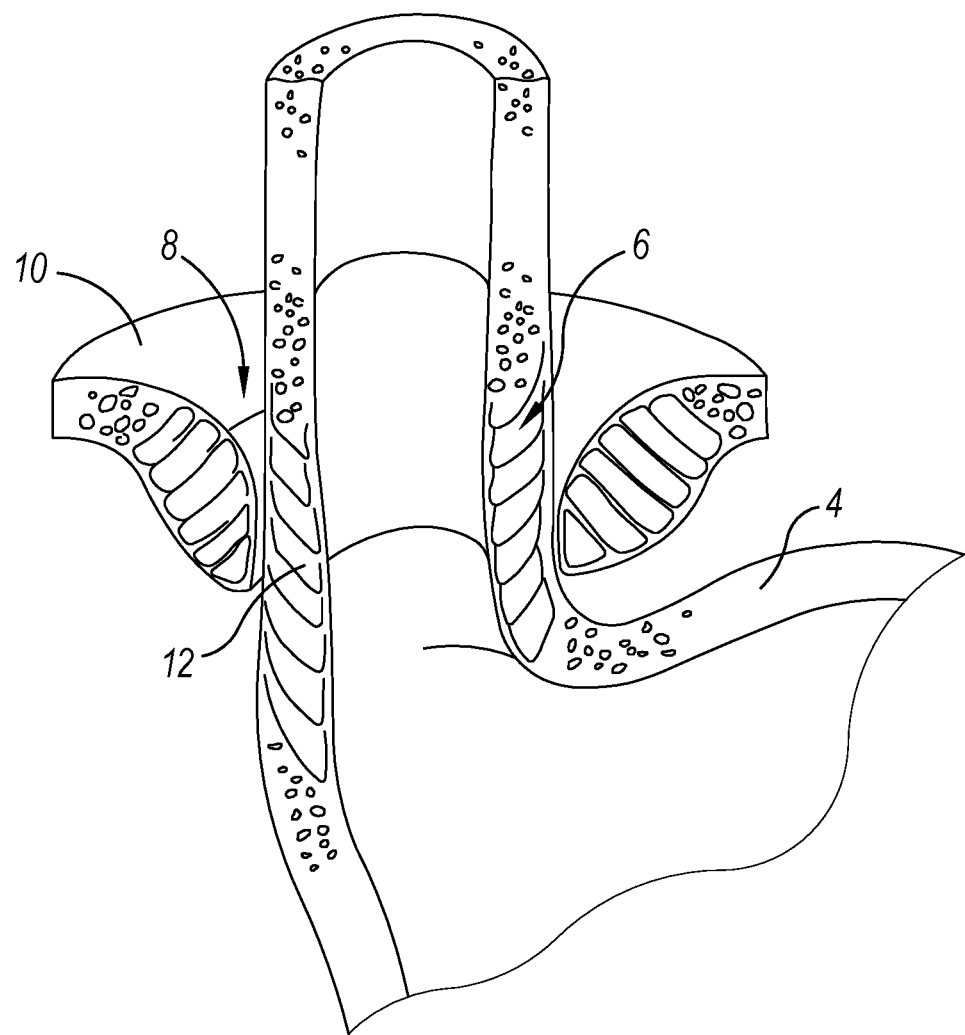
FIG. 2 depicts a cross-sectional isometric view, taken along a coronal plane of the body, of a human esophago-gastric junction.
Figure 3:
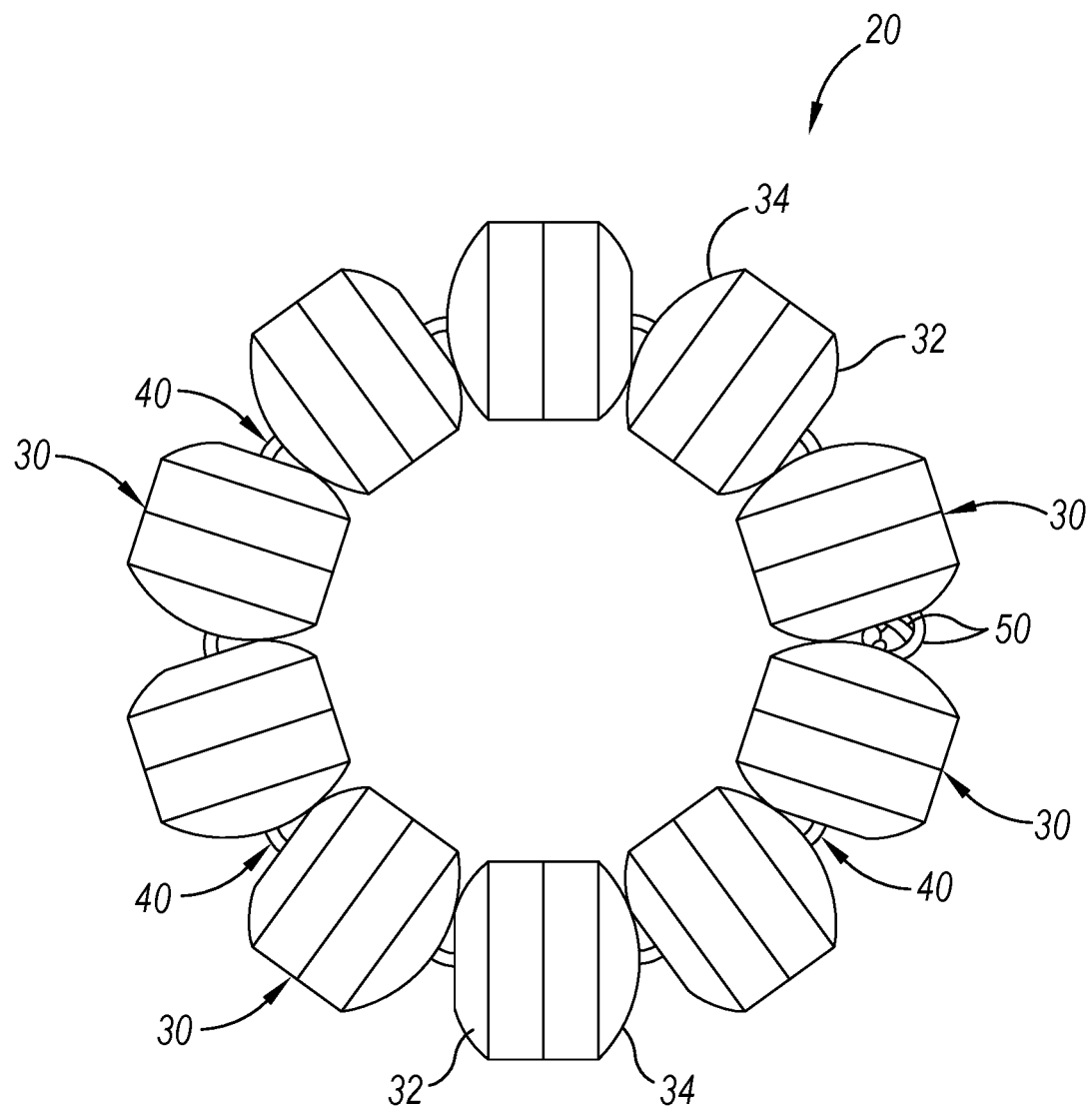
FIG. 3 depicts a top plan view of an example of a sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
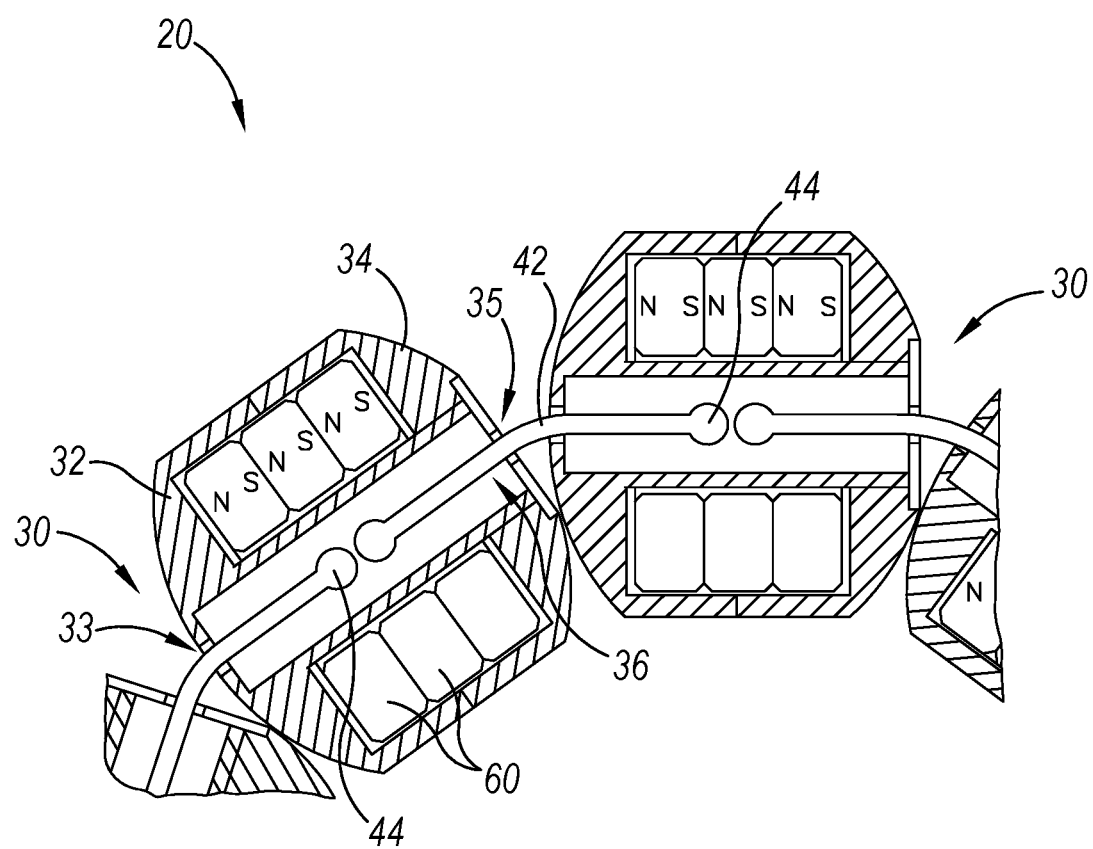
FIG. 4 depicts a partial, cross-sectional view of a portion of the sphincter augmentation device of FIG. 3.

FIGS. 3-5B show an example of a sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along links (40) through a restricted range of motion.

Figure 5A:
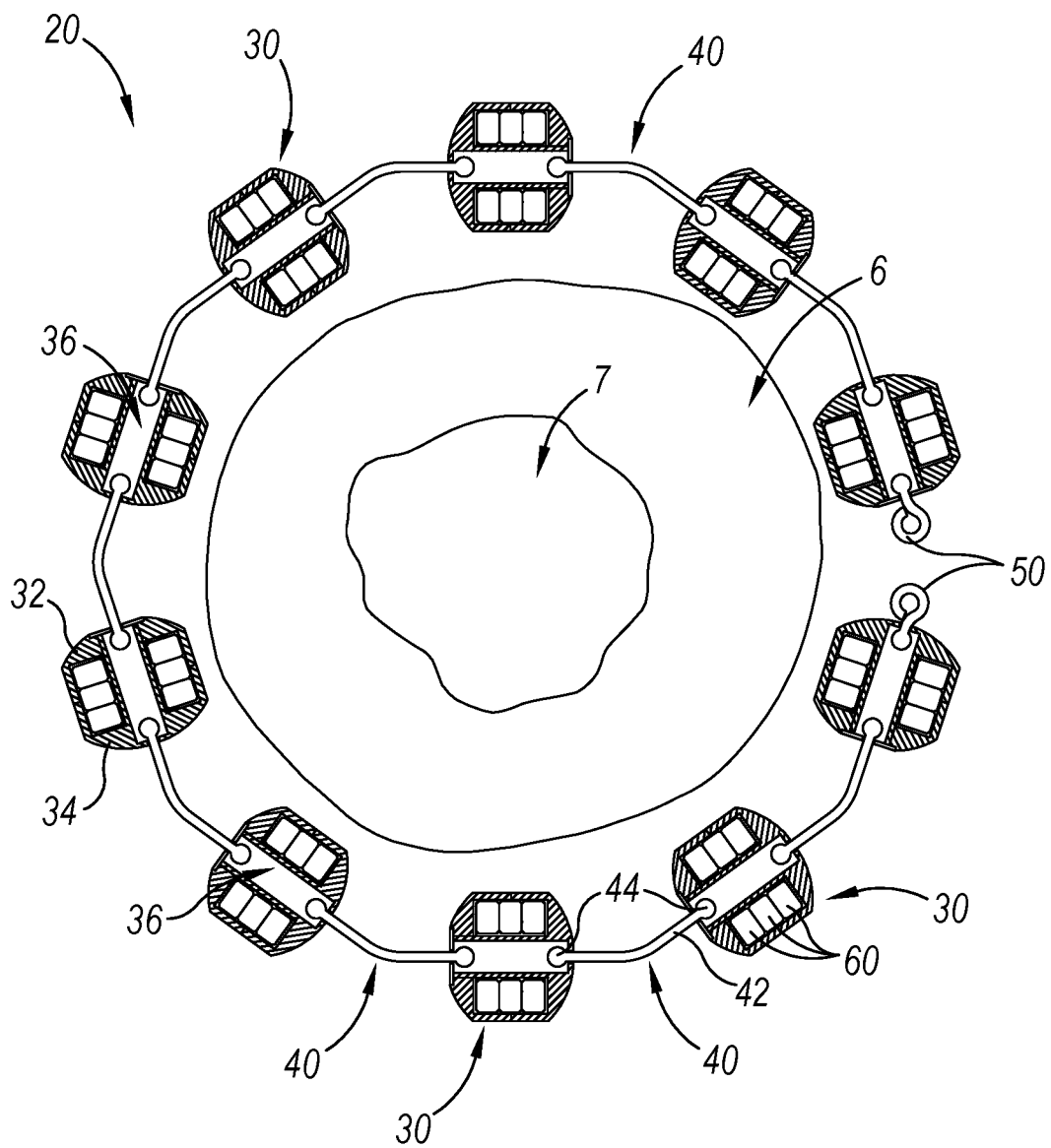
FIG. 5A depicts a top, cross-sectional view of the sphincter augmentation device of FIG. 3 positioned about an LES, with the sphincter augmentation device in an open and expanded configuration.
Figure 5B:
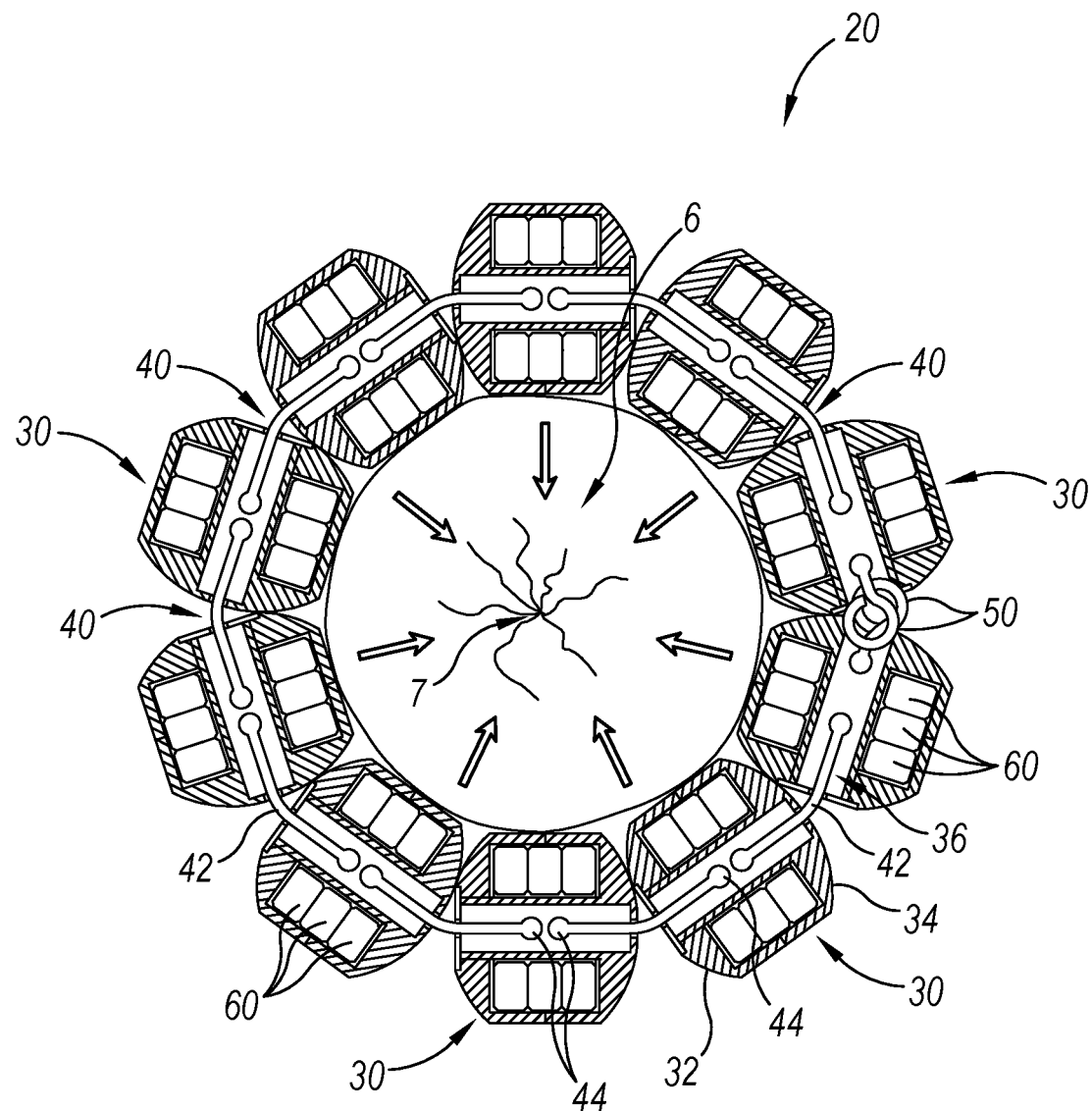
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. Pat. No. 10,405,865, entitled "Method for Assisting a Sphincter," issued Sep. 10, 2019, the disclosure of which is incorporated by reference herein, in its entirety. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein, in its entirety; and/or U.S. Pat. No. 10,405,865, the disclosure of which is incorporated by reference herein, in its entirety.

II. Example of 3D Printed Magnetic Elements

As mentioned above, magnets (60) are oriented within beads (30) such that each bead (30) is magnetically attracted to adjected beads (30). As also mentioned above, the intensity of magnetic fields between adjacent magnets (60) should be high enough to substantially maintain opening (7) in a closed state to prevent GERD (or any other undesirable event); while also being low enough to allow for LES (6) to expand radially during swallowing, etc., while maintaining a magnetic bias toward the closed state in accordance with the description herein. Therefore, it may be desirable to manufacture and assemble device (20) in such a manner to precisely and consistently control the intensity and/or direction of the magnetic fields generated between magnets (60) in adjacent beads (30) during exemplary use of device (20) in accordance with the description herein.

Traditional manufacturing methods of producing magnets (60) may include various limitations that may adversely affect the ability to precisely and consistently control/predict the intensity and/or direction of magnetic field generated between magnets (60) in adjacent beads (30). For example, current magnets (60) may be limited to a single magnet formulation during manufacturing. In other words, a single material may be used during a conventional manufacturing process of magnet (60)

As another example, when Samarium-Cobalt ("SmCo") or Neodymium are used to produce magnets (60), the SmCo or Neodymium material may first be converted into a fine powder. The fine powder may then be placed into a die cavity of a specialized tool on a press, which allows punches to compact the powder to form the general shape of magnets (60). Just prior to compaction of the powder, a magnetic aligning field is applied to the powder such that all the magnetic regions of the compacted powder are pointing in a prescribed direction. After reaching room temperature, the newly compacted structure undergoes a tempering heat treatment, which may shrink the shape of magnet (60) about 15-20% linearly. After sintering, magnet (60) may have a rough surface and only approximate dimensions such that sintered magnets (60) may require some degree of secondary processing and/or finishing. For example, sintered magnets (60) may receive at least some degree of machining, which can include griding surfaces, slicing magnets (60) into smaller parts, etc. The magnetic material may be both brittle and very hard, which may require diamond wheels for slicing and diamond/special abrasive wheels for grinding.

Compacting powder in a hydraulic or mechanical press may limit the potential shape of magnets (60) to simple cross-sections that can be pushed out of the die cavity. Manufacturing magnets (60) with simple cross-sections may limit the ability to manufacture magnets (60) with complex geometries to precisely control/predict/tune the intensity and/or direction of the magnetic fields generated between magnets (60) in adjacent beads (30) during exemplary use of device (20) in accordance with the description herein. Additionally, secondary processing and/or finishing sintered magnets (60) in order to form accurate/more complex geometries may result in various undesirable consequences. For example, machining sintered magnets (60) may result in magnets (60) having sharp edges; which, due to the brittle nature of the magnetic materials, may make the edges prone to undesirable chipping. As another example, forming complex geometries via grinding and cutting or other conventional secondary/finishing processes may result in magnets (60) with unacceptable geometry tolerances due to tool wear or other reasons as would be apparent to one skilled in the art in view of the teachings herein. Magnets (60) with unacceptable geometry tolerances may result in undesirable magnetic fields during use of device (20) and/or other undesirable consequences as would be apparent to one skilled in the art in view of the teachings herein.

Therefore, it may be desirable to manufacture magnets (60) with more complex geometries while maintaining such geometries within manufacturing tolerances. Manufacturing magnets (60) with more complex geometries within manufacturing tolerances may allow for more precise control of the intensity and/or direction of the magnetic fields generated by magnets (60) of adjacent beads (30) during use of device (20), such that magnets (60) may be produced with predictable properties on a consistent basis resulting in a more predictable and consistent performance of devices (20) incorporating such magnets (60).

Figure 6:
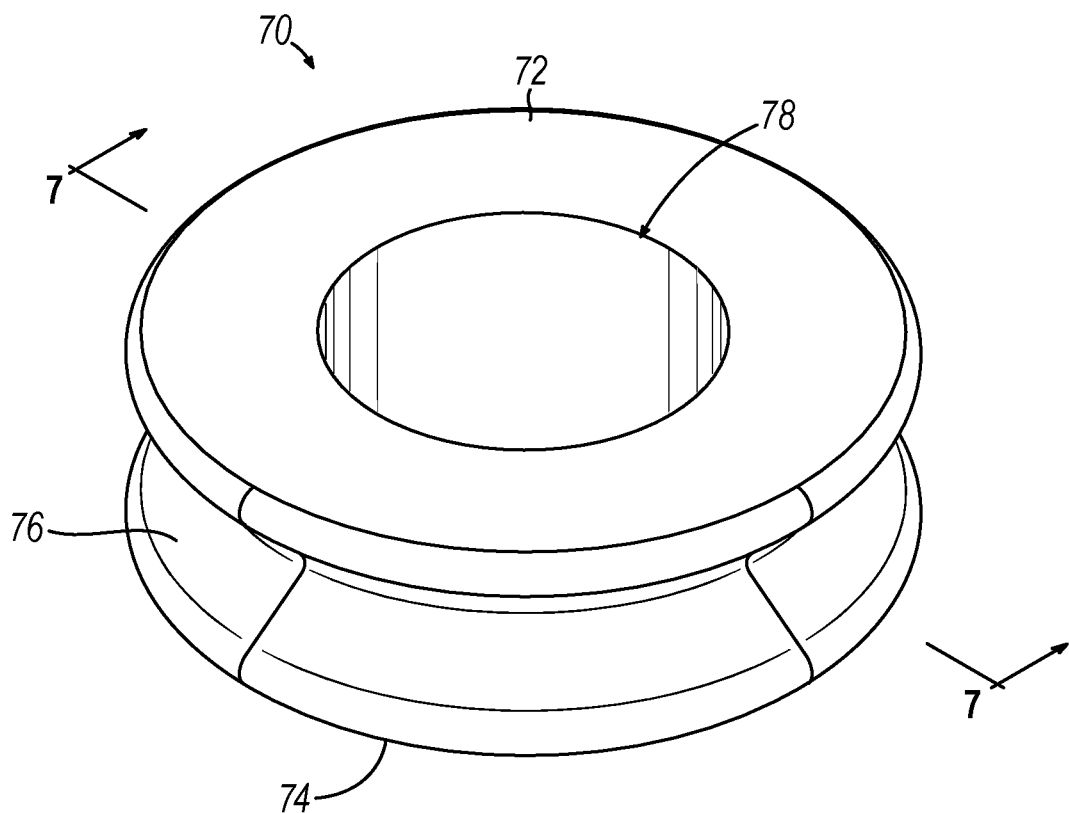
FIG. 6 depicts a perspective view of an exemplary magnet that may be readily incorporated into the sphincter augmentation device of FIG. 3
Figure 7:
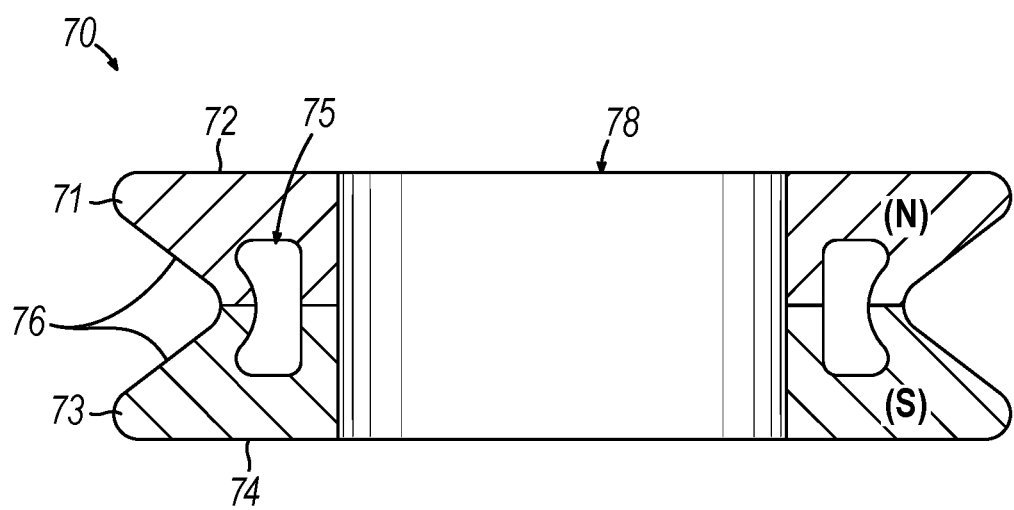
FIG. 7 depicts a cross-sectional view of the magnet of FIG. 6, taken along line 7-7 of FIG. 6.

FIGS. 6-7 show an exemplary magnet (70) that may be readily incorporated into device (20) in replacement of one or more magnets (60) described above. Magnet (70) is formed via an additive process, such as 3D printing, thereby allowing magnet (70) to be formed with unique and complex geometries within manufacturing tolerances. For example, a 3D printer may use a suitable powdered form of magnetic material and/or granules of magnetic material, apply the powdered/granule magnetic material in successive layers, and melt selected portions of each layer in order to bind the particles to form a desired shape of magnetic (70) with suitable magnetic properties. Using 3D printing technology, magnets (70) may be formed with more complex geometries without the above-mentioned constraints of traditional manufacturing methods.

Magnet (70) includes a north pole magnetic section (71) and a south pole magnetic section (73). Magnet (70) may be magnetized with north pole magnetic sections (71) and south pole magnetic section (73) utilizing any suitable means as would be apparent to one skilled in the art in view of the teachings herein. Magnet (70) is formed in a generally annular shape in order to define a central through hole (78) dimensioned to fit around a portion of bead (30) defining chamber (36) such that magnet (70) is completely sealed within a respective bead (30) when assembled. Similar to magnets (60) described above, magnets (70) may be stacked with alternating magnetic polarity within housings (32, 34) to thereby generate an attractive magnetic field with magnets (70) of an adjacent bead (30).

Since magnet (70) is formed via 3D printing, magnet (70) may be formed with complex shapes. For example, north pole magnetic section (71) and south pole magnetic section (73) may each have a respective widened annular side wall (72, 74) such that magnet (70) is the thickest (as shown in FIG. 7) near side walls (72, 74) and the thinnest near a neutral portion of magnet (70). Therefore, magnets (70) include a pair of tapered walls (76) extending from a terminating end of each side wall (72, 74) toward a magnetically neutral portion of magnet (70). As best shown in FIG. 7, tapered walls (76) give magnet (70) a varying cross-sectional geometry. In some instances, magnet (70) may extend a suitable length between annular faces (72, 74) such that one magnet (70) may be utilized within a single bead (30), rather than a plurality of magnets (60, 70) stacked on top of each other. Widened annular side walls (72, 74) may be geometrically dimensioned in order to finely tune the magnetic fields (with regards to intensity and/or direction) generated by magnets (70) between adjacent beads (30), thereby allowing the magnetic fields generated by magnets (70) to be optimized to urge opening (7) toward a closed state to prevent GERD while also allowing LES (60) to expand radially in accordance with the description herein.

While in the current example, magnet (70) includes a widened annular side wall (72, 74) for both magnetic sections (71, 73), this is merely optional. For example, only one magnetic section (71, 73) may have a widened annular side wall (72, 74) such that the thickness of one polar magnetic section (71, 73) substantially deviates, while the thickness of the other polar magnetic section (71, 73) remains substantially uniform. In such instances, magnet (70) may be stacked with other magnets (60, 70) (similar to the stacked orientation of magnets (60) within a single bead (30) shown in FIG. 4) such that widened side wall (72, 74) is adjacent to another bead (30) of device (20). In such examples, one magnet (70) having a single widened annular side wall (72) may be utilized with a second magnet (70) having a single widened annular side wall (74), with a magnet (60) interposed between.

In the current example, annular side walls (72, 74) are shown extending along respective planes that are substantially parallel with each other. However, this is merely optional. In some instances, side walls (72, 74) may extend along respective planes that intersect with each other to form an angle, thereby allowing one circumferential portion of magnet (70) to be thicker than a second circumferential portion.

Additionally, as shown in FIG. 7, magnet (70) may also include as least one hollow pocket (75). In some examples, hollow pocket (75) is annular in nature such that a single hollow pocket (75) extends completely around the circumference of magnet (70). In other examples, an annular array of discrete, angularly-spaced hollow pockets (75) may be used. Yet in other examples, only selected circumferential sections of magnet (70) may define hollow pockets (75). Hollow pockets (75) may be placed within magnet (70) at any suitable location as would be apparent to one skilled in the art in view of the teachings herein.

Having magnet (70) formed with at least one hollow pockets (75) and/or thicker circumferential sections, and/or wider side walls oriented with respect to adjacent beads (30) may allow magnets (70) to be designed and manufactured in such a way to reduce the amount of material used produce magnet (70), reduce the costs associated with producing magnets, reduce the weight of magnet (70), as well as reduce the tendency of magnetic field re-orientation when placed in another magnetic field. The presence and configuration of one or more hollow pockets (75) may also be selected or varied to fine tune the magnetic field generated by magnet (70).

Utilizing conventional manufacturing methods, magnets (60,70) may be limited to a single magnetic formulation or composition during manufacturing. For example, when magnetic material is turned into a fine powder to fill a die cavity, a powder having substantially uniform material composition may be used. With 3D printing, the possibility of combining multiple materials while manufacturing magnet (60, 70) may further optimize the intensity and direction of generated magnetic fields in accordance with the description herein. Therefore, in some instances, it may be desirable to 3D print a magnet (60, 70) with multiple materials, in combination with or as an alternative to, complex geometries as exemplified in magnet (70) describe above. Thus, the 3D printing process may enable fine tuning of the formulation of materials that are used to form a magnet (60, 70), which may in turn effect fine tuning of the magnetic properties of magnet (60, 70) far beyond the capabilities of conventional magnetic manufacturing techniques.

Figure 8:
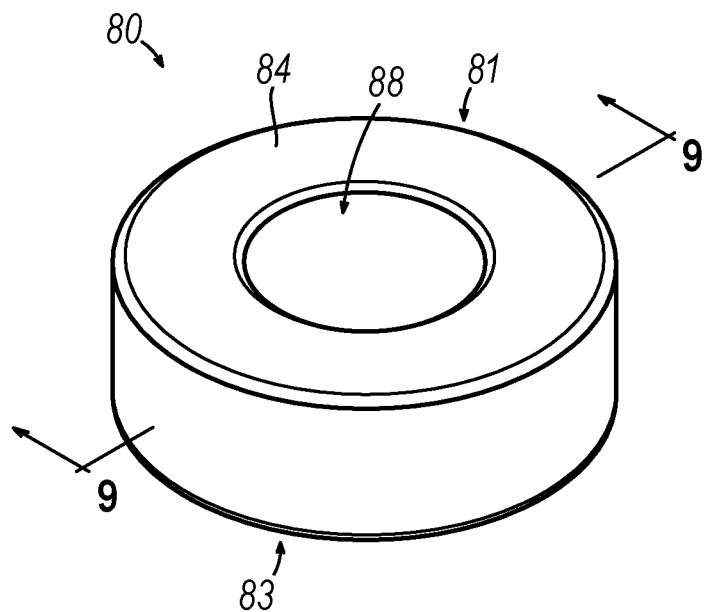
FIG. 8 depicts a perspective view of another exemplary magnet that may be readily incorporated into the sphincter augmentation device of FIG. 3.
Figure 9:
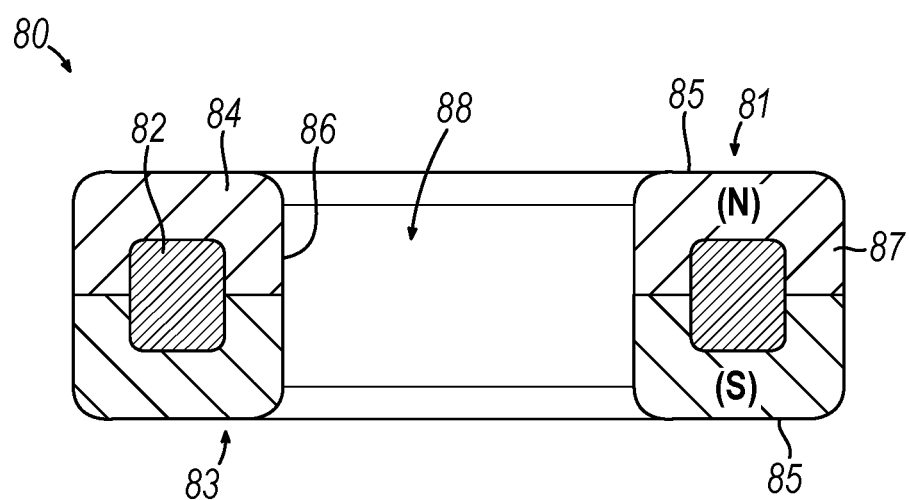
FIG. 9 depicts a cross-sectional view of the magnet of FIG. 8, taken along line 9-9 of FIG. 8.

FIGS. 8-9 show an exemplary magnet (80) that may be readily incorporated into device (20) in replacement of one or more magnets (60, 70) described above. Similar to magnet (70), magnet (80) is formed via an additive process, such as 3D printing, thereby allowing magnet (80) to be formed with a combination of multiple materials. While magnet (80) is shown with a generally annular or toroidal shape with a uniform thickness and constant cross-sectional geometry as shown in FIG. 9, it should be understood magnet (80) may have any suitable shape as would be apparent to one skilled in the art in view of the teachings herein, such as the complex geometries described above for magnet (70).

Magnet (80) is formed via an additive process, such as 3D printing, thereby allowing magnet (80) to be formed with a combination of multiple materials. For example, a 3D printer may use a first suitable powder formed of a magnetic material and another suitable powered material (which may or may not be magnetic), apply the powdered materials in a desired pattern in successive layers, and apply heat to selected portions of each layer in order to bind the particles to form a desired shape of magnet (80) with suitable magnetic properties. As will be described in greater detail below, using 3D printing technology may allow magnets (80) to be formed with combinations of materials compared to the above-mentioned single-material constraints of traditional manufacturing methods.

Magnet (80) includes a north pole magnetic section (81) and a south pole magnetic section (83). Magnet (80) may be magnetized with north pole magnetic sections (81) and south pole magnetic section (83) utilizing any suitable means as would be apparent to one skilled in the art in view of the teachings herein. Magnet (80) is formed in a generally annular shape, thereby having a pair of annular side walls (85), an outer diameter surface (87), and an inner diameter surface (86) defining a central through hole (88). Central through hole (88) is dimensioned to fit around a portion of bead (30) defining chamber (36) such that magnet (80) is completely sealed within a respective bead (30) when assembled. Similar to magnets (60, 70) described above, magnets (80) may be stacked with alternating magnetic polarity within housings (32, 34) to thereby generate an attractive magnetic field with magnets (80) of an adjacent bead (30).

In the current example, as best shown in FIG. 9, magnet (80) is formed with a first material (82) and a second material (84). In the current example, first material (82) is coated or encased by second material (84) such that second material (84) covers first material (82) entirely in order to form diameters (86, 87) and walls (85). While the thickness of second material (84) surrounding first material (82) is shown in the current example and being substantially uniform, this is merely optional. For example, the thickness of coating provided by second material (84) may deviate such that first material (82) is closer to one side wall (85) compared to the other, and/or closer to one diameter wall (86, 87) compared to the other.

While first material (82) acts as a core and second material (84) acts as a coating or casing, this is merely optional. For example, a portion of first material (82) and second material (84) may both be exposed to the exterior in order to form diameter (86, 87) or walls (85). First material (82) and second material (84) may be oriented relative to each other to form any suitable cross-sectional geometry relative to each other as would be apparent to one skilled in the art in view of the teachings herein. In some instances, second material (84) may be applied with varying thicknesses and cross-sectional geometries, such that the thickness and cross-sectional profile of second material (84) does not necessarily need to be uniform across the height, width, thickness, etc., of first material (82). In some instances, some regions of first material (82) may even be left exposed by second material (84).

Additionally, in other examples, a third material, fourth material, fifth material, or more materials may be utilized in order to form magnet (80). Such additional materials may be used to form any suitable portion of magnet (80) as would be apparent to one skilled in the art in view of the teachings herein. For example, such materials may be utilized as a coating on magnet (80) in order to cover the magnet (80) entirely. Any suitable combination of materials to form any suitable cross-sectional geometry may be utilized as would be apparent to one skilled in the art in view of the teachings herein.

Materials (82, 84) may have different magnetic properties, thereby allowing for additional customization of a magnetic field to better control the direction and magnetic pull of magnet (80) during exemplary use in accordance with the description herein. For example, magnet (80) may be printed with a combination of ferromagnetic and non-magnetic materials. Therefore, in one instance, first material (82) may be formed of a suitable ferromagnetic material, while second material (84) may be formed of a suitable non-magnetic material that would redirect and/or dampen the magnetic field generated in accordance with the description herein. In another instance, first material (82) may be formed of a suitable non-magnetic material, second material (84) may be formed of a suitable ferromagnetic material; while a third non-magnetic material may be utilized to act as a coating on magnet (80). Therefore, utilizing a combination of ferromagnetic materials and non-magnetic materials could allow for additional customization of the generated magnetic fields to control the direction and magnetic force of magnets (80) while used in accordance with the description herein.

As another example, magnet (80) may be printed with multiple ferromagnetic materials. For instance, first material (82) may be formed of a first ferromagnetic material, and second material (84) may be formed of a second ferromagnetic material. First ferromagnetic material and a second ferromagnetic material may have different magnetic properties. Therefore, utilizing a combination of different ferromagnetic materials could allow for additional customization of the generated magnetic fields to control the direction and magnetic pull of magnets (80) while used in accordance with the description herein.

In some instances, more than two ferromagnetic materials are utilized to form any suitable geometry as would be apparent to one skilled in the art in view of the teachings herein. In some instances, one or more ferromagnetic materials are utilized with one or more non-magnetic materials.

In some instances, first material (82), second material (84), and/or any other utilized material may be the same or similar magnetic material, but just 3D printed with different densities, which may therefore further customize the generated magnetic fields to control the direction and magnetic pull of magnets (80) while used in accordance with the description herein.

In some instances, rather than 3D printing an entire magnet (70, 80) in accordance with the description above, it may be desirable to 3D print additional features on top of traditionally manufactured magnets (60). Utilizing 3D printing to print design features onto a traditionally manufactured magnet (60) may allow for custom design features at defined locations of magnet (60) without requiring use of traditional secondary processes described above. Therefore, 3D printing design features onto an otherwise-traditionally manufactured magnet (60) may allow for more complex geometries and customization of generated magnetic fields at targeted locations while also minimizing costs related to generating scrap and utilizing complex equipment. Additionally, utilizing an additive process, rather than traditional secondary processing methods, may result in reduced amounts of sharp edges, which may reduce the potential of chipping described above and increase the robustness in an exterior coating of magnet (60).

In some instances, it may be desirable to 3D print non-magnetic and/or magnetic elements onto magnet (60, 70, 80). Such 3D printed design features may include 3D printed magnetic elements onto an otherwise-traditionally manufactured magnet (60) in order to further customize magnetic fields generated in accordance with the description herein. This may allow further customization of the generated magnetic fields of an otherwise-traditionally manufactured magnet (60). Another example of magnetic or non-magnetic 3D printed design features may include an orientation feature to ensure magnet (60, 70, 80) is consistently and/or accurately rotationally oriented within a respective bead (30) once assembled. 3D printed orientation features on magnets (60, 70, 80) may interact with a complementary orientation feature of either or both housing (32, 34) once assembled, to thereby accurately place magnet (60, 70, 80) within housings (32, 34) of bead (30).

Figure 10:
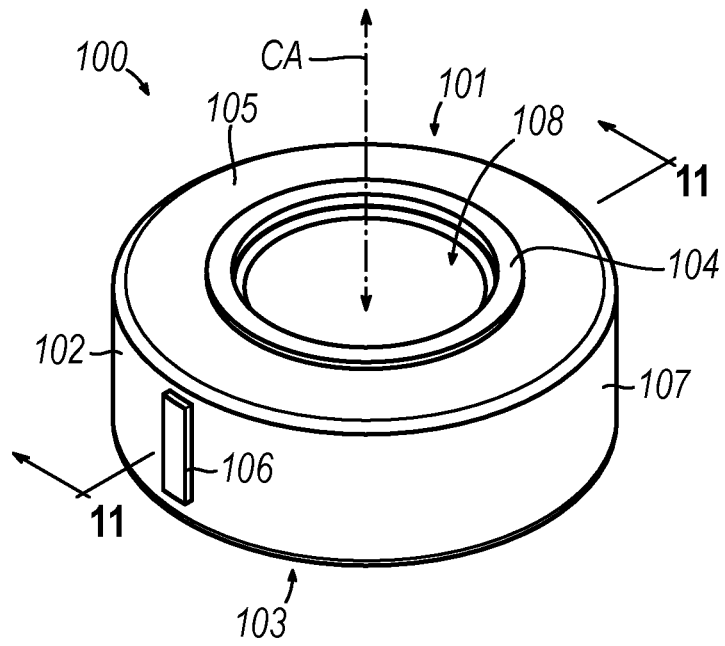
FIG. 10 depicts a perspective view of an exemplary magnet assembly that may be readily incorporated into the sphincter augmentation device of FIG. 3.
Figure 11:
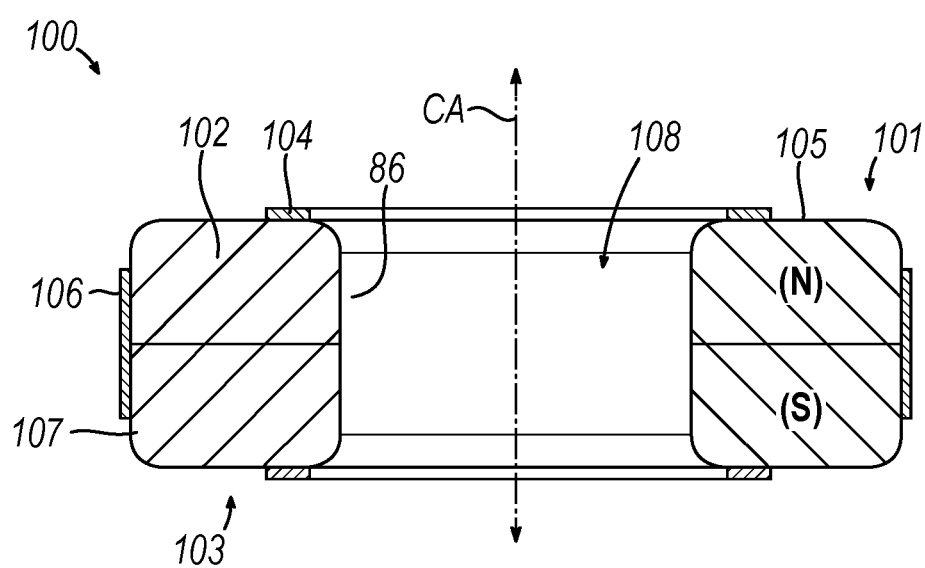
FIG. 11 depicts a cross-sectional view of the magnet assembly of FIG. 10, taken along line 11-11 of FIG. 10.

FIGS. 10-11 show an exemplary magnet assembly (100) that may be readily incorporated into device (20) described above. Magnet assembly (100) in the current example includes an annular or toroidal rare-earth permanent magnet (102), a pair of 3D printed annular magnetic elements (104) associated with annular side walls (105) of magnet (102), and a pair of 3D printed orientation bodies (106) extending from outer diameter surface (107) of magnet (102). Magnet (102) may be substantially similar to magnet (60) described above. Therefore, magnet (102) defines a central through hole (108) that may be substantially similar to central through hole (78, 88) described above. Central through hole (108) extends along a central axis (CA) of magnet (102). Magnet (102) may be manufactured utilizing traditional manufacturing methods. Alternatively, magnet (102) may be manufactured utilizing any other suitable methods as would be apparent to one skilled in the art in view of the teachings herein, such as 3D printing.

Figure 14:
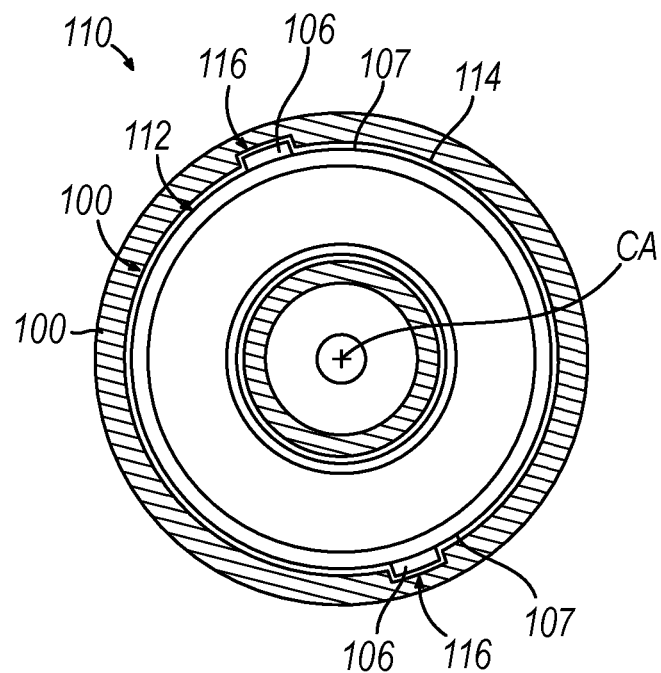
FIG. 14 depicts another cross-sectional view of the sphincter augmentation device of FIG. 12, taken along line 14-14 of FIG. 12.

As will be described in greater detail below, 3D printed annular magnetic elements (104) may be 3D printed onto any suitable portion of magnet (102) in order to more accurately control the intensity and direction the magnetic field generated by magnet (102) during exemplary use in accordance with the description herein. As will also be described in greater detail below, orientation bodies (106) are configured to mate with a corresponding orientation slot (116) (see FIG. 14) of an exemplary bead (110) in order to rotationally align magnet assembly (100) relative to magnet housing chamber (112) about central axis (CA) once assembled.

3D printed magnetic elements (104) may be 3D printed onto magnet (102) after the magnet (102) has been formed in accordance with the description herein. 3D printed magnetic elements (104) may be formed of any suitable magnetic element as would be apparent to one skilled in the art in view of the teachings herein. 3D printed magnetic elements (104) may be printed from the same magnetic material as magnet (102), a different magnetic material compared to magnet (102), a ferrous material, a non-ferrous material, or any suitable combination of the above-mentioned materials. 3D printed magnetic elements (104) may suitably alter the magnetic field generated by magnet (102) during exemplary use. Therefore, magnetic elements (104) may be utilized to allow for more accurate control of the intensity and/or direction of a magnetic field generated by magnet assembly (100) in accordance with the description herein. Since 3D printed magnetic elements (104) are added on top of magnet (102) via the additive process of 3D printing, magnetic elements (104) may allow formation of customized and complex magnet geometries of magnet assembly (100) without utilizing traditional secondary processes described above.

Figure 12:
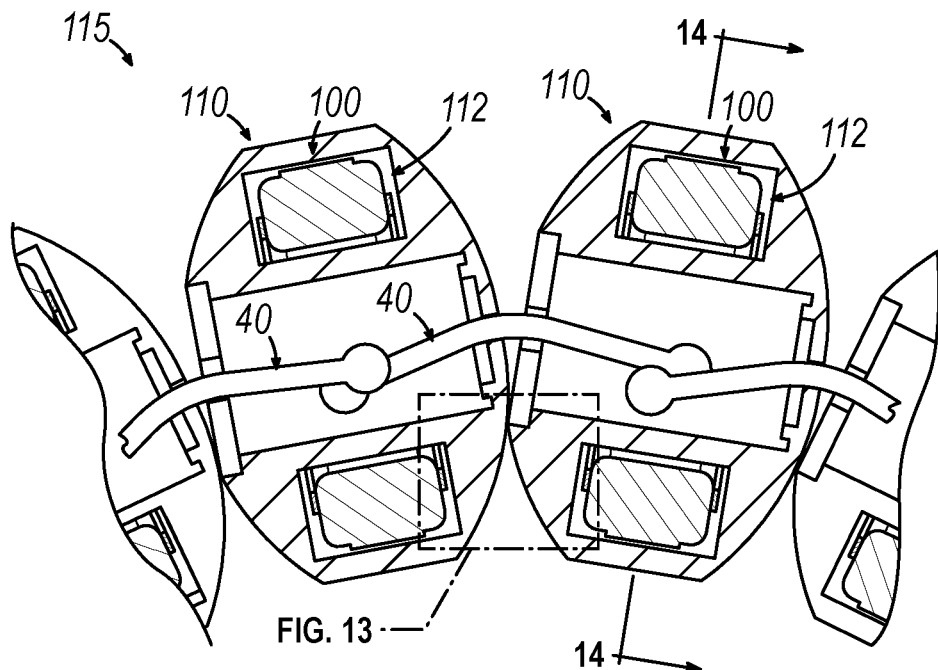
FIG. 12. depicts a cross-sectional view of a selected portion of an alternative sphincter augmentation device which incorporates the magnet assembly of FIG. 10.
Figure 13:
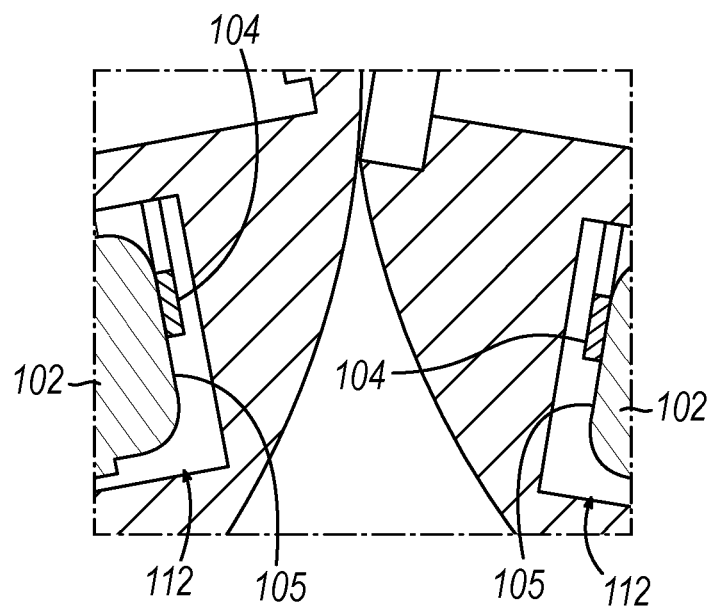
FIG. 13 depicts an enlarged cross-sectional view of a portion of the sphincter augmentation device of FIG. 12.

FIGS. 12 and 13 show magnet assemblies (100) housed within magnetic housing chambers (112) defined by a respective bead (110). Beads (110) are substantially similar to beads (30) described above, with differences elaborated below. Therefore, beads (110) are slidably coupled to each other via links (40). Beads (110), links (40), and magnet assemblies (100) may be used in order to form a sphincter augmentation device (115) that is substantially similar to sphincter augmentation device (20) described above, with differences described herein. Beads (110) define magnet housing chamber (112) that houses a respective magnet assembly (100). Therefore, magnet assemblies (100) within adjacent beads (30) generate suitable magnetic fields in order to function in a similar fashion as device (20) described above. However, as best shown in FIG. 13, the complex geometry provided by the combination of magnetic elements (104) of adjacent magnet assemblies (100) and magnets (102) may help fine tune, or otherwise more accurately control the intensity and direction of the generated magnetic fields, in order to optimize the functionality of device (115) as compared to device (20) described above. For example, the combination of magnetic elements (104) and magnets (102) may allow for enhancing a portion of the magnetic field at focused locations to promote interactions between beads (110) at desirable orientations relative to each other; and/or with constrictive forces being applied to the LES (6) in a desirable distribution about the LES (6), etc.

In the current example, 3D printed magnetic elements (104) are annular in geometry and extend from annular side walls (105) of magnet (102). However, 3D printed magnet elements (104) may have any suitable geometry as would be apparent to one skilled in the art in view of the teachings herein. For example, rather than being a single annular piece, 3D printed magnetic elements (104) on one annular side wall (105) may be formed in an arched array of individual magnetic elements (104) on a single annular side wall (105). As another example, only one 3D printed magnetic element (104) may be 3D printed on a single annular side wall (105), rather having the presence of 3D printed magnetic elements (104) on both annular side walls (105). As another example, 3D printed magnetic elements (104) may be located on a circumferential segment of annular side wall (105), rather than extending completely around annular side wall (105).

With the possibility of forming complex geometries of magnets (60, 70, 80) and magnetic assembly (100), it may be desirable to control the orientation of magnet (60, 70, 80) and/or magnetic assembly (100) within bead (30, 110) in order to better control the intensity and direction of magnetic fields generated in accordance with the description herein. As mentioned above, magnet assembly (100) includes a pair of 3D printed orientation bodies (106) configured to mate with a corresponding orientation slot (116) (see FIG. 14) of an exemplary bead (110) in order to rotationally align magnet assembly (100) relative to magnet housing chamber (112) along central axis (CA) once assembled. Orientation bodies (106) of the present example are oriented parallel with central axis (CA) in this example, though orientation bodies (106) may instead have any other suitable orientation.

Bead (110) of the present example includes an interior chamber surface (114) that partially defines magnet housing chamber (112) and also defines orientation slots (116). Bead (110) may be 3D printed, produced through Metal injection Molding (MIM) or Powder Metallurgy (PM), or manufactured using any other suitable process, such that interior chamber surface (114) may accurately define magnet housing chamber (112). When inserting magnet assembly (100) into bead (110), magnet assembly (100) is dimensioned such that it will not fit within chamber (112) defined by bead (110) until 3D printed orientation bodies (106) are aligned with corresponding orientation slots (116). In some instances, 3D printed orientation body (106) and corresponding ordination slots (116) are dimensioned such that a particular annular side wall (105) is inserted within bead (110) first. If the particular annular side wall (105) is not inserted first, feature (106) and slots (116) may be dimensioned such that magnet assembly (100) does not properly sit within magnet housing chamber (112), such as by having magnet assembly (100) extend proud out of magnet housing chamber (112) prior to complete assembly.

Slots (116) and bodies (106) may be oriented such that when device (115) is fully assembled, magnetic assemblies (100) of adjacent beads (110) are suitably oriented relative to each other to further optimize (i.e., finely tune) magnetic fields generated in accordance with the description herein. In some instances, adjacent beads (110) may be prevented from rotating relative to each other about links (40), such that links (40) are keyed to beads, thereby inhibiting beads (110) from rotating relative to each other. Additionally, rotationally containing movement of magnetic assemblies (100) relative to beads (110) about central axis (CA) once assembled may inhibit undesirable movement of magnet assemblies (110) relative to beads (110), which may in turn inhibit undesirable deviations of the generated magnetic fields during exemplary use of device (115). Orientation bodies (106) and slots (116) may also be designed in order to inhibit translation of magnet assembly (100) within bead (110), thereby minimizing "float" of magnet assemblies (100) due to competing magnetic attraction between adjacent beads (110).

Any suitable number of 3D printed orientation bodies (106) may be used as would be apparent to one skilled in the art in view of the teachings herein. In some examples, only one orientation body (106) is used; while in other examples, three or more orientation bodies (106) are used. In examples where two or more orientation bodies (106) are used, each orientation body may be dimensioned to fit within a specific corresponding complementary orientation slot (116) of interior chamber surface (114) such that magnetic assembly (100) may only be inserted within magnet housing chamber (112) in a single angular orientation.

In some examples, orientation bodies (106) may include a magnetic material such that the presence of orientation body (106) affects the generated magnetic fields described herein. In other examples, orientation bodies (106) may include a non-magnetic material such that the presence of orientation bodies does not affect the generated magnetic field described herein.

Figure 15:
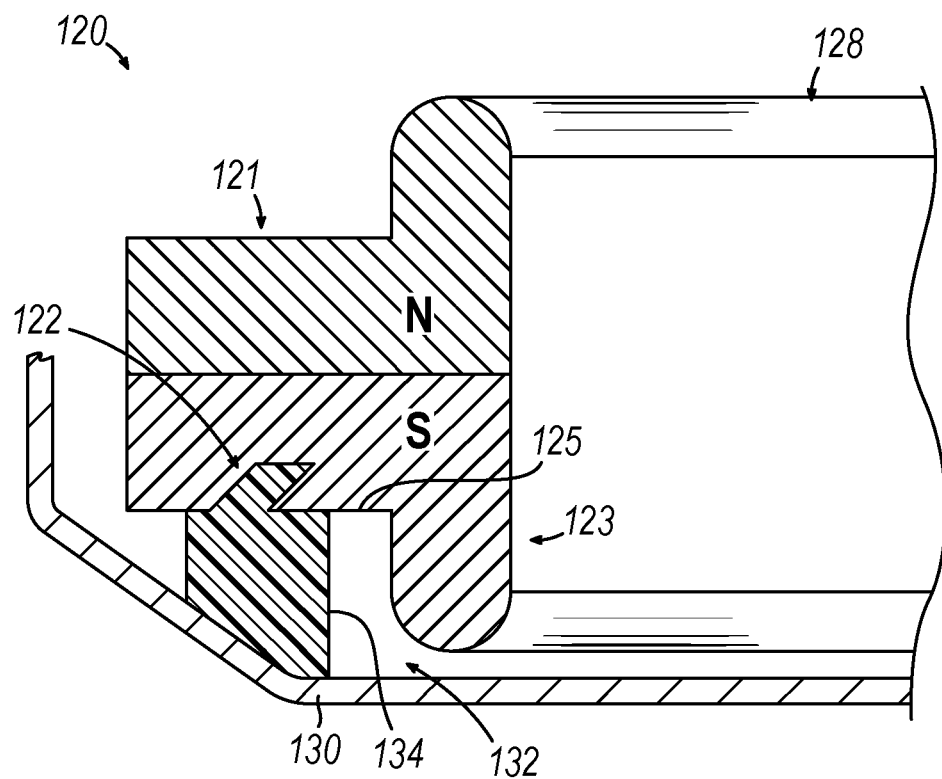
FIG. 15 depicts a cross-sectional view of an alternative magnet and bead which may be readily incorporated into the sphincter augmentation device of FIG. 12.
Figure 16:
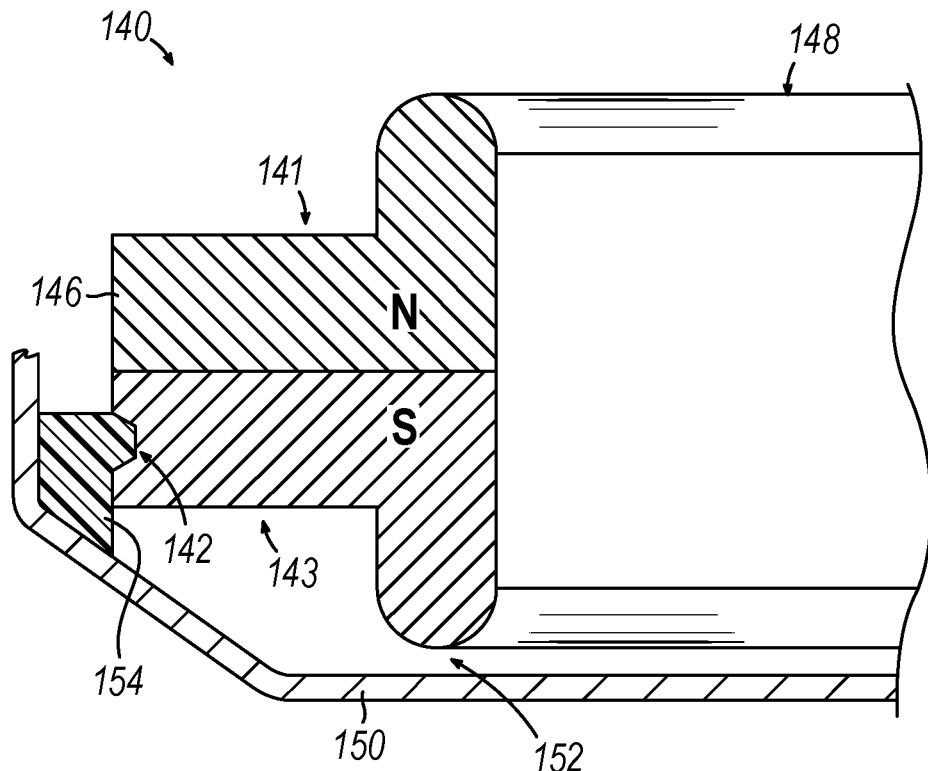
FIG. 16 depicts a cross-sectional view of an alternative magnet and bead which may be readily incorporated into the sphincter augmentation device of FIG. 12.

In the current example, orientation bodies (106) are associated with outer diameter surface (107) of magnet (102), while orientation slot (106) is associated with an interior chamber surface (114) of bead (110). However, this is merely optional, as a slot may be associated with magnet assembly (100) while an orientation body may be associate with bead (110). FIG. 15 shows on example of a magnet (120) and bead (130) where magnet (120) defines an orientation slot (122), and bead (130) includes a complementary orientation body (134) that is received in orientation slot (122); while FIG. 16 shows another example of a magnet (122); while FIG. 16 shows another example of a magnet (140) and bead (150) where magnet (140) defines an orientation slot (142) and bead (150) includes a complementary orientation body (154) that is received in orientation slot (142).

Magnet (120, 140) may be substantially similar to magnets (60, 70, 80, 102) described above, with differences elaborated below. Therefore, magnets (120, 140) each include a north pole magnetic section (121, 141), a south pole magnetic section (123, 143), and define a central through hole (128, 148), which are substantially similar to north pole magnetic section (71, 81, 101), south pole magnetic section (73, 83, 103), and central through hole (78, 88) described above, respectively, with differences elaborated below. Bead (130, 150) may be substantially similar to bead (30, 110) described above, with differences elaborated below. Therefore, bead (130, 150) defines a magnetic housing chamber (132, 152) that is substantially similar to magnetic housing chamber (112) described above.

Each magnet (120, 140) defines orientation slot (122, 142). Orientation slot (122) of magnet (120) is located on an annular side wall (125); while ordination slot (142) of magnet (142) is located on an outer diameter wall (146). Complementary orientation bodies (134, 154) of beads (130, 150) are located in order to suitably couple with a respective orientation slot (122, 142), thereby functioning in similar fashion to orientation body (106) and orientation slot (116) described above. It should be understood that orientation slot (122, 142) defined by magnet (120, 140) may be located at any suitable position as would be apparent to one skilled in the art in view of the teachings herein. Slots (122, 142) may be manufactured via 3D printing, or any traditional secondary processing method as would be apparent to one skilled in the art in view of the teachings herein.

III. Example of Housing with 3D Printed Shell Weld Interface Geometry

As mentioned above, each bead (30) comprises a pair of housings (32, 34) that are securely fastened to each other. Housings (32, 34) may be securely fastened to each other via welding. As also mention above, beads (110, 130, 150) may be 3D printed, or manufactured through MIM/PM, thereby allowing beads (110, 130, 150) to have unique geometries, such as defining orientation slots (116), or forming orientation bodies (134, 154) that may ensure magnet (100, 120, 140) is suitably rotationally aligned or translationally constrained relative to bead (110, 130, 150), thereby accurately controlling generated magnetic fields in accordance with the description herein. Manufacturing beads (230, 110, 130, 150) via 3D printing, MIM, or PM, may also provide various other design benefits that may create geometries to improve the connection between housings (32, 34), improved the welding shiplaps, and/or improve the restraint/containment of magnets within housings (32, 34).

Figure 17:
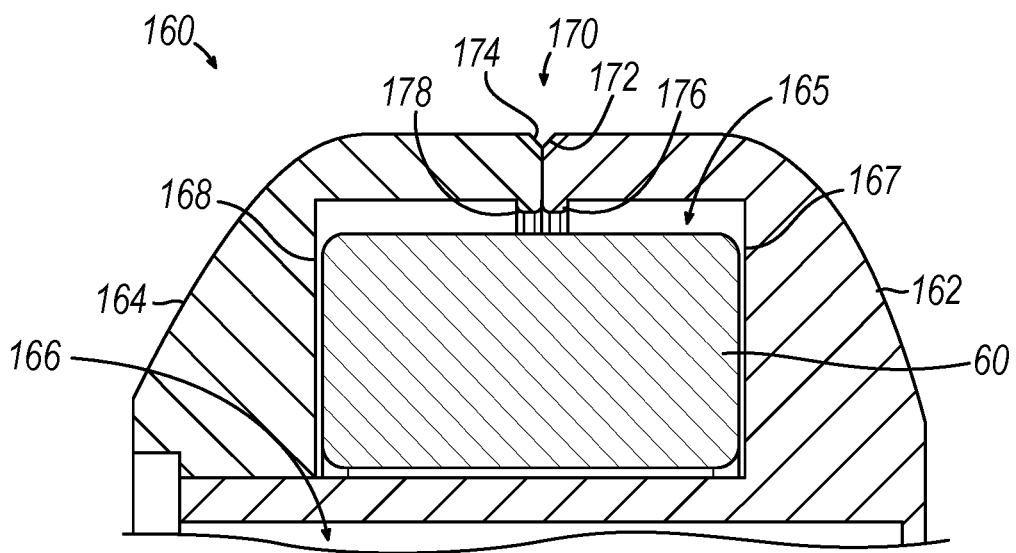
FIG. 17 depicts a cross-sectional view of a bead and a magnet that may be readily incorporated into the sphincter augmentation device of FIG. 3 or FIG. 12.

FIG. 17 shows an exemplary bead (160) manufactured with 3D printing, MIM, or PM manufacturing techniques.

Bead (160) may be formed with a magnetically inert metallic material, such as titanium or any other suitable material as would be apparent to one skilled in the art in view of the teachings herein. Bead (160) may be substantially similar to bead (30, 110, 130, 150) described above, with differences elaborated below. Therefore, bead (160) includes a pair of housings (162, 164) that may securely fasten to each other via welding. However, as shown in FIG. 17, bead (160) has not yet been welded. Housings (162, 164) may be substantially similar to housing (32, 34) described above, with differences elaborated herein.

Bead (160) defines a chamber (166), which may be substantially similar to chamber (36) of bead (30) described above. Additionally, bead (160) defines a magnet chamber (165) dimensioned to suitably house one or more magnets (60) in accordance with the description herein. Magnet chamber (165) may include any other feature dimensioned to align or constrain magnet (70, 80, 100) described herein.

Each housing (162, 164) of bead (160) includes an annular surface (167, 168) that partially defines magnet chamber (165). Annular surfaces (167, 168) are dimensioned to abut against a corresponding annular surface of magnet (60). Portions of housings (162, 164) defining magnet chamber (165), including annular surfaces (167, 168), may be 3D printed with geometric features and/or an alternative flexible material to minimize the chance of magnet (60) "floating" within magnet chamber (165) during exemplary use in accordance with the description herein. In order words, these 3D printed features may force both annular surfaces (167, 168) into engagement with corresponding annular surface of magnet (60), thereby prevent magnet (60) from shifting away from one annular surface (167, 168) and closer toward the other annular surface (167, 168) (i.e., "floating" within magnet chamber (165)). For example, such features may be similar to orientation projection (134, 154) of beads (130, 150), as those features may also prevent floating in addition to orienting magnets (120, 140). By preventing "floating," such features may firmly secure magnet (60) in magnet chamber (165), thereby preventing relative movement between magnet (60) and housings (162, 164).

Manufacturing bead (160) via 3D printing, MIM, or PM may also allow for design benefits related to improving the welding of housings (162, 164) together. When fully assembled, magnetic chamber (165) may be hermetically sealed relative to chamber (166) and an exterior of bead (160). Therefore, it may be desirable to provide a quality weld around portions of housings (162, 164) which abut against each other in order to provide a suitable hermetic seal between magnetic chamber (165) and the exterior or housings (162, 164). In the current example, bead (160) includes an improved weld joint location (170). Weld joint location (170) is formed by pair of V-groove slanted surfaces (172, 174) and corresponding flanges (176, 178) formed by respective housings (162, 164).

Flanges (176, 178) contact each other to form a butt joint such that V-groove slanted surfaces (172, 174) together define an annular V-groove around the circumference of bead (160). Flanges (176, 178) may also extend annularly around the circumference of bead (160). The annular V-groove around the circumference of bead (160) may provide a window for a weld head to provide energy to create a weld. Additionally, the annular V-groove around the circumference of bead (160) may provide a space for the top of a weld bead to fall within as housings (162, 164) are welded together. V-groove slanted surfaces (172, 174) may therefore provide for an optimized weld bead around the circumference of housing (162, 164), thereby promoting a suitable hermetic seal between magnetic chamber (165) and the exterior of housings (162, 164). Additionally, due to manufacturing bead (160) via one of the above-mentioned processes, flanges (172, 174) may be formed to contact each other at locations that extend partially into magnet chamber (165). Flanges (172, 174) extend partially into magnetic chamber (165) in order to allow for annular V-groove to be formed while also providing sufficient area of contact between housings (162, 164) without impacting the quality of the weld. Therefore, the geometries provided by 3D printing, MIM, or PM weld joint location (170) may lead to more consistent welding around the circumference of bead (160).

While in the current example, weld joint location (170) includes a pair of slanted surfaces (172, 174) to form a v-groove, weld joint location (170) may include any other suitable geometries as would be apparent to one skilled in the art in view of the teachings herein. FIGS. 18-23 show various types of geometries that may incorporated into weld joint locations forming the butt joint between housings (162, 164).

Figure 18:
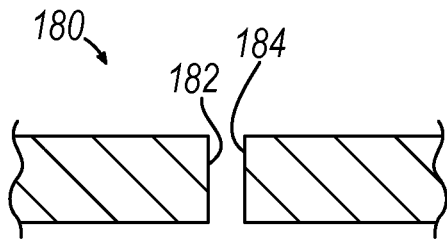
FIG. 18 depicts a cross-sectional view of an exemplary butt joint that may be incorporated into the bead of FIG. 17.

FIG. 18 shows a square butt joint weld location (180) that is formed from a first squared surface (182) that may be associated with a first bead housing and a second squared surface (184) that may be associated with a second bead housing.

Figure 19:
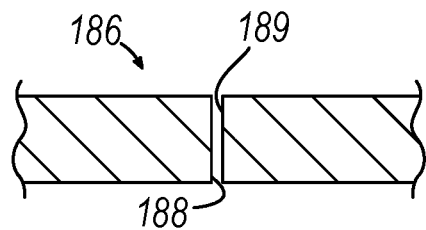
FIG. 19 depicts a cross-sectional view of another exemplary butt joint that may be incorporated into the bead of FIG. 17.

FIG. 19 shows a closed square butt joint weld location (186) formed from a first squared surface (188) that may be associated with a first bead housing and a second squared surface (189) that may be associated with a second bead housing. First and second squared surfaces (188, 189) of closed square butt joint weld location (186) are closer together compared to squared surfaces (182, 184) of FIG. 18.

Figure 20:
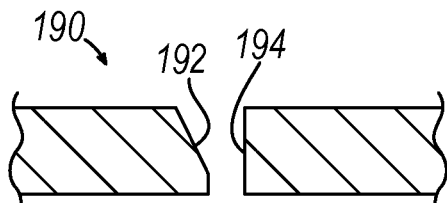
FIG. 20 depicts a cross-sectional view of another exemplary butt joint that may be incorporated into the bead of FIG. 17.

FIG. 20 shows a single-bevel butt joint weld location (190) formed from a beveled surface (192) that may be associated with a first bead housing and a square surface (194) that may be associated with a second bead housing. A surface underneath beveled surface (192) may contact square surface (194) such that bevel surface (192) and square surface (194) define a space for the top of a weld bead, similar to V-groove described above.

Figure 21:
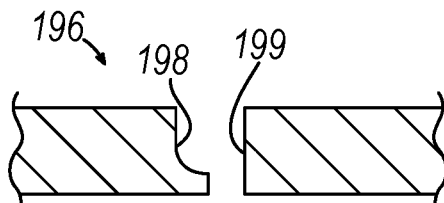
FIG. 21 depicts a cross-sectional view of another exemplary butt joint that may be incorporated into the bead of FIG. 17.

FIG. 21 shows a single-J butt joint weld location (196) formed from a concave surface (198) that may be associated with a first bead housing and a square surface (199) that may be associated with a second bead housing. A surface underneath concave surface (198) may contact square surface (199) such that concave surface (198) and square surface (199) define a space for the top of a weld bead, similar to V-groove described above.

Figure 22:
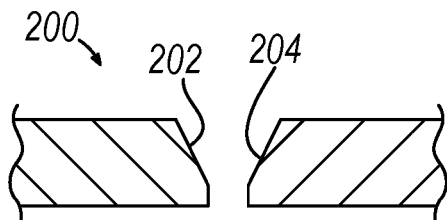
FIG. 22 depicts a cross-sectional view of another exemplary butt joint that may be incorporated into the bead of FIG. 17.

FIG. 22 shows a single-V butt joint weld location (200) formed form a first bevel surface (202) that may be associated with a first bead housing and a second bevel surface (204) that may be associated with a second bead housing. Surfaces (202, 204) may define a space for the top of a weld bead, similar to V-groove described above.

Figure 23:
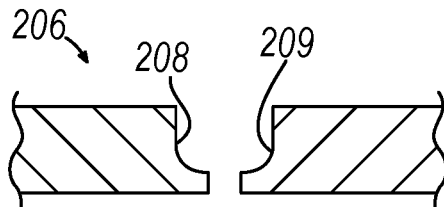
FIG. 23 depicts a cross-sectional view of another exemplary butt joint that may be incorporated into the bead of FIG. 17.

FIG. 23 shows a single-U butt joint weld location (206) formed from a first concave surface (208) that may be associated with a first bead housing and a second concave surface (209) that may be associated with a second bead housing. Surfaces (208, 209) may define a space for the top of a weld bead, similar to V-groove described above.

Figure 24:
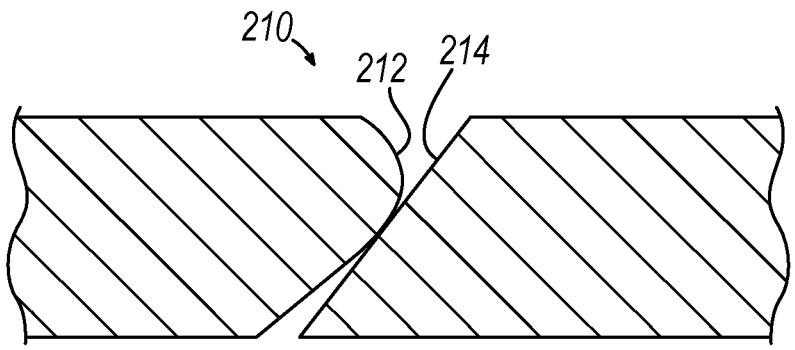
FIG. 24 depicts a cross-sectional view of another exemplary butt joint that may be incorporated into the bead of FIG. 17.

FIG. 24 shows a bevel-arched butt joint weld location (210) formed from a convex surface (212) that may be associated with a first bead housing and a bevel surface (214) that may be associated with a second bead housing.

Surfaces (212, 214) may define a space for the top of a weld bead, similar to V-groove described above.

In some instances, after suitably placing housings (62, 64, 162, 164) adjacent to each other for welding, but prior to welding, it may be desirable to inhibit housings (62, 64, 162, 164) from moving relative to each other such that during welding, housings (62, 64, 162, 164) do not unintentionally move relative to each other.

Figure 25A:
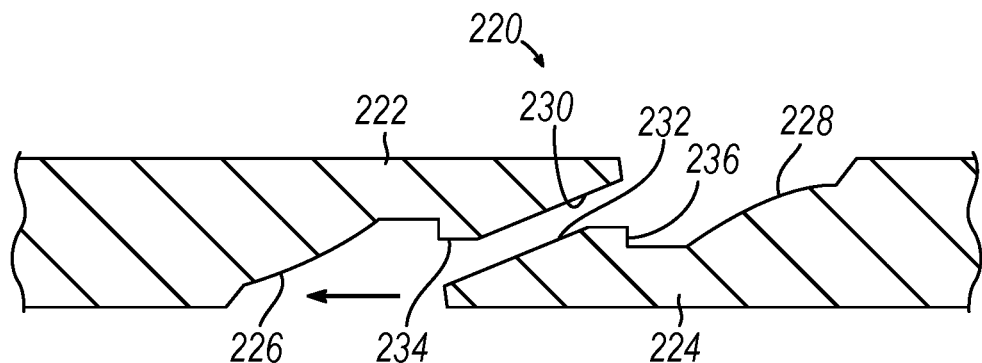
FIG. 25A depicts a cross-sectional view of an exemplary latching joint that may be incorporated into the bead of FIG. 17, where the latching joint is in a decoupled position.
Figure 25B:
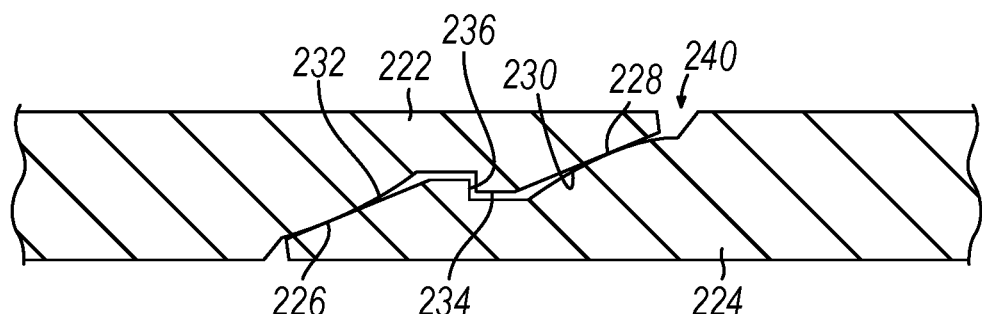
FIG. 25B depicts a cross-sectional view of the latching joint of FIG. 25A in a coupled position prior to welding.
Figure 25C:
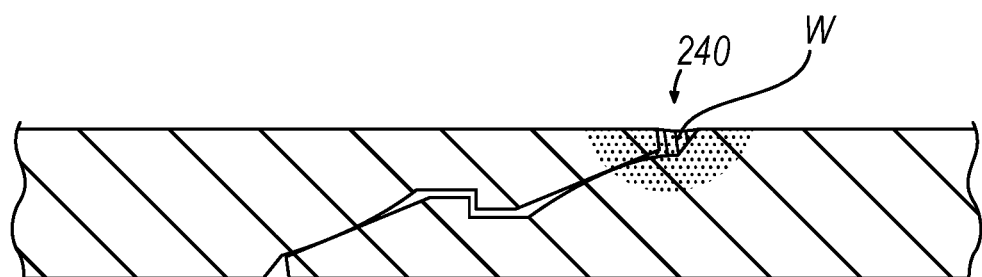
FIG. 25C depicts a cross-sectional view of the latching joint of FIG. 25A welded together in the coupled position.

FIGS. 25A-25C show an exemplary latching weld location (220) that may be readily incorporated into housings (162, 164) in replacement of weld joint location (170) described above. Latching weld location (220) includes a first latch member (222) that may be associated with first housing (162) and a second latch member (224) that may be associated with a second housing (164). Latch members (222, 224) may extend annularly around the perimeter of housings (162, 164). As will be described in greater detail below, latch members (222, 224) are configured to couple together in order to inhibit housings (162, 164) from unintentionally moving relative to each other during the welding process.

Each latch member (222, 224) includes a respective convex surface (226, 228), an angled surface (230, 232), and a latch element (234, 236). During initial coupling of first latch member (222) with second latch member (224), angled surfaces (230, 232) may be suitably aligned as shown in FIG. 25A. Next, latch members (222, 224) may be driven toward to each other such that angled surfaces (230, 232) suitably engage each other. Engagement between angled surfaces (230, 232) may cause latch members (222, 224) to resiliently flex away from each other until latch members (222, 224) reach the position in FIG. 25B. With angled surfaces (230, 232) no longer in contact with each other, the resilient nature of latch members (222, 224) may allow latch members (22, 224) to return to the relaxed position as shown in FIG. 25B.

At the moment shown in FIG. 25B, latching weld location (220) may be sufficiently latched such that engagement between angled surfaces (230, 232) and convex surfaces (228, 226) may prevent inadvertent deflection of annular latching members (222, 224) relative to each other. Therefore, housings (162, 164) may also be inhibited form moving relative to each other. Additionally, engagement between latch elements (234, 236) may also prevent inadvertent decoupling of latch members (222, 224) in the axial direction (i.e., the opposite direction as shown in the arrow of FIG. 25A). Latching members (222, 224) may also be dimensioned to define an annular weld groove (240), similar to v-groove described above. Therefore, as shown in FIG. 25C, with latching weld location (240) suitably formed, an annular weld (W) may be formed to fix latch members (222, 224) relative to each other at weld location (240). Of course, any other suitable kind of weld bead receiving groove or space may be defined at latching weld location (240), such that latching weld location (240) need not necessarily define a V-shaped groove.

In some instances, it may be desirable to not only inhibit movement between housings (162, 164) prior to and during welding, but it may also be desirable to ensure housings (162, 164) initially couple to each other in a predetermined orientation. FIG. 26 shows an exemplary bead (250) that includes a first housing (252) and a second housing (254) that are configured to latch together at a predetermined orientation prior to welding. Bead (250) may be substantially similar to bead (30, 110, 130, 150, 160) described above, with differences elaborated below. Bead (250) may be manufactured utilizing 3D printing, MIM, or PM manufacturing means; or using any other suitable manufacturing process. Housings (252, 254) are configured to couple together in order to form an annular weld location (260) that surrounds a perimeter of bead (250).

As best seen in FIG. 27, first housing (252) includes an outer offset ledge (262), an inner projection (266) extending away from outer offset surface (262), and a complementary detent (270) located on an outer surface of inner projection (266). As best seen in FIG. 28, second housing (254) includes an inner offset ledge (264), an outer projection (268) extending away from inner offset ledge (264), and a complementary recess (272) defined by an inner surface of outer projection (268). As best shown in FIG. 26, inner projection (266) is dimensioned to fit within the space defined by outer projection (268) and inner ledge (264); while outer projection (268) is dimensioned to fit within the space defined by inner projection (266) and outer ledge (262).

The outer surface of inner projection (266) and the inner surface of outer projection (268) are dimensioned to be directly adjacent to each other when housings (252, 254) are suitably coupled. Additionally, when suitably aligned, complementary detent (270) is dimensioned to snap-fit within complementary recess (272), thereby inhibiting first housing (252) from moving relative to second housing (254). Detent (270) and recess (272) are strategically located on respective surfaces of projections (266, 268) such that housings (252, 254) couple with each other in a snap-fit relationship at a predetermined orientation. Therefore, during initial assembly, housings (252, 254) may only be snap-fit coupled at a predetermined orientation relative to each other prior to welding. Once coupled with each other, annular weld location (260) may be welded in accordance with the description herein. Annular weld location (260) may also define an annular weld groove similar to any of the weld grooves described above. While in the current example, detent (270) and recess (272) are used to couple housings (252, 254) in a snap-fit manner, any other suitable means may be used to couple housings (252, 254) together in a predetermined orientation while also inhibiting movement of housings (252, 254) relative to each other prior to welding. For example, a friction fitting relationship may be used to coupled housings (252, 254).

As mentioned above, housings (32, 34) define openings (33, 35) configured to allow wire (42) of links (40) to slide through openings (33, 35); thereby allowing beads (30) to slide along links (40) through a restricted range of motion. In other words, openings (33, 35) are sized accommodate movement of beads (30) relative to links (40) such that device (20) may transition between the expanded state and the contracted state in accordance with the description herein.

However, housings (32, 34) of FIGS. 3-5B define openings (33, 35) in such a way that the contact between surfaces of link (40) and surfaces defining openings (33, 35) as beads (30) slide along the restricted range of motion are not controlled. In other words, as device (20) transitions between the contracted state (see, e.g., FIG. 5B) and the expanded state (see, e.g., FIG. 5A), a single link (40) may contact a first portion of a surface defining opening (33, 35) during one expansion or retraction (e.g., during a first instance of the patient swallowing), and then contact a second portion of the surface defining opening (33, 35) during a second expansion or retraction (e.g., during a second instance of the patient swallowing), which may result in inconsistent transitions between the contracted and expanded state. Additionally, it may be desirable to further ensure that ball tips (44) do not undesirably exit housing (32, 34) via openings (33, 35) during use.

FIGS. 29-32 show various housings (280, 290, 300, 310) that may be readily incorporated into bead (30, 110, 130, 150, 160, 250) described above. Housings (280, 290, 300, 310) may be 3D printed, which may provide for the ability to create the various geometries described herein. Each housing (280, 290, 300, 310) is substantially similar to housing (32, 34, 162, 164, 152, 154) described above, with differences elaborated below. In particular, each housing (280, 290, 300, 310) defines an opening (282, 292, 302, 312) dimensioned to influence the contact locations between wire (42) and the portion of housing (280, 290, 300, 310) defining opening (282, 292, 302, 312). Each opening (282, 292, 302, 312) is also dimensioned to reduce the size of openings (282, 292, 302, 312) to thereby reduce the chances that ball tip (44) undesirably exits housing (280, 290, 300, 310) via openings (282, 292, 302, 312).

Figure 29:
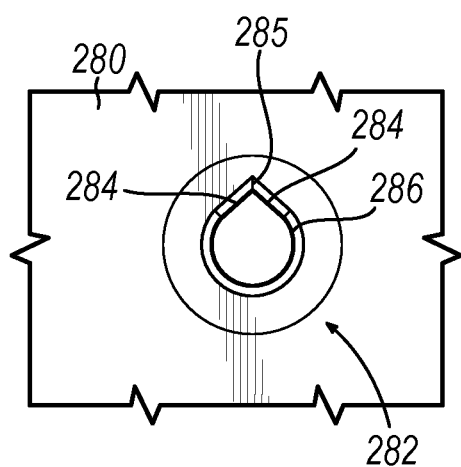
FIG. 29 depicts an elevated front view of an exemplary housing that may be used to form an exemplary bead of the sphincter augmentation device of FIG. 3 or FIG. 12.

Turning to FIG. 29, housing (280) defines a teardrop opening (282) defined by an arched surface (286) extending into a pair of guide surfaces (284) that together terminate into a targeted contact location (285). As housing (280) moves relative to link (40) in order to allow device (20, 115) to expand and contract in accordance with the description herein, guide surfaces (284) are positioned to contact wire (42) of link (40) to thereby influence wire (42) to actuate toward targeted contact location (285). Therefore, guide surfaces (284) and contact location (285) are configured to influence to locations of contact between links (40) and teardrop opening (282) to thereby help provide for more consistent transitions of device (20, 115) between the expanded state and the contracted state in accordance with the description herein. Additionally, the geometry of teardrop opening (282) may further resist or inhibit ball tip (44) from exiting housing (280).

Figure 30:
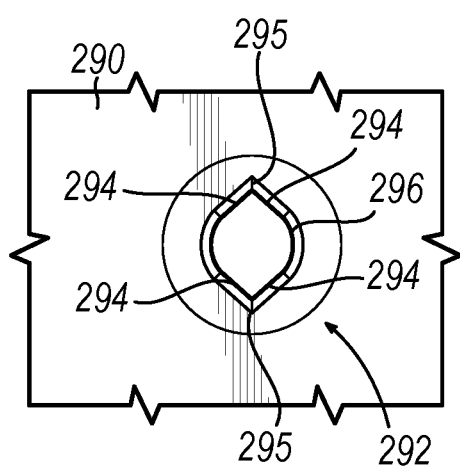
FIG. 30 depicts a front elevation view of another exemplary housing that may be used to form an exemplary bead of the sphincter augmentation device of FIG. 3 or FIG. 12.

Turning to FIG. 30, housing (290) defines a double teardrop opening (292) defined by a pair of arched surfaces (296) extending at each end into a guide surface (294) that together terminate into a respective targeted contact location (295) located on opposite ends of each other. As housing (290) moves relative to link (40) in order to allow device (20, 115) to expand and contract in accordance with the description herein, guide surfaces (294) are positioned to contact wire (42) of link (40) to thereby influence wire (42) to actuate toward a respective targeted contact location (295). Therefore, guide surfaces (294) and contact location (295) are configured to influence to locations of contact between links (40) and double teardrop opening (292) to thereby help provide for more consistent transitions of device (20, 115) between the expanded state and the contracted state in accordance with the description herein. Additionally, the geometry of double teardrop opening (292) may further resist or inhibit ball tip (44) from exiting housing (290).

Figure 31:
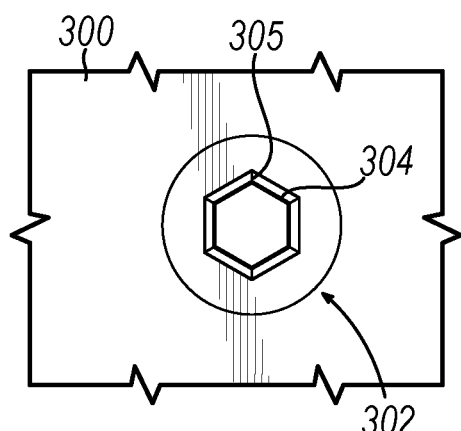
FIG. 31 depicts a front elevation view of another exemplary housing that may be used to form an exemplary bead of the sphincter augmentation device of FIG. 3 or FIG. 12.

Turning to FIG. 31, housing (300) defines a hexagonal opening (302) defined by six guide surfaces (304) that all terminate into a pair of targeted contact locations (305). As housing (300) moves relative to link (40) in order to allow device (20, 115) to expand and contract in accordance with the description herein, guide surfaces (304) are positioned to contact wire (42) of link (40) to thereby influence wire (42) to actuate toward a respective targeted contact location (305). Therefore, guide surfaces (304) and contact location (305) are configured to influence to locations of contact between links (40) and hexagonal opening (302) to thereby help provide for more consistent transitions of device (20, 115) between the expanded state and the contracted state in accordance with the description herein. Additionally, the geometry of hexagonal opening (302) may further resist or inhibit ball tip (44) from exiting housing (300).

Figure 32:
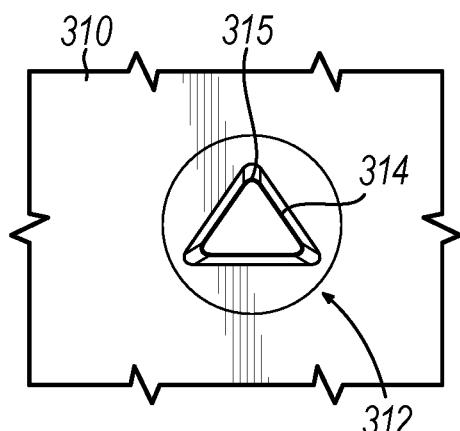
FIG. 32 depicts a front elevation view of another exemplary housing that may be used to form an exemplary bead of the sphincter augmentation device of FIG. 3 or FIG. 12.

Turning to FIG. 32, housing (310) defines a triangular opening (312) defined by a three guide surfaces (314) that all terminate into a pair of targeted contact locations (315). As housing (310) moves relative to link (40) in order to allow device (20, 115) to expand and contract in accordance with the description herein, guide surfaces (314) are positioned to contact wire (42) of link (40) to thereby influence wire (42) to actuate toward a respective targeted contact location (315). Therefore, guide surfaces (314) and contact location (315) are configured to influence to locations of contact between links (40) and triangular opening (312) to thereby help provide for more consistent transitions of device (20, 115) between the expanded state and the contracted state in accordance with the description herein. Additionally, the geometry of triangular opening (312) may further resist or inhibit ball tip (44) from exiting housing (310).

IV. Example of Housing with Integrated Holding, Aligning, or Clamping Features

As mentioned above, when bead (30) is being assembled, housings (32, 34) may be placed adjacent to each other, thereby forming a butt joint, and welded together in order to suitably secure housings (32, 34) together. While housings (32, 34) are being welded together, the geometric shape of housings (32, 34) may become distorted for various reasons that would be apparent to one skilled in the art in view of the teachings herein. Some reasons for geometric distortion of housings (32, 34) may include non-uniform expansion and contraction of housings (32, 34) due to plastic thermal strain as housings (32, 34) undergo heating and cooling cycles during the welding process. If the geometric shape of housings (32, 34) becomes too distorted, the contact zones between adjacent beads (30) in device (20), while in the contracted position (see FIG. 5B), may also deviate. Deviation of contact zones between adjacent beads (30) may result in an undesirable shift of the generated magnetic fields and attraction/separation forces between magnets (60); which may in turn contribute to implant (20) not properly functioning.

Therefore, it may be desirable to control and/or minimize any type of distortion of housings (32, 34) during the welding process by providing holding, aligning, or clamping features integrated into one or both housings (32, 34) that enable more uniform compression while clamping housings (32, 34) during welding to thereby improve assembly. One way to improve uniform compression while clamping housings (32, 34) may be to align housings (32, 34) in a defined orientation or location when mating with each other.

Figure 33:
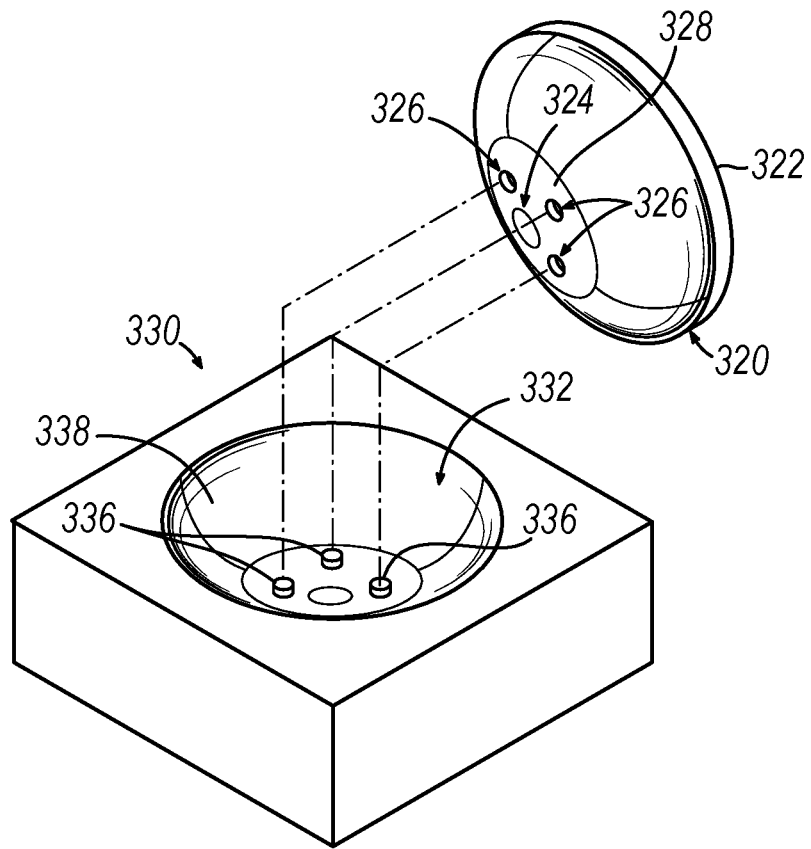
FIG. 33 depicts a perspective view of an exemplary housing decoupled from an exemplary mating plate that may be used in conjunction with a corresponding housing and mating plate in order to weld housings together.

FIG. 33 shows an exemplary housing (320) that may be substantially similar to housings (32, 34, 130, 162, 164, 252, 254, 280, 290, 300, 310) described above with differences elaborated below. Housing (320) includes an annular flange/weld location (322) configured to form a butt joint with another suitable housing (320) such that housings (320) may be welded together in accordance with the description herein. Housing defines an opening (324) that may be substantially similar to openings (33, 35) described above.

Housing (320) also includes an exterior surface (328) that includes integrated mounting plate interface features (326), such recessed surfaces. Integrated mounting plate interface features (326) are on a portion of exterior surface (328) extending on a plane that is parallel with the weld plane of annular weld location (322). Mounting plate interface features (326) are configured to mate with complementary interface features (336) of a mounting plate (330) such that while suitably coupled, housing (320) is rotationally constrained relative to mounting plate (330) along a plane that is parallel with the weld plane of annular weld location (322). Additionally, interface features (326, 336) are dimensioned such that housing (320) couples with mounting plate (330) at predetermined orientations.

Figure 34:
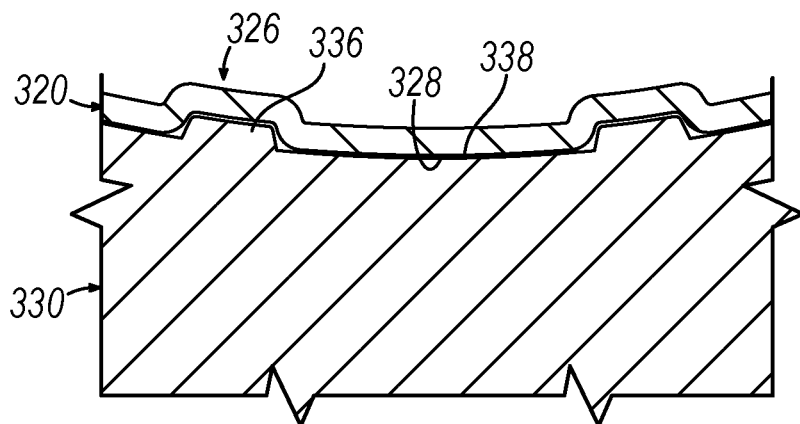
FIG. 34 depicts a cross-sectional view of the housing and mating plate of FIG. 33 coupled together.

Mounting plate (330) defines an opening (332) dimensioned to suitably contain housing (320) in preparation of welding a pair of complementary housings (320) to form a suitable bead in accordance with the description herein. Mounting plate (330) includes a complementary surface (338) that at least partially defines opening (332). Additionally, mounting plate (330) includes complementary housing interface features (336), such as projections/dimples, dimensioned to couple with interface feature (326) of housing (320) when suitably coupled. As best shown in FIG. 34, when housing (320) is coupled with mounting plate (330), complementary surface (338) engages corresponding portions of exterior surface (328) of housing (320); while interface features (326, 336) are suitably coupled with each other.

As mentioned above, interface features (326, 336) are dimensioned such that housing (320) couples with mounting plate (330) at a predetermined orientation. Therefore, during assembly, a first housing (320) may be suitably coupled with a first mating plate (330); while a second housing (320) may be suitably coupled with a second mating plate (330). Both mating plates (330) may then be suitably aligned and stacked on top of each other such that annular weld locations (322) of each housing (320) are suitably compressed against each other. Mounting plates (330) may be suitably aligned with each other using any suitable means as would be apparent to one killed in the art in view of the teachings herein. For example, mounting plates (330) may be aligned such that edges of each mounting plate (330) are substantially flush with one another. Since each housing (320) is coupled with a respective mounting plate (330) at a predetermined orientation, housings (320) may also be aligned with each other in a predefined orientation or location once mounting plates (330) are suitably aligned. Such alignment may lead to more uniform compression of clamping both housings (320) together. Additionally, since mounting plate (330) includes a complementary surface (338) engaging exterior surface (328) of a respective housing (320), such uniform engagement may also lead to more uniform compression of clamping of both housings (320).

In the current example, interface features (326) of housing (320) are circular recesses defined by exterior surface (328). However, interface features (326) may have any other suitable geometry as would be apparent to one skilled in the art in view of the teachings herein, such as a D-shaped recess, a cylindrical protrusion, a bump, etc. In the current example, interface features (326) are disposed on exterior surface (328) in a symmetrical manner. However, this is merely optional, as features (326) may be disposed in a non-symmetrical manner as well. Mounting plate interface feature (326) may be uniquely sized/shaped compared to each other such that interface features (326) only fit within a single corresponding complementary interface feature (336) of mounting plate. Therefore, in some instances, housing (320) may only couple with mounting plate interface feature (326) in a predetermined orientation.

Figure 35:
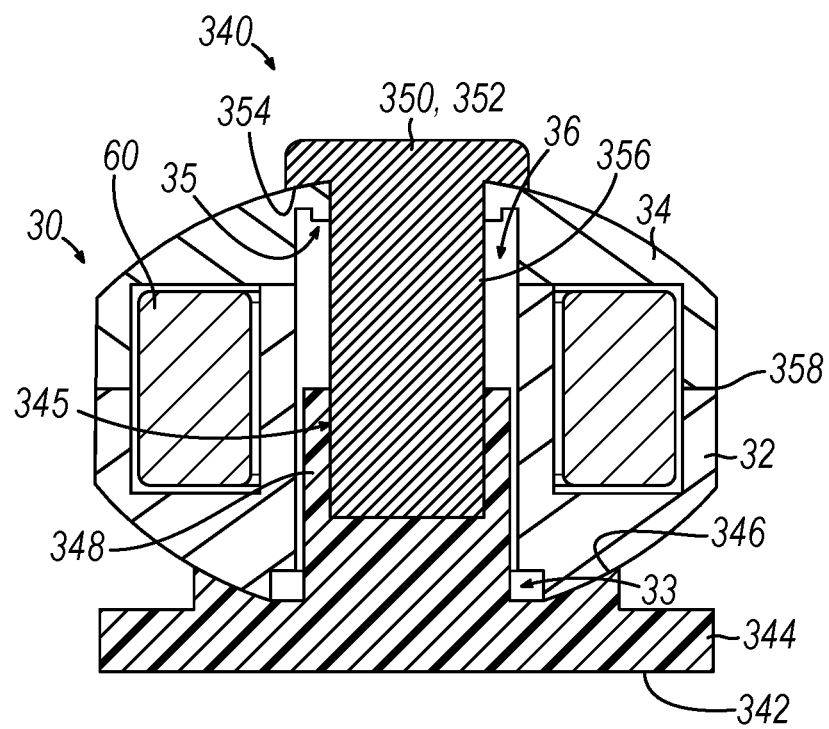
FIG. 35 depicts a cross-sectional view of housing of a bead being compressed together by an exemplary compression jig assembly.

FIG. 35 shows contact pressure jig assembly (340) that may be used in order to suitably align housings (32, 34) of bead (30) during assembly in order to provide a more uniform compression of housings (32, 34) during welding. Contact pressure jig assembly (340) includes a first jig (342) and a second jig (350) configured to compress housing (32, 34) against each other to provide an aligned annular weld location (358).

First jig (342) includes a base (344) having a complementary housing surface (346), and an alignment post (348) defining a recessed opening (345). Complementary housing surface (346) is dimensioned to receive a corresponding portion of housing (32) such that surface (346) is substantially flush with the corresponding portion of housing (32). Therefore, when compressed against each other in accordance with the description herein, surface (346) and housing (32) cooperatively align the orientation of housing (32) relative to first jig (342). Alignment post (348) is dimensioned to fit through opening (33) while surface (346) and corresponding portion of housing (32) are suitably engaged with each other.

Second jig (350) includes a base (352) having a complementary housing surface (354), and an alignment post (356) dimensioned to fit within the recessed openings (345) of alignment post (348) of first jig (342). Complementary housing surface (354) is dimensioned to receive a corresponding portion of housing (34) such that surface (354) is substantially flush with the corresponding portion of housing (34). Therefore, when compressed against each other in accordance with the description herein, surface (354) and housing (34) cooperatively align the orientation of housing (34) relative to second jig (350).

Complementary surfaces (346, 354) are dimensioned to cooperatively compress housings (32, 34) against each other. Therefore, the compression provided by complemented surfaces (346, 354) coming together also helps align a respective complementary surface (346, 354) with their respective housing (32, 34).

Recessed opening (345) of alignment post (348) of first jig (342) is dimensioned to receive an alignment post (356) of second jig (350). Alignment posts (356) of second jig (350) and recessed opening (345) are dimensioned such that when alignment post (356) is housed within recessed opening (345), first jig (342) and second jig (350) are suitably aligned with each other. Since complementary of surfaces (346, 354) of jigs (342, 350) engage the corresponding surfaces housings (32, 34) under compression to cooperatively algin the orientation of housings (32, 34) relative to jigs (342, 350); the alignment of first jig (342) and second jig (350) via alignment posts (348, 356) also aligns housings (32, 34) relative to each other in order to provide a consistently aligned butt joint at annular weld location (358). Additionally, since jigs (342, 350) include complementary surfaces (346, 354) that engage exterior surfaces of respective housings (32, 34), such uniform engagement may also lead to more uniform compression of clamping both housings (32, 34).

While jig assembly (340) is shown being used with housings (32, 34), it should be understood that jig assembly (340) may also include features similar to mounting plate (330) such that jig assembly (340) may be used within housings (320) described above.

In some instances, it may be desirable to have a material or feature placed along portions of housing (32, 34) forming annular weld locations. For instance, housings (32, 34) could have crush ribs and/or other press-fit features that would allow housings (32, 34) to be pressed together to create a restraining hold. Then the perimeter weld could be a fast, low depth weld to ensure a hermetic seal without having to also actively hold the housings (32, 34) together during the welding process. In some versions, if the press joining includes a radial small lip near the base of the flange, the press fit may create the hermetic seal without requiring a weld.

In some instances, it may be desirable to have alternative weld geometry that allows for full perimeter welding/sealing. Such geometries could combine housing (34) and a cap into one piece. The central channel (e.g., chamber (36)) could be created so that it is somewhat recessed, and the two adjacent interconnection ball tips (44) are contained in separate holes in the same central plate. The surface around the central plate could have a 45-degree (or otherwise angled) conical surface that mates with the adjacent surface with a slightly different conical receiving angle. The housings (32, 34) could be pressed together, mating the angular surfaces together and creating a pressure sealing surface. Once the perimeter weld is done, the inside surface may be permanently held in a gas pressure fitted state, reducing the number of welds needed to the outer diameter perimeter weld (e.g., the annular weld location (358)).

V. Example of 3D Printed or Metal Injection Molding (Mim) Unibody Housing

Figure 36:
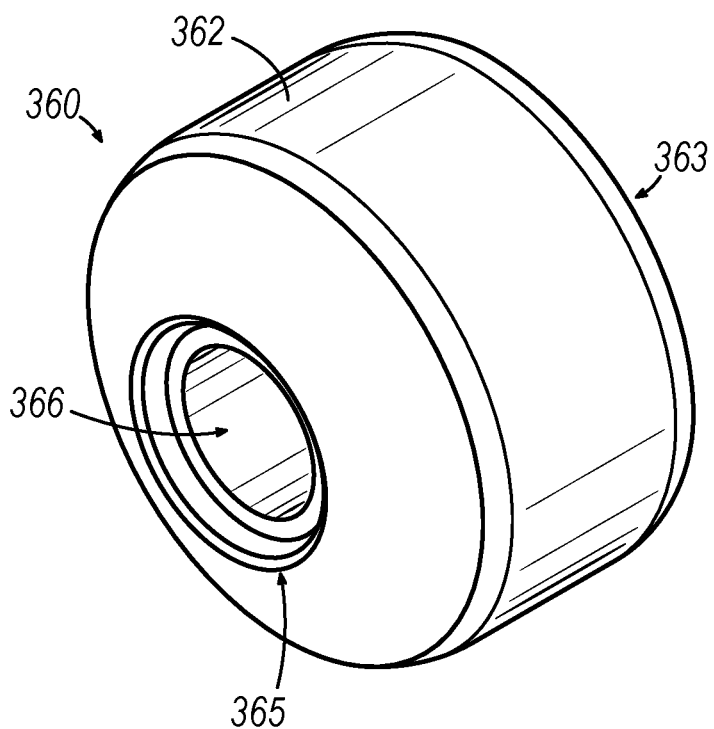
FIG. 36 depicts a perspective view of an exemplary bead having a unibody housing.

As mentioned above, welding housings (32, 34) together may create undesirable distortions, which may in turn lead to undesirable operation of implant (20). Therefore, in some instances, it may be desirable to create a bead formed from a unibody housing that does not require any welding. FIG. 36 shows an exemplary bead (360) that includes a 3D printed unibody housing (362) configured to suitably house a magnet (372) (see FIGS. 37C-37D). Magnet (372) may be substantially similar to magnet (60) described above, except magnet (372) also includes an orientation body (374) that is substantially similar to orientation body (106) described above.

As will be described in greater detail below, unibody housing (362) is 3D printed such that it does not require assembly via welding, thereby eliminating the formation of any weld beads. As will also be described in greater detail below, during the manufacturing process of bead, the 3D printing of unibody housing (362) may be temporarily delayed in order to assemble magnet (372) into housing (362), as well as links (40) if desired.

Figure 37A:
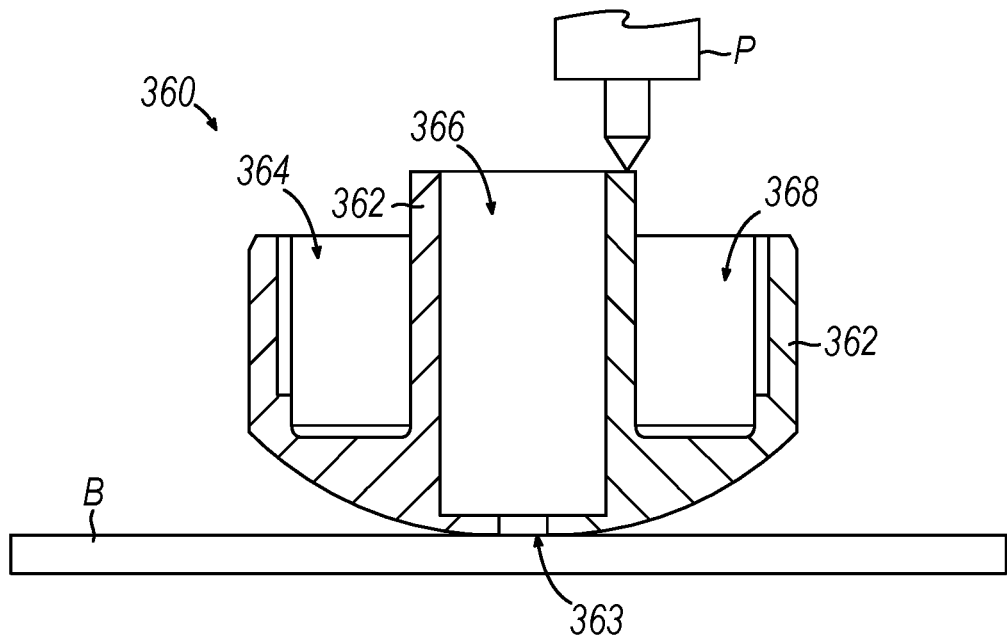
FIG. 37A depicts a cross-sectional view of a 3D printer partially printing a unibody bead that may be readily incorporated into the sphincter augmentation device of FIG. 3 or FIG. 12.
Figure 37B:
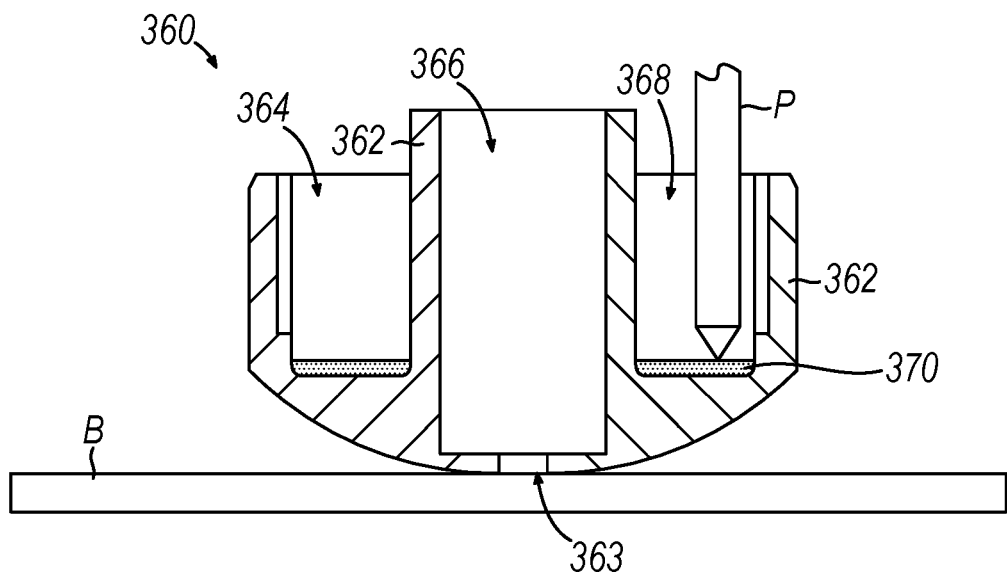
FIG. 37B depicts a cross-sectional view of the unibody bead of FIG. 37A, with the 3D printer printing an epoxy surface.
Figure 37C:
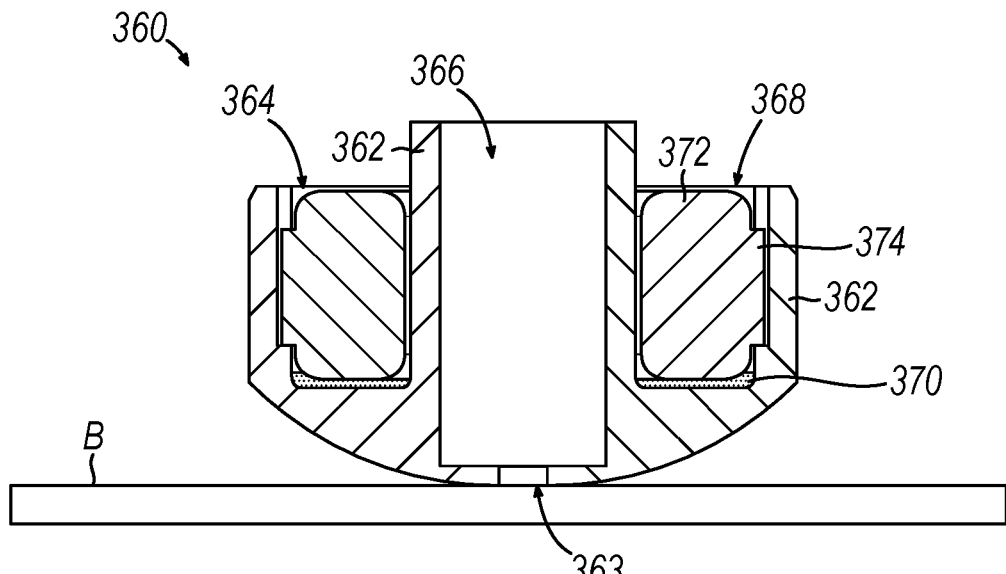
FIG. 37C depicts a cross-sectional view of the unibody bead of FIG. 37A, with a magnet inserted into a magnetic housing chamber.
Figure 37D:
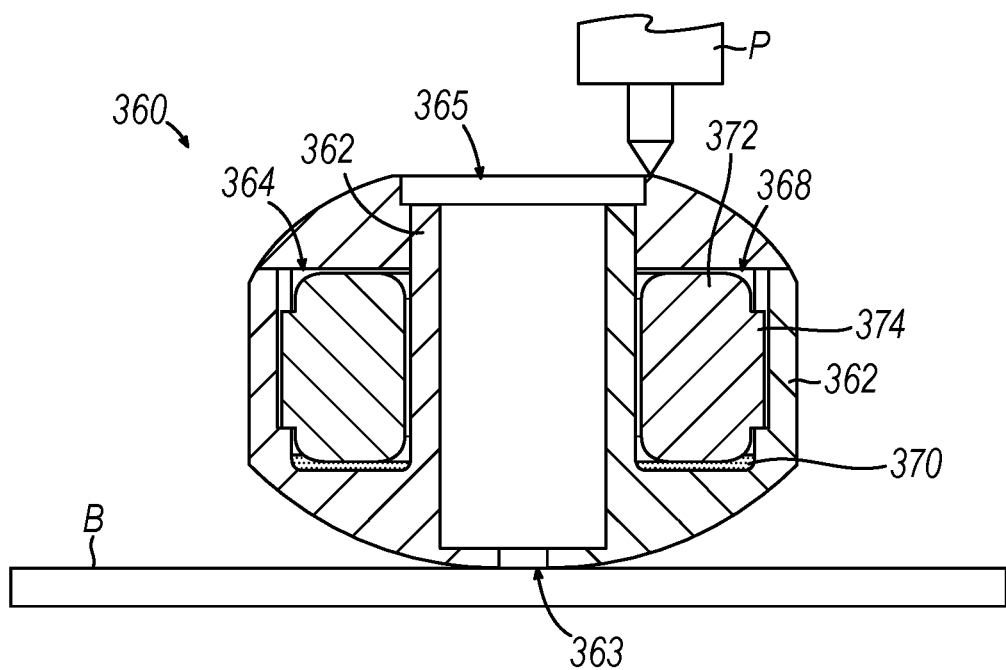
FIG. 37D depicts a cross-sectional view of the unibody bead of FIG. 37A fully printed such that the magnet of FIG. 37C is encapsulated by the unibody bead.

Turning to FIGS. 36-37D, bead (360) includes 3D printed unibody housing (362) that defines a chamber (366) extending between openings (363, 365), and a magnet housing chamber (368). Unibody housing (362) may be 3D printed out of any suitable material, such as titanium. Chamber (366) and openings (363, 365) are substantially similar to chamber (36) and openings (33, 35) described above, except a unitary housing (362) forms both openings (363, 365) rather than openings (33, 35) being formed by a respective housing (32, 34). Additionally, magnet housing chamber (368) is substantially similar to magnet housing chamber (112) described above, with differences elaborated below. Therefore, magnetic housing chamber (368) also includes an orientation slot (364), which is substantially similar to orientation slot (116) describe above. Magnet housing chamber (368) is dimensioned to receive magnet (372) such that orientation slot (364) receives orientation body (374). Therefore, magnet housing chamber (368) is configured to receive magnet (372) in a predefined angular orientation; and to prevent magnet (372) from rotating within magnet housing chamber (368) during use in accordance with the description herein.

FIGS. 37A-37D show an exemplary process of manufacturing of bead (360). First, as shown in FIG. 37A, a first portion of 3D printed unibody housing (362) may be printed on a print base (B) via 3D printer (P). Next, the 3D printing of unibody housing may temporarily stop. The first portion of unibody housing (362) printed, as shown in FIG. 37A, defines a sufficient portion of magnet housing chamber (368) to render the first printed portion of housing (362) suitable to initially house and support magnet (372).

However, as shown in FIG. 37B, prior to inserting magnet (372) within magnet housing chamber (368), 3D printer may print an epoxy filled annular face (370) at an end of magnet housing chamber (368) adjacent to opening (363). While in the current example, epoxy filled annular face (370) is 3D printed, epoxy filled annular face (370) may be installed utilizing any other suitable techniques as would be apparent to one skilled in the art. While the current example shows epoxy filled annular face (370) being installed only on one side of magnet housing chamber (368), it should be understood epoxy filled annular face (370) may be used on both ends of magnet housing chamber (368) (i.e., next to opening (365) as well). In some instances, no epoxy filled annular face (370) is used. Epoxy filled annular face (370) may be formed with any suitable material as would be apparent to one skilled in the art in view of the teachings herein. For example, epoxy filled annular face (370) may be formed of an epoxy resin used in 3D printing.

Epoxy filled annular face (370) may be used to control the spacing of magnets (372) in adjacent beads (360) of device, thereby allowing greater control of the direction and intensity of generated magnetic fields between beads (360), which may improve the homogenous spacing of magnet beads (360) in the expanded state (as exemplified in FIG. 5A). For example, as shown in FIG. 38, a first bead (360A) and a second bead (360B) may have magnets (372A, 372B) of differing magnetic strength. Therefore, it may be desirable to have an epoxy filled annular face (370A) of a first thickness ($e_A$), while a second bead (360B) may have an epoxy filled annular face (370A) of a second thickness ($e_B$). Thicknesses ($e_A$, $e_B$) may be determined based on the magnetic strength of individual magnets (372A, 372B) such that the magnetic force ($F_A$, $F_B$) generated by different magnets (372A, 372B) have substantially the same tesla value at a predetermined distance (d) from each bead (360A, 360B).

Next, with 3D printing temporarily paused, as shown in FIG. 37C, magnet (372) may be placed within magnet housing chamber (368) such that orientation bodies (374) of magnet (372) are suitably housed within orientation slots (364). In some versions, magnet (372) comprises a preformed magnet that is simply inserted in magnet housing chamber (368). In some other versions, magnet (372) is 3D printed in magnet housing chamber (368). In either scenario, once magnet (372) is housed within magnet housing chamber (368), 3D printer (P) may resume printing unibody housing (362) until completion as shown in FIG. 37D. It should be understood that with unibody housing (362) being 3D printed with a temporary pause in order to insert magnet (372) within magnet housing chamber (368), bead (360) may be manufactured such that magnet housing chamber (368) is hermetically sealed from an external environment without welding portions of bead (360) together. Therefore, magnet housing chamber (368) is hermetically sealed from chamber (366) extending between openings (363, 365) and external surfaces of unibody housing (362). Eliminating the requirement of welding portions of bead (360) together may increase the accuracy and precision of the dimensions of unibody housing (362) while also protecting magnet (372) from fluids/other matter while functioning in accordance with the description herein.

In some instances, it may be desirable to intermittently pause 3D printing of housing (362) in order to suitably place links (40) into chamber (366). Such pausing and resuming of 3D printing housing (362) may be done such that links (40) are slidably contained within chamber (366) in similar fashion as links (40) are slidably contained within chamber (36) of bead (30) described above. Opening (363) located adjacent to print base (B) may be formed as part of the 3D printing process (e.g., by not depositing material in the region of opening (363)). Therefore, a plate of other link-retaining feature does not necessarily need to be incorporated into that end of bead (360) during assembly. It should be understood that the manufacturing process may differ at the other end of bead (360). For example, opening (365) may be relatively larger compared to opening (363) such that a link retention plate (not shown) secured at opening (365) in order to retain a corresponding link (40) in accordance with the description herein. Such a link retention plate may be secured to housing (362) using any suitable techniques, including but not limited to using welding, press-fitting, adhesive, etc.

VI. Example of Interconnected Encasement of Magnetic Elements

As mentioned above, in some instance, magnets (60) are stacked on top of each other in a single bead (30) (see FIG. 4). In some instances, it may be desirable to improve the handling of magnets (60) during the assembly of device (20). For example, after magnets (60) are stacked on top of each other, it may be desirable to inhibit the stacked formation of magnets (60) from inadvertently magnetically reacting/attaching with other magnetic elements. Additionally, it may be desirable to enable the stacked formation of magnets (60) to be more easily handled during the magnetization process. Additionally, it may be desirable to seal magnets (60) from their environment.

Figure 39:
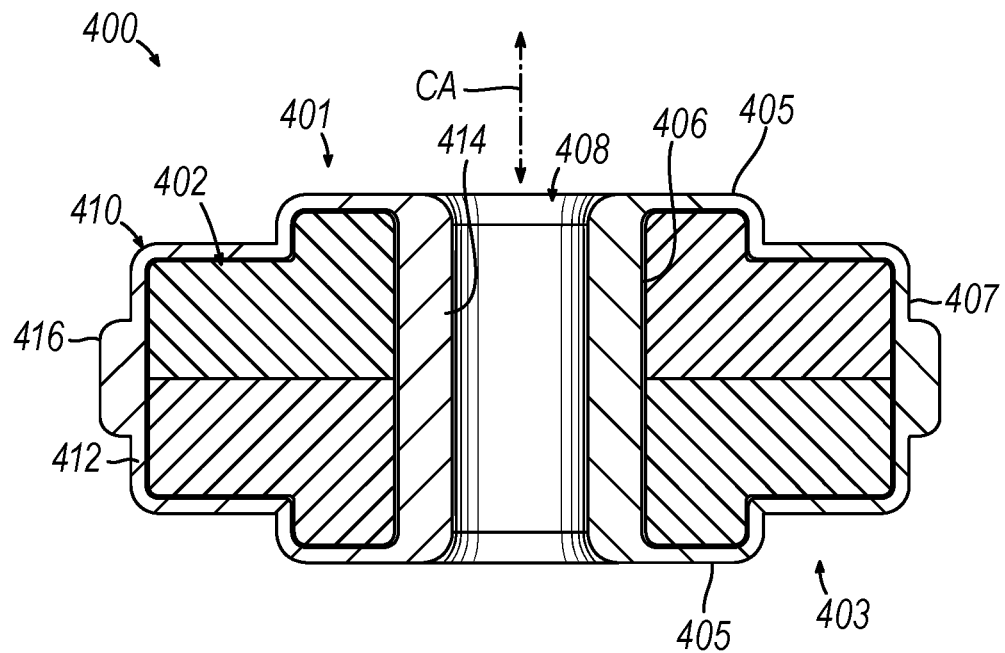
FIG. 39 depicts a cross-sectional view of an alternative magnetic assembly having an encasement molding surrounding an annular magnet.

FIG. 39 shows an exemplary magnet assembly (400) that includes an annular magnetic body (402) and an encasement molding (410) surrounding the exterior of magnetic body (402). Magnet assembly (400) may be readily incorporated into beads (30, 110, 160, 250, 360) in replacement of any of the other magnets or magnet assemblies described herein. As will be described in greater detail below, encasement molding (410) is configured to promote easier handling of magnetic body (402) during the assembly process of device (20). As will also be described in greater detail below, encasement molding (410) may also include various features that may promote proper alignment and/or inhibit undesirable movement of magnet assembly (400) within a bead (30, 110, 160, 250, 360).

Magnetic body (402) includes a north pole magnetic section (401), a south pole magnetic section (403), a pair of opposing annular side walls (405), an inner diameter wall (406), and an outer dimeter side wall (407). Magnetic body (402) has an annular shape. Magnetic body (402) may include individually stacked magnetic bodies (similar to how magnets (60) are shown stacked together in FIG. 4) such that the stacked magnetic bodies are suitably aligned with central through hole (408). Alternatively, magnetic body (402) may include a single magnetic body such that no stacking is required. Magnetic body (402) may be manufactured utilizing any suitable manufacturing techniques as would be apparent to one skilled in the art in view of the teachings herein.

Encasement molding (410) includes an encasement material (412) that protects/seals magnetic body (402) from the external environment such that during exemplary use, magnetic body (402) may be inhibited from deteriorating due to undesirable exposure to certain environmental conditions. In some instances, encasement molding will include markings or other visual indicators indicating which side of magnet assembly (400) is associated with north magnetic pole (401) and which side of magnet assembly (400) is associated with south magnetic pole (403).

Figure 40:
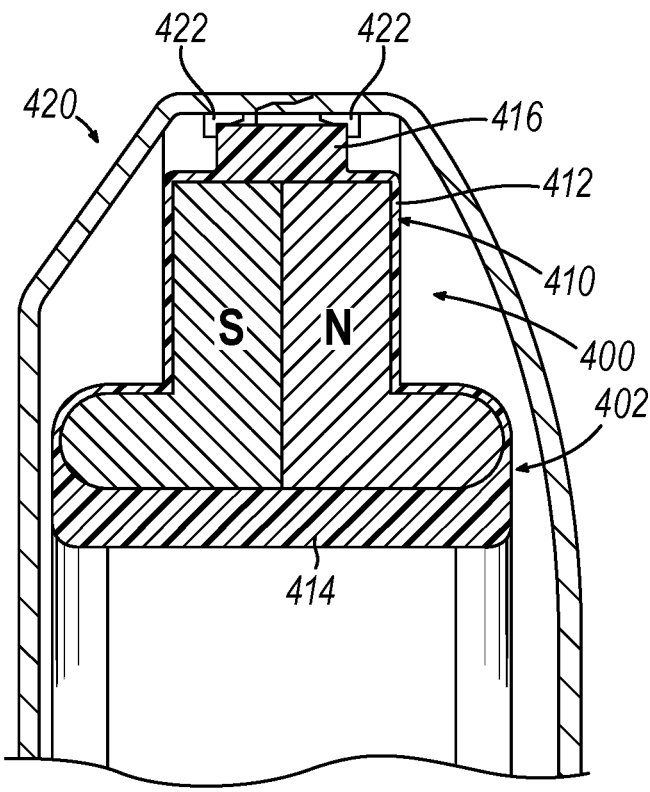
FIG. 40 depicts a cross-sectional view of the magnet assembly of FIG. 39 housed within an alternative bead.

Encasement material (412) provides for a thinner base layer covering magnetic body (402). Additionally, encasement material (412) includes a thicker alignment portion (414) associated with inner diameter portion (406) of magnetic body (402) such that thicker alignment portion (414) defines central opening (408). Thicker alignment portion (414) may be dimensioned for a tight fit against the portion of bead (30, 110, 160, 250, 360) configured to extend through central opening (408), thereby promoting a friction resistance to movement of magnet assembly (400) relative to bead (30, 110, 160, 250, 360). Encasement materials (412) also includes a thicker retainer feature (416) located near outer diameter surface (407) of magnetic body (402). FIG. 40 shows magnet assembly (400) coupled to an exemplary bead (420) having 3D printed brackets (422). 3D printed brackets (422) are dimensioned to abut against thicker retaining feature (416) to thereby inhibit magnet assembly (400) from "floating" relative to bead (420) along the central axis which opening (408) extends along. Such floating may occur due to a stronger magnetic attraction between one adjacent bead (420) compared to the other adjacent bead (420).

Encasement material (412) may be formed from any suitable material as would be apparent to one skilled in the art in view of the teachings herein. For example, encasement material (412) may be formed from an ultra-high molecular-weight polyethylene (UHMWPE) molding. Use of UHMWPE molding may provide cushioning while still preventing floating. Alternatively, any other suitable material or combination of materials may be used.

Magnetic body (402) is contained within encasement molding (410) such that in instances where magnetic body (402) include a plurality of stacked magnet bodies that that are suitably aligned with through hole (408), encasement molding (410) keeps the stacked magnetic bodies substantially fixed relative to each other. In other words, encasement molding (410) may suitably contain a stack of magnets to prevent movement of one magnetic element with respect to another magnetic element in the magnetic stack. Substantially fixing stacked magnetic elements of magnetic body (402) may allow for an assembler to more easily handle magnetic assembly (400) during the assembly process. For example, substantially fixing stacked magnetic elements of magnetic body (402) may allow for easily handling magnetic assembly (400) during re-magnetization and assembly within an exemplary bead (30, 110, 160, 250, 360) in accordance with the description herein. In some instances, a portion of encasement molding (410) may be located in-between stacked magnetic elements when magnetic body (402) is formed via a stack. In other words, a portion of encasement molding (410) may be interposed between adjacent annular side walls (405) of stacked magnetic elements forming magnetic body (402).

Encasement molding (410) may be applied to magnetic body (402) utilizing any suitable means as would be apparent to one skilled in the art in view of the teachings herein. In some instances, magnetic body (402) may be placed into a bead (420) housing first, and then encasement molding (410) may then be added to seal the magnetic body (402). In such instances, encasement molding (410) may be formed of an epoxy material.

Figure 41:
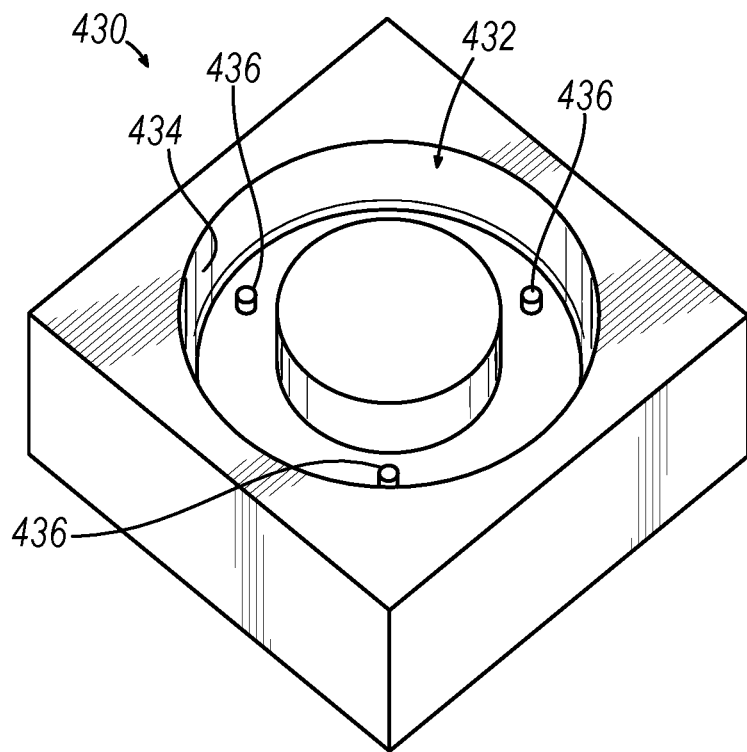
FIG. 41 depicts a perspective view of a half of an injection mold that may be used to apply the encasement molding of the magnet assembly of FIG. 40.
Figure 42:
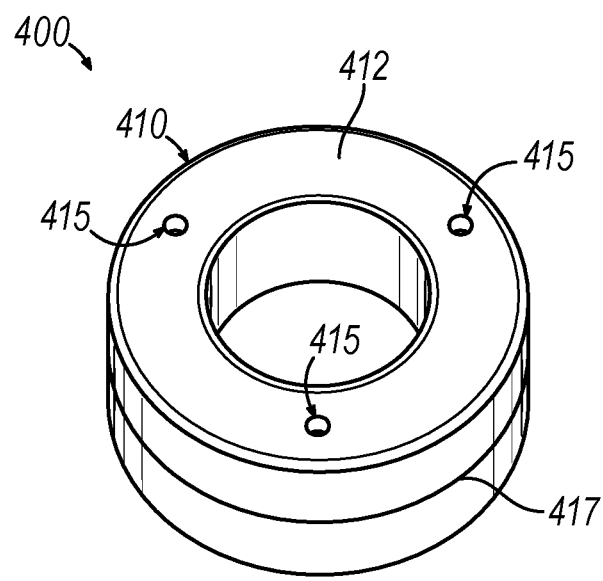
FIG. 42 depicts a perspective view of an encasement molding applied to a magnet to initially form the magnet assembly of FIG. 40.

Other examples of how encasement molding (410) is applied to magnetic body (402) may include injection molding, compression molding, vacuum molding, etc. FIG. 41 shows an exemplary injection mold half (430) that may be used with another mold half (430) to apply encasement molding (410) to magnetic body (402). Mold half (430) defines a complementary recess dimensioned to receive a suitable portion of magnet body (402). It should be understood that the other mold half (430) may also define a complementary recess (432) such that once mold halves (430) are put together, magnet body (402) is substantially encapsulated by mold halves (430). Mold half (430) also includes an annular floor (434) having a suitable number of pins (436) extending from annular floor (434). Pins (436) are configured to elevate magnetic body (402) from annular floor (434) such that encasement molding (410) may be applied to annular side wall (405) resting on pins (436). As shown in FIG. 42, after injection molding is completed with use of mold halves (430), three recessed holes (415) may be present from resting on pins (436), while a part line (417) may exist from where mold halves (430) contact each other. Subsequently, recessed holes (415) may be filled with encasement material (412) via a second-injection shot.

Figure 43:
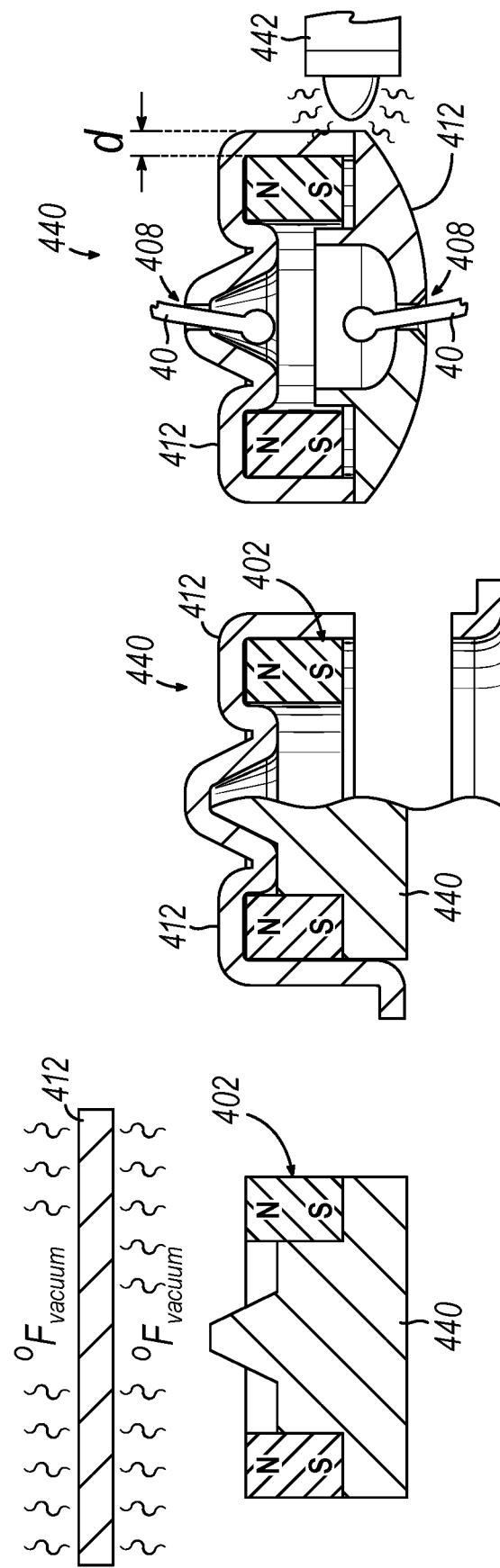
FIG. 43A depicts a cross-sectional view of an encasement molding being placed over a magnet and a vacuum form in preparation of coupling the encasement molding to the magnet via vacuum molding.
FIG. 43B depicts a cross-sectional view of an encasement molding being vacuum molded over the magnet and vacuum form of FIG. 43A.
FIG. 43C depicts a cross-sectional view of the magnet of FIG. 43A covered by the encasement molding of FIG. 43A.

In some instances, the desired encasement material (412) may be formed from plastics that are not compatible with injection molding based on the stacked donut shape of magnetic body (402). In such instances, in may be desirable to use vacuum molding or compression molding in order to suitably apply encasement material (412) onto magnetic body. FIGS. 43A-43C show an example of using vacuum molding to form an encasement molding (410) around magnetic body (402). First, as shown in FIG. 43A, magnetic body (402) may be placed over a vacuum form (440). Vacuum form (440) may have any suitable shape as would be apparent to one skilled in the art in view of the teachings herein. Encasement material (412) may be suitably exposed to heat and a vacuum such that encasement material (412) conforms to the shape of magnetic body (402) and vacuum form (440), as shown in FIG. 43B. Next, vacuum form (440) may be removed and secondary operations such as trimming encasement material (412) may be performed. Next, as shown in FIG. 43C, a preformed base portion of encasement material (412) may be attached to the vacuum formed encasement material (412) via a heat stake (442). Further secondary processes may then be performed, such as forming central through hole (408) dimensioned to receive links (40).

VII. Example of Sealing and Attachment Elements for Connection of Beads

As mentioned above, links (40) couple adjacent beads (30) by extending through openings (33, 35) and into chambers (36) defined by respective beads (30). In some instances, it may be desirable to create a hermetic seal between openings (33, 35) and link (40) such that device (20) may transition between the expanded state and the contracted state, without allowing fluids to enter or exit chamber (36). Further, it may be desirable to provide link (40) with attachment and sealing elements for slidably attaching link (40) with beads (30) in accordance with the description herein; and for creating a hermetic seal between chamber (36) and an external environment. Having a link (40) with such capabilities may eliminate a need to housings (32, 34) at a location near one opening (33, 35). Further, having a link (40) with such capabilities may eliminate a desire to isolate magnets (60) from chamber (36).

Figure 44:
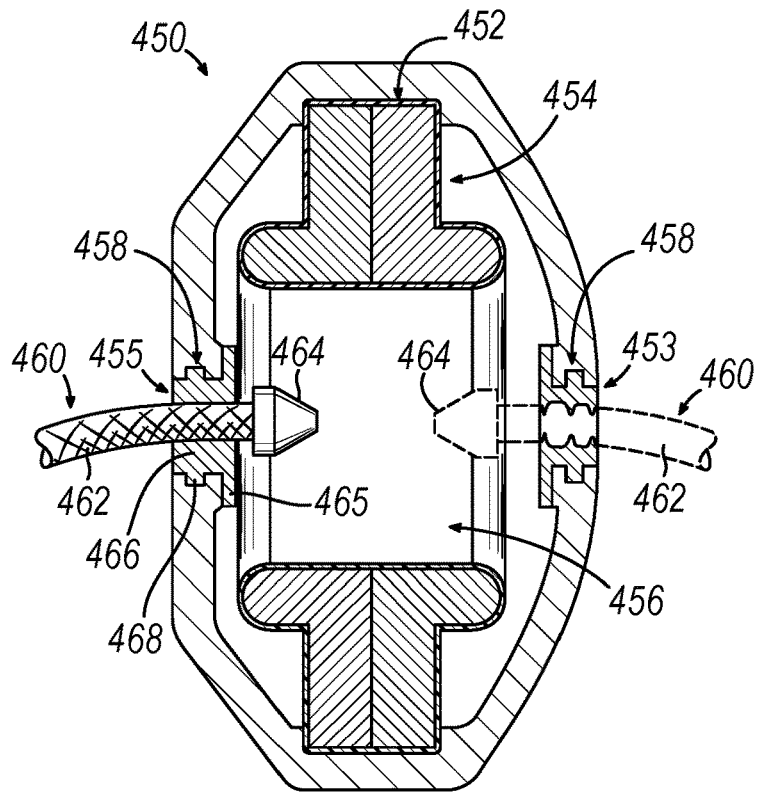
FIG. 44 depicts a cross-sectional view of an exemplary bead and magnet slidably coupled to a pair of connecting links to form a hermetic seal.

FIG. 44 shows a bead (450) housing a magnet (454), where two links (460) are slidably attached to bead (450). As will be described in greater detail below, links (460) each include a sealing end cap (466) that is configured to expand against a portion of bead (450) defining a respective opening (453, 455) during assembly of link (460) and bead (450) in order to create a seal between chamber (456) and openings (453, 455). Additionally, link (460) includes a woven stranded cable (462) that is configured to slide relative to sealing end cap (466) and bead (450) after assembly such that the formed device may expand and contract in accordance with the teachings herein.

Body of bead (450) defines a chamber (456) dimensioned to contain magnet (454) and ends (464) of links (460) while allowing a woven stranded cable (462) of link (460) to slide into and out of chamber (456). Body of bead (450) also defines an annular magnet recess (452) dimensioned to receive and constrain magnet (454) within chamber (456) relative to the body of bead (450). Body of bead (450) defining openings (453) also defines annular sealing recesses (458) dimensioned to receive seal end caps (466) to thereby form a hermetic seal between chamber (456) and the external environment outside of openings (453, 455).

As mentioned above, links (460) include sealing end caps (466) formed from a formable or memory material. Sealing end caps (466) may be formed from a plastic or thermoform material such that during initial coupling, sealing end caps (466) may be inserted within openings (453, 455) without forming a hermetic seal. In some instances, sealing end caps (466) may be dimensioned to be easily inserted within openings (453, 455). Sealing end caps (466) may be formed of an expandable shape memory material, a finned shape member plug, and/or an expanding torque plug, such that upon being exposed to a sufficient heat and/or vacuum pressure for a sufficient period of time, sealing end cap (466) may suitably expand against the portion of bead (450) defining openings (453, 455) to thereby form a hermetic seal between chamber (456) and the external environment outside of openings (453, 455). Once suitably expanded, end cap (466) may fill the space of annular sealing recess (458) to help form the hermetic seal. End cap (466) may also suitably expand to form a sealing flange (465) on the interior and/or exterior of bead (450).

Once the hermetic seal is complete, woven stranded cable (462) may slide through the opening defined by sealing end cap (466) without damaging the seal between the openings defined by end caps (466) and woven stranded cable (462). Additionally, woven stranded cable (462) may slide through the opening defined by sealing end cap (466) without damaging the seal between opening (453, 455) and sealing end cap (466). In some instances, the opening defined by end cap (466) may include internal teeth or annular ridges that may suitably engage woven stranded cable (462) to further promote a sealed chamber (456). In some instances, the interaction between the opening defined by end cap (466) and woven stranded cable (462) may inhibit woven stranded cable (462) from sliding relative to end cap (466). In such instances, woven stranded cable (462) may collapse, bundle, and/or wad up between beads (450) when the version of sphincter augmentation device (20) incorporating beads (450) and links (460) transitions into the contracted state.

In some instances, end cap (466) could also have an elastomer sealing portion like an O-ring to prevent fluid transfer. In some instances, end cap (466) and bead (450) could have a feature that allows for an epoxy to be filled during manufacturing to complete the hermetic seal.

Figure 45:
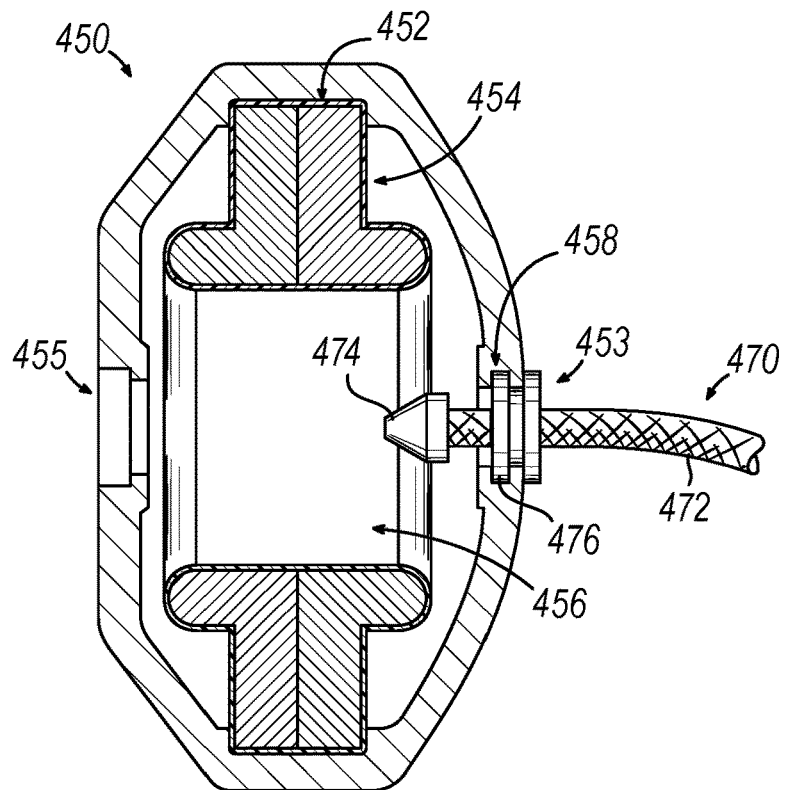
FIG. 45 depicts a cross-sectional view of an exemplary bead and magnet slidably coupled to a connecting link to form a hermetic seal.

FIG. 45 shows an alternative link (470) that may be used with bead (450) in replacement of link (460) described above. Link (470) includes a woven stranded cable (472) and an end (474) that are substantially similar to woven stranded cable (462) and end (464) described above. However, rather than being having a sealing end cap made from a formable or memory material, link (470) includes a snap-fit sealing end cap (476). Snap-fit sealing end cap (476) may include a compression cap that slides into opening (453, 455) when inserted with enough force to form a snap-fit sealing. Snap-fit sealing end cap (476) may include a suitable plastic and/or elastomer material to maintain a suitable seal once coupled with bead (450). Once the hermetic seal is complete via snap-fit, woven stranded cable (472) may slide through the opening defined by sealing end cap (476) without damaging the seal between the openings defined by end caps (476) and woven stranded cable (472). Additionally, woven stranded cable (472) may slide through the opening defined by sealing end cap (476) without damaging the seal between opening (453, 455) and sealing end cap (476). Alternatively, woven stranded cable (472) may collapse, bundle, and/or wad up between beads (450) when the version of sphincter augmentation device (20) incorporating beads (450) and links (470) transitions into the contracted state.

It should be understood that while woven stranded cable (462, 472) is used in the current example, link (460, 470) may be formed of wires similar to link (40) described above, or any other suitable material/structure as would be apparent to one skilled in the art in view of the teachings herein.

VIII. Example of Beads with Interactive Geometry for Bead Orientation Control

In some instances, it may be desirable to have beads (30) with exterior surfaces that interact with the exterior surfaces of adjacent beads (30) in a certain manner in order to drive beads (30) into a predetermined, preferential orientation relative to each other when transitioning into and out of the contracted state. Additionally, it may be desirable to have adjacent beads (30) with complementary exterior surfaces that resist undesirable movement of beads (30) in directions other than along the path between the contracted and expanded states (such as twisting or tilting adjacent beads (30) relative to each other in the contracted state). Additionally, it may be desirable to have beads (30) with a geometric shape that reduces or balances the constriction pressure distribution on tissue engaged by device (20) in the contracted state to improve interaction with more fragile tissues and sphincter locations.

Figure 46:
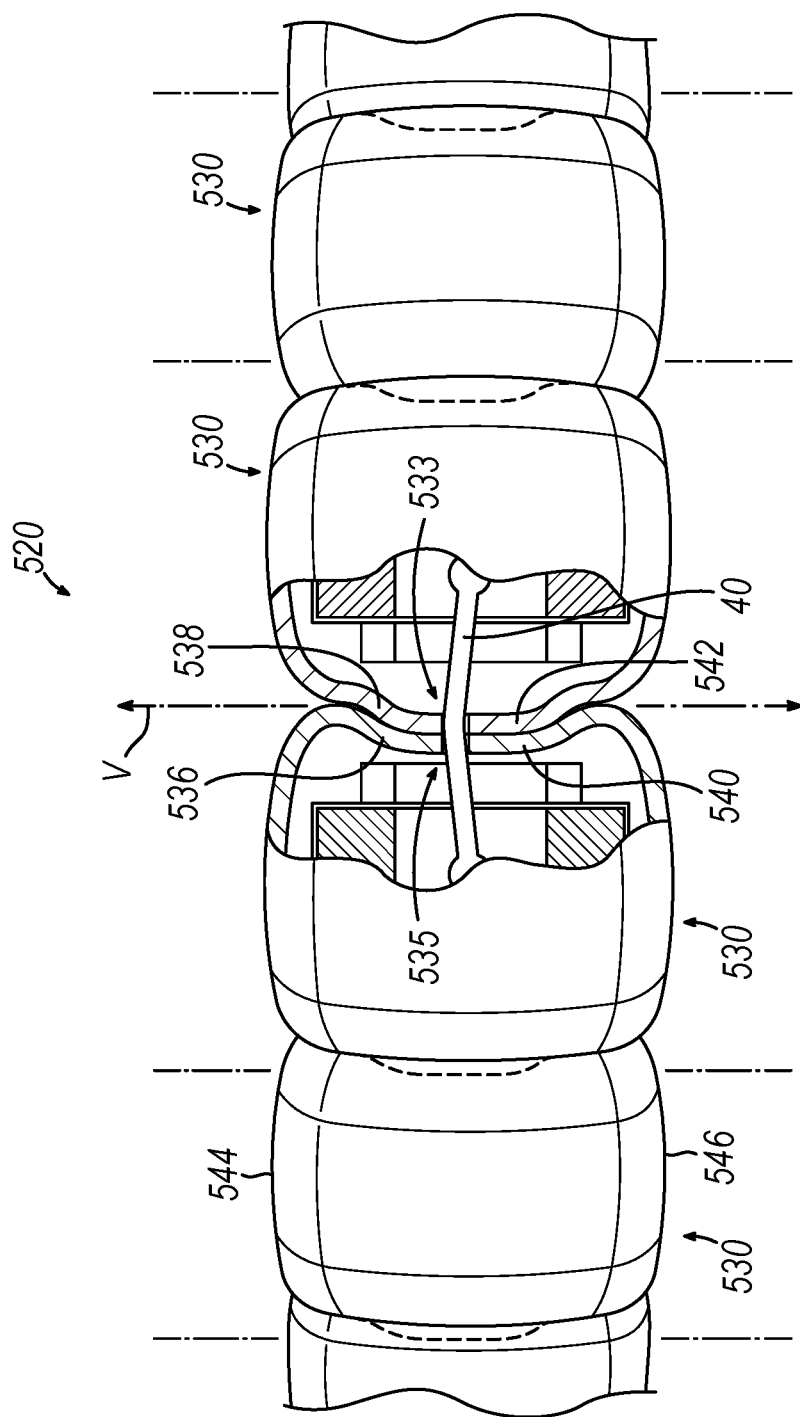
FIG. 46 depicts an elevational front view of an alternative sphincter augmentation device, with selected portions broken away for purposes of clarity.
Figure 47:
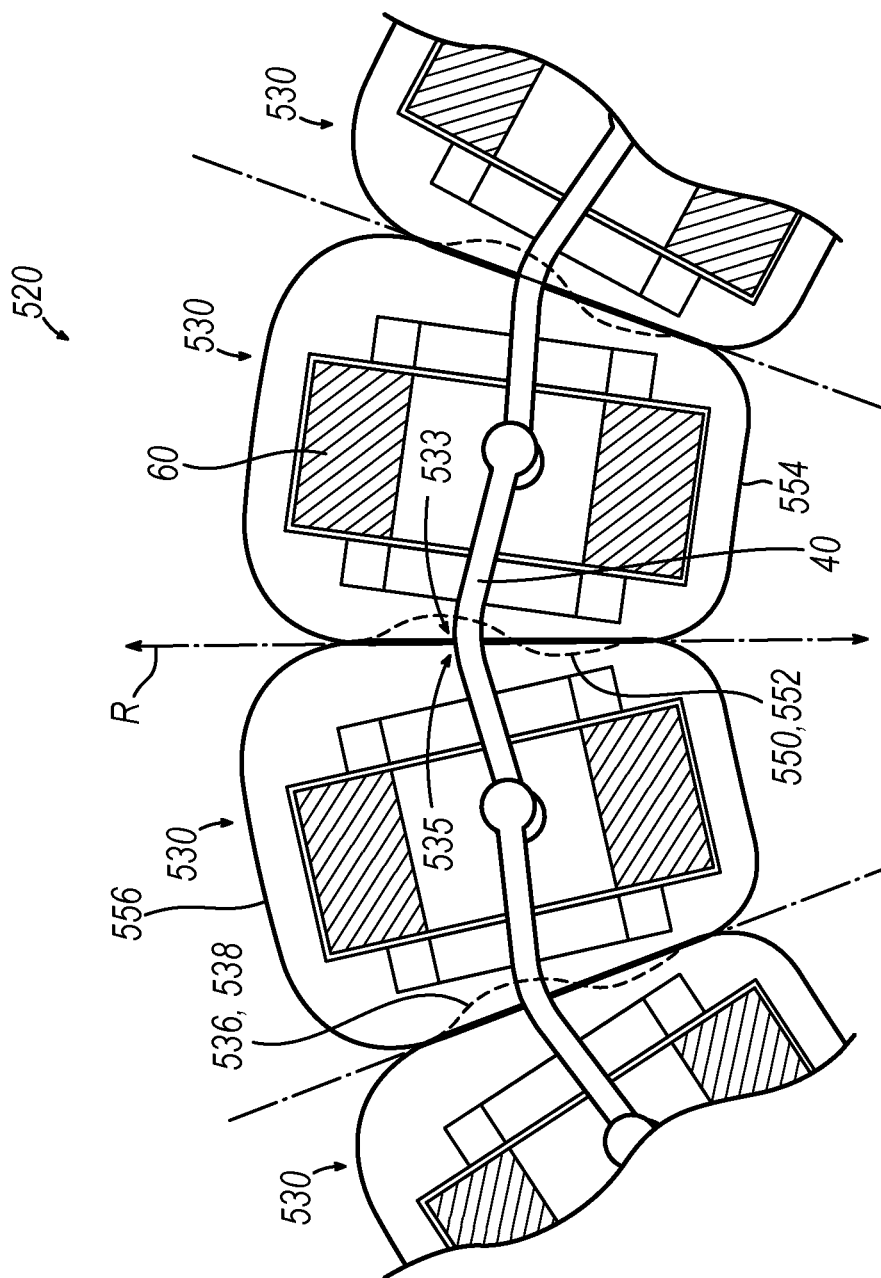
FIG. 47 depicts a cross-sectional view of the sphincter augmentation device of FIG. 46.

FIGS. 46-47 show an example sphincter augmentation device (520) having beads (530) with complementary geometry configured to drive beads (530) into a predetermined, preferential orientation relative to each other when sphincter augmentation device (520) transitions into and out of the contracted state. As will also be described in greater detail below, beads (530) have an inner diameter surface (554) that may be concentric about the expansion axis of device (520), which allows inner diameter surfaces (554) to have a pre-defined minimum radius and pressure profile while device (520) is in the contracted state.

Device (520) includes a plurality of beads (530), with each bead (530) housing a respective magnet (60). Beads (530) are substantially similar to beads (30) described above, with differences elaborated below. Therefore, beads (530) include openings (533, 535), which are substantially similar to openings (33, 35) described above. Beads (530) are slidably coupled to links (40) such that device (520) may transition between a contracted state and an expanded state in similar fashion to device (20) descried above. Beads (530) are magnetically biased toward the contracted state via magnetic fields generated by magnets (60).

Figure 48:
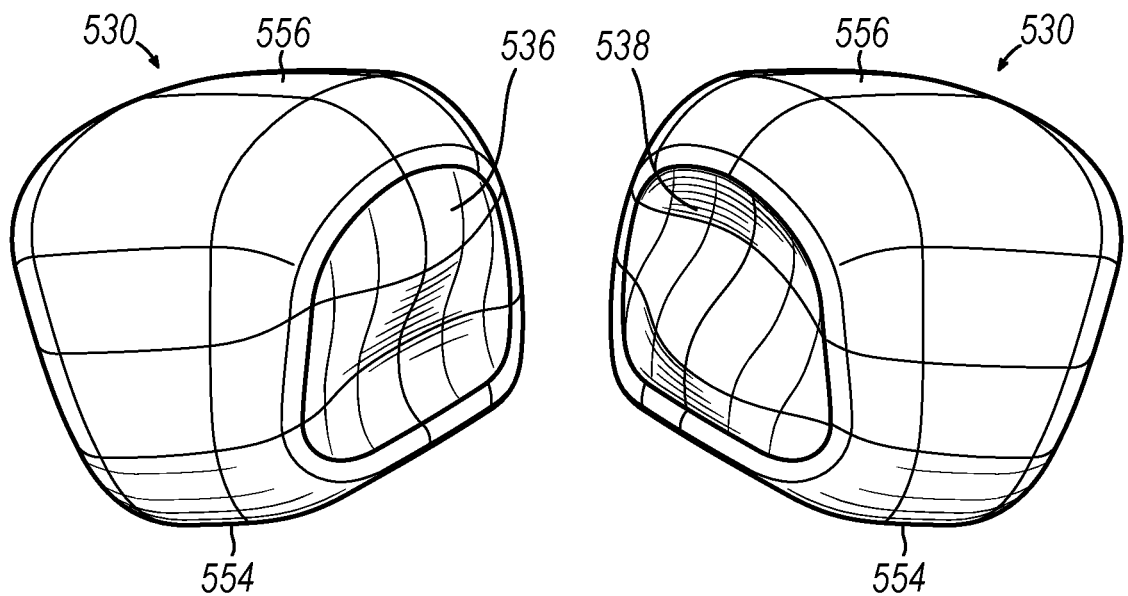
FIG. 48 depicts a perspective view of a pair of adjacent beads of the sphincter augmentation device of FIG. 46.
Figure 49:
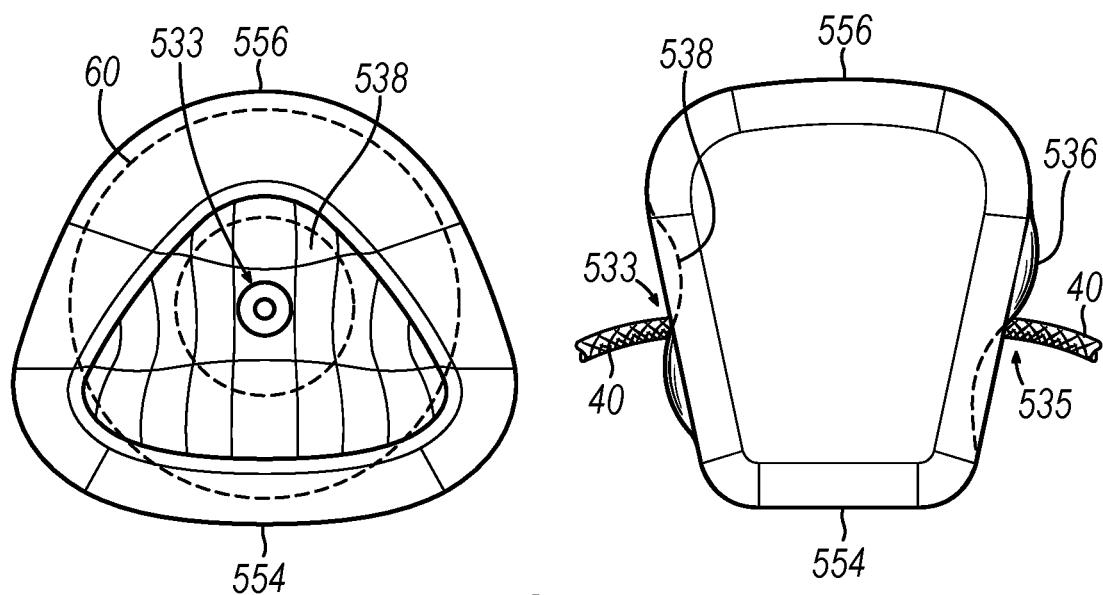
FIG. 49 depicts an elevational side view and a top plan view of a first bead and a second bead, respectively, of the sphincter augmentation device of FIG. 46.

Each bead (530) also includes a pair of side surfaces (536, 538) defining a respective opening (533, 535), an inner diameter surface (554), and an outer diameter surface (556). As shown in FIGS. 48-49, each side surface (536, 538) is dimensioned to abut against a complementary side surface (538, 536) of an adjacent bead (530) in the contracted state.

As best shown in FIG. 46, side surface (536) includes a vertically constraining concave profile (540); while side surface (538) includes a vertically constraining convex profile (542). Vertical concave profile (540) of side surface (536) and vertical convex profile (542) of side surface (538) are dimensioned to nest with each other while device (520) is in the contracted state. In other words, profiles (540, 542) are complementary with each other such that while device (520) is in the contracted state, side surfaces (536, 538) sufficiently engage each other to drive beads (530) into a predetermined, preferential orientation relative to each other along the vertical dimension (V) when transitioning into and out of the contracted state. Additionally, engagement by complementary profiles (540, 542) may also inhibit adjacent beads (530) from slipping relative to each other in the vertical direction (V) while device (520) is in the contracted state. The magnetic attraction between beads (530) may increase the frictional braking force between side surfaces (536, 538) in the contracted state, thereby further promoting the engagement of concave profile (540) and convex profile (542).

As best shown in FIG. 47, side surface (536) also includes a radially constraining curved profile (550); while side surface (538) includes a complementary radially constraining profile (552). Radially constraining curved profiles (550, 552) are dimensioned to nest with each other while device (520) is in the contracted state. In other words, profiles (550, 552) are complementary with each other such that while device (520) is in the contracted state, side surfaces (536, 538) sufficiently engage each other to drive beads (530) into a predetermined, preferential orientation relative to each other along the radial direction (R) when transition into and out of the contracted state. Additionally, engagement by complementary profiles (550, 552) may also inhibit adjacent beads (530) from slipping relative to each other in the radial direction (R) while device (520) is in the contracted state. The magnetic attraction between beads (530) may increase the frictional braking force between side surfaces (536, 538) in the contracted state, thereby further promoting the engagement of complementary radially constraining curved profiles (550, 552). In the present example, each curved profile (550, 552) has an undulating configuration, with curved profile (550) representing a negative of curved profile (552). Alternatively, curved profiles (550, 552) may have any other suitable nesting configuration.

As best shown in FIGS. 47-49, beads (530) are asymmetrical such that inner diameter surface (554) is dimensioned differently than outer diameter surface (556). In particular, the asymmetrical profile is formed along on axis that extends between openings (533, 534). Inner diameter profile (554) has a perimeter conical shape while outer diameter profile (556) has a more spherical shape. Inner diameter profile shape (554) may allow adjacent beads (530) to mate on a predefined mating surface. Additionally, inner diameter profile (554) is substantially concentric around the expansion and contraction axis of device (520). This asymmetrical formation may allow inner diameter profile (554) to define a conforming tissue engagement surface in the contracted state while the outer dimeter profile (556) may reduce the chances of beads (530) snagging and catching onto other anatomical structures adjacent to the esophagus during transitions between the expanded and contracted state. The concentric nature of inner diameter profile (554) may also create a preferred collapse surface when device (520) is in the contracted state. The shape of inner diameter profile (554) may also allow inner diameter profile (554) to have a predefined minimum pressure profile, which may be allow device (520) to be utilized with more fragile tissues and sphincter locations.

In some instances, every other bead (530) could be a non-magnetic holding, inactive bead. These inactive beads could be sized differently from beads (530) with magnets (60). These inactive beads could have interactive surfaces that are intended to give the contracted state a predefined shaped and minimum inner diameter profile (554). These inactive beads would also act as a gapping element that would prevent any two beads from creating a paired coupling which could undesirably result in beads (530) twisting or changing their orientation with respect to the intended structure of device (520).

In addition to providing alignment along the vertical dimension (see FIG. 46) and radial dimension (see FIG. 47), complementary side surface (538, 536) may also provide alignment about the circumferential direction. In other words, in the event that one bead (530) becomes twisted about the circumference of device (520) in the expanded state, complementary side surface (538, 536) may twist the mis-aligned bead (530) back into alignment about the circumference of device (520) as device (520) transitions to the contracted state.

IX. Example of Implantable Sphincter Assistance Device with Selectively Adjustable Bead Interconnection Length In some instances, it may be desirable to adjust the circumference of device (20) in the contracted state (i.e., the contracted circumference). For instance, it may be desirable to adjust the circumference of device (20) after device (20) has been implanted in order to ensure that device (20) properly functions in the contracted state by preventing the patient from experiencing GERD and/or other undesirable conditions that may be associated with a persistently open opening (7) at the LES (6). In some instances, it may be desirable to actively adjust the contracted circumference of device (20) such that a surgeon may make such adjustments while device (20) is implanted. In other instances, it may be desirable to passively adjust the contracted circumference of device (20) such that the contracted circumference is at least partially based on the radial forces acting on device (20) after implantation.

Figure 50A:
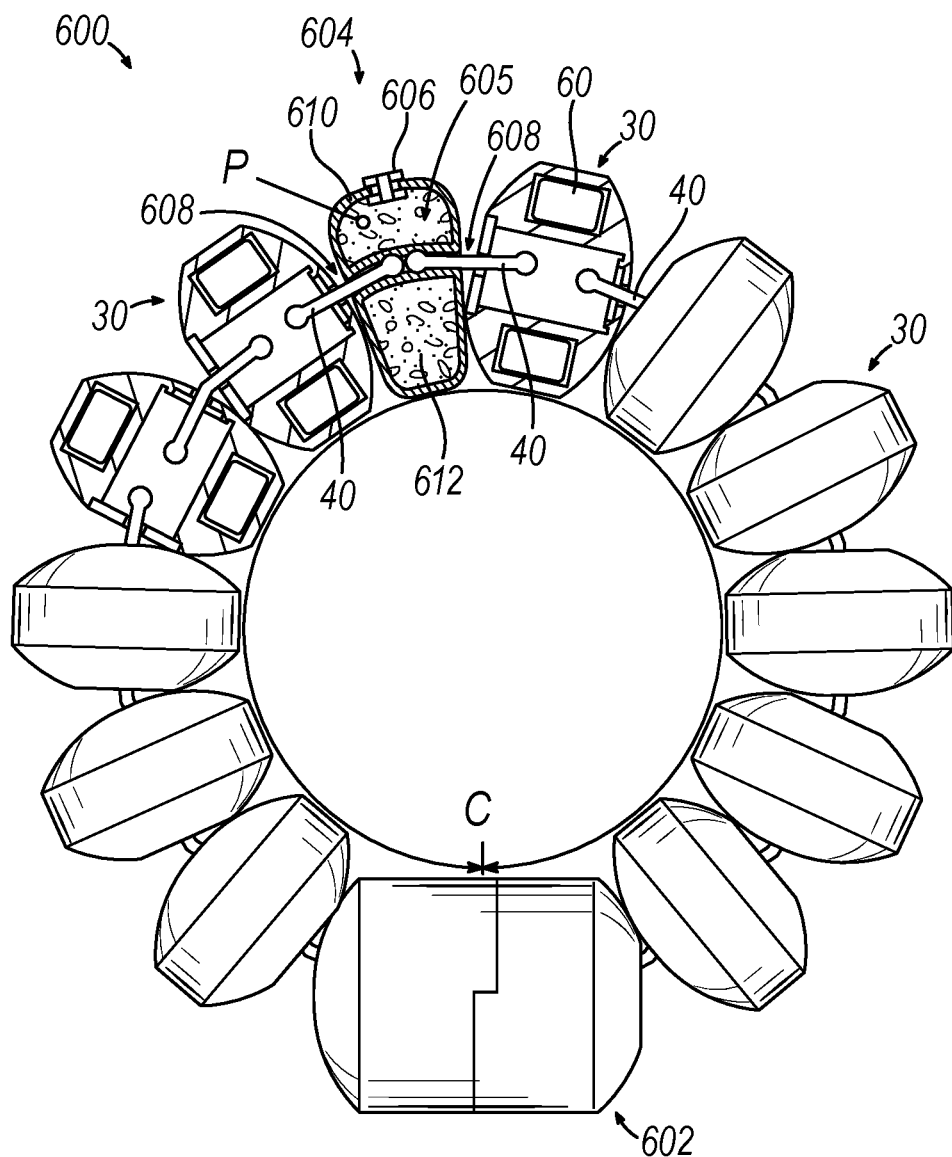
FIG. 50A depicts a top plan view of an alternative sphincter augmentation device in a first circumferential size in the contracted configuration.
Figure 50B:
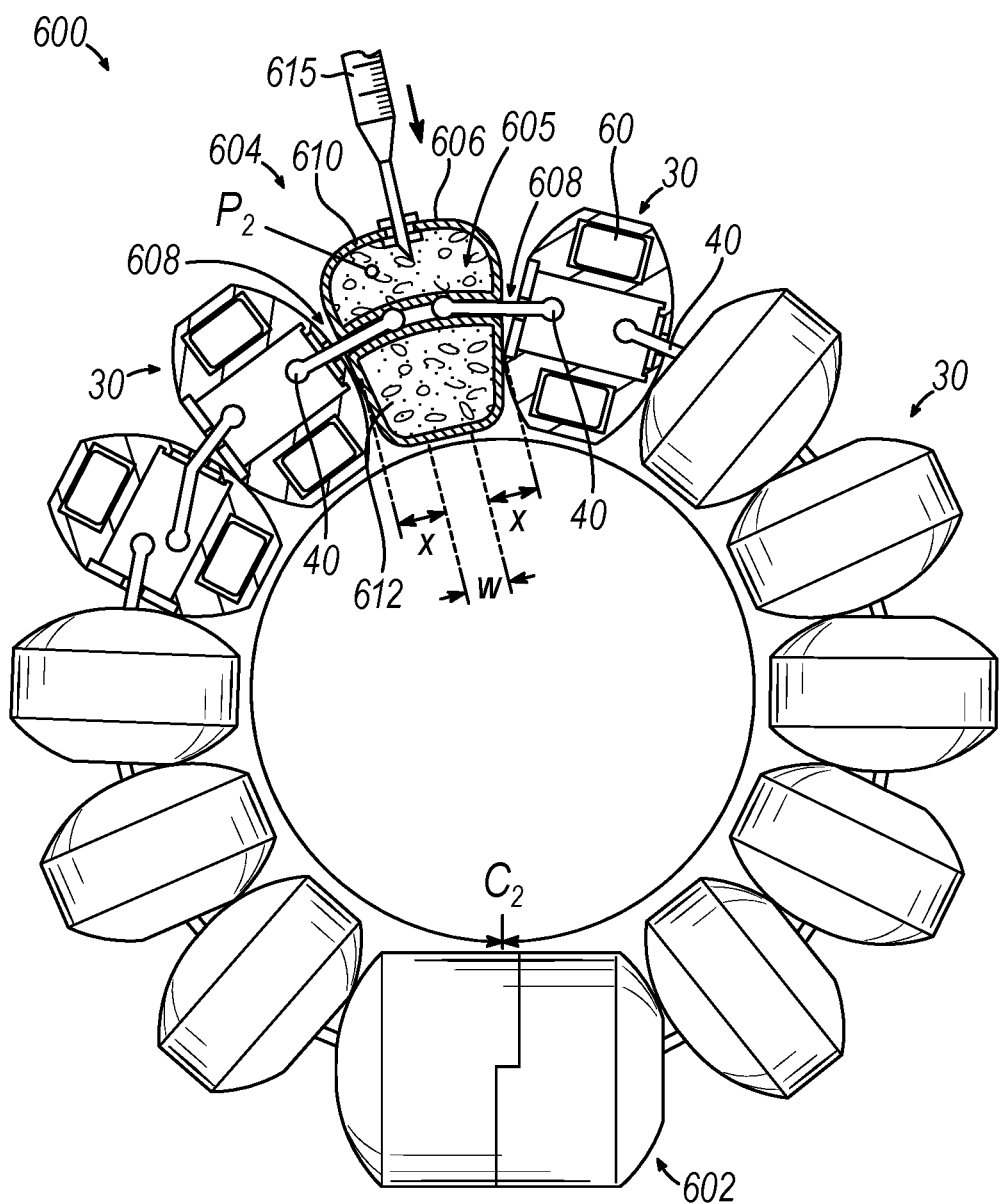
FIG. 50B depicts a top plan view of the sphincter augmentation device of FIG. 50A in a second, enlarged, circumferential size in the contracted configuration.
Figure 50C:
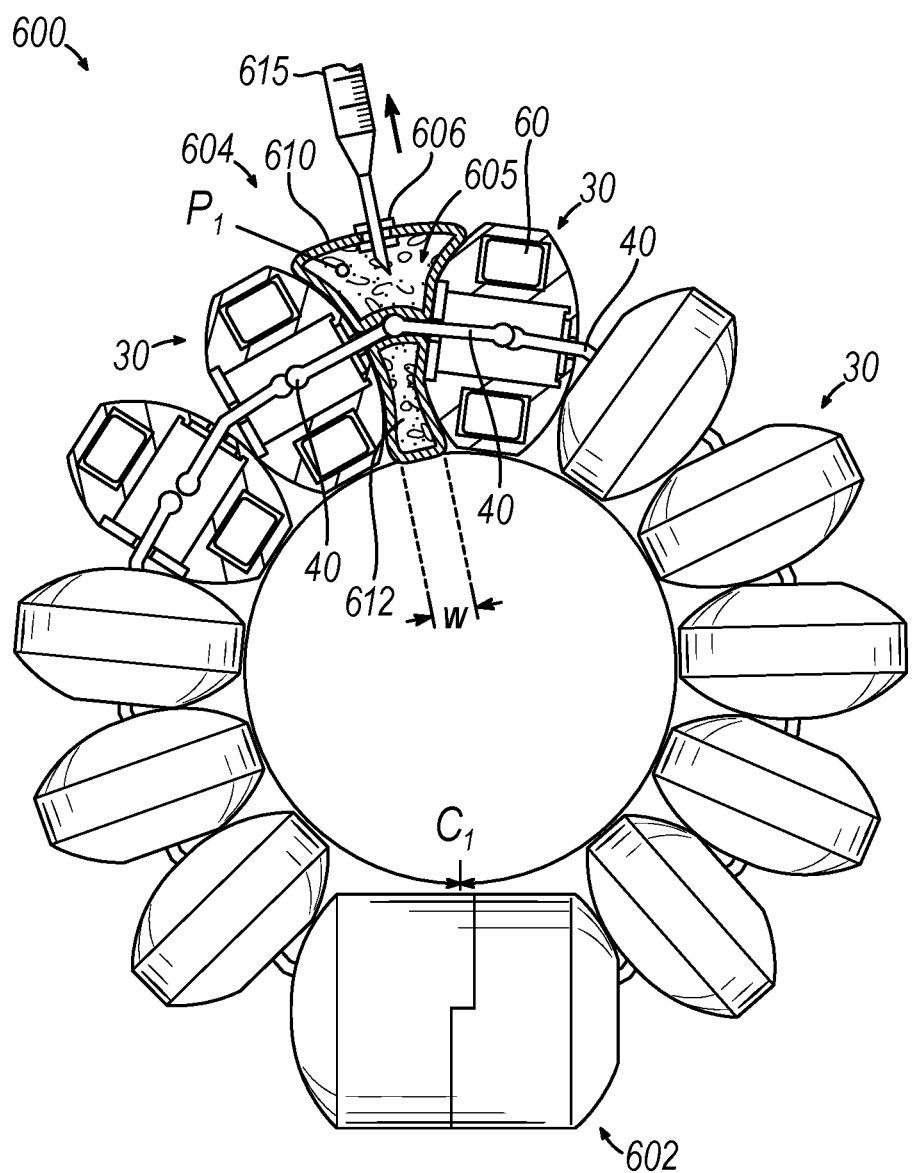
FIG. 50C depicts a top plan view of the sphincter augmentation device of FIG. 50A in a third, reduced, circumferential size in the contracted configuration.

FIGS. 50A-50C show an exemplary alternative sphincter augmentation device (600) that may be used in replacement of sphincter augmentation device (20) described above. Therefore, device (600) may be substantially similar to device (20) described above, with differences elaborated below. Similar to device (20) described above, device (600) includes a plurality of beads (30), each housing at least one magnet (60), where beads (30) are joined together by a plurality of links (40). A clasping feature (602), which may function similar to fastener features (50), allows the ends of device (600) to be coupled together to form a loop. Device (600) is configured to transition between a contracted state and an expanded state in similar fashion to device (20) described above.

Device (600) also includes an elastomeric inflatable ring (604) interposed between two beads (30). As will be described in greater detail below, an operator may utilize elastomeric inflatable ring (604) in order to adjust the circumference of device (600) in the contracted state. Inflatable ring (604) includes an inflatable port (606) and an inflatable body (610). Inflatable body (610) defines a fluid chamber (605) and a transverse chamber (608) that is fluidly isolated from fluid chamber (605).

Transverse chamber (608) extends between lateral sides of ring (604) and is dimensioned to receive adjacent links (40). Transverse chamber (608) slidably receives and retains links (40) such that ring (604) may expand and contract relative to adjacent beads (30) in similar fashion that beads (30) expand and contract relative to each other in order to transition device (20) between the contracted state and the expanded state, although this is merely optional. In the current example, two links (40) extend into chamber (608) such that a first link (40) couples ring (604) with a first adjacent bead (30), and a second link (40) couples ring (604) with a second adjacent bead (30). However, in some instances, a single link (40) is received by inflatable ring (604) such that one link (40) extends from one adjacent bead (30), through inflatable ring (604), and into the other adjacent bead (30).

Fluid chamber (605) is filled with saline (612). The amount of saline (612) filled within fluid chamber (605) may alter the pressure within fluid chamber (605) as well as the volume of fluid chamber (605). Therefore, a surgeon may selectively control the amount of saline (612) within fluid chamber (605) in order to alter the contracted circumference of device (600). While in the current example, fluid chamber (605) is filled with saline (612), any other suitable fluid may be used to fill fluid chamber (605) as would be apparent to one skilled in the art in view of the teachings herein.

Inflatable port (606) is configured to selectively provide fluid communication between a syringe (615) and fluid chamber (605) such that syringe (615) may alter the amount of fluid (and therefore alter the volume and pressure within chamber (605)) via syringe (615). Inflatable port (605) is configured to prevent saline (612) from inadvertently escaping fluid chamber (605) via port (605) during exemplary use of device (600). Inflatable port (605) is located at a location on inflatable ring (604) that is still accessible via syringe (615) even after device (600) is looped around the intended anatomical structure (e.g., LES (6)). In the current example, inflatable port (605) is located on a surface of inflatable body (610) near the outer diameter portion. Inflatable port (606) may include a needle-penetrable septum and/or any other suitable components as would be apparent to one skilled in the art in view of the teachings herein.

FIGS. 50A-50C show an exemplary use of inflatable port (606) and syringe (615) in order to selectively alter the circumference of device (600) in the contracted state. FIG. 50A shows device (600) forming a closed loop due to clasping portion (602) being coupled. At this moment, device (600) may be looped around a desired anatomical passageway, such as LES (6). Additionally, at the moment shown in FIG. 50A, inflatable ring (604) is filled with an amount of saline (612) to provide an initial pressure level (P) within fluid chamber (605), resulting in device (600) have a first circumference (C) in the contracted state.

If a surgeon desired to increase the circumference (C) of device (600) in the contracted state, as shown in FIG. 50B, surgeon may couple syringe (615) with inflation port (606) and add more saline (612) to fluid chamber (605). Adding more saline (612) in fluid chamber (605) increases the pressure ($P_2$) within chamber (605), which expands the volume and the width of ring (604). Expansion of ring (604) alters the size of device (600) into a larger contracted circumference ($C_2$) compared to the initial circumference (C). The size change of device (600) may be formed by a change in size of inflatable ring (604) from the initial width shown in FIG. 50A into an enlarged width including a minimum width (w) and a maximum lateral extension (x) on each side of inflatable ring (604) toward adjacent beads (30). If a surgeon desires to decrease the circumference (C) of device (600) in the contracted state, as shown in FIG. 50C, the surgeon may couple syringe (615) with inflation port (606) and remove saline (612) from fluid chamber (605). Removing saline (612) from fluid chamber (605) decreases the pressure ($P_1$) within chamber (605), which reduces the volume and the width of ring (604). Contraction of ring (604) alters the size of device (600) into a smaller contracted circumference ($C_1$) compared to the initial circumference (C). In particular, ring (604) contacts into minimum width (w) with no additional lateral extension. Therefore, a surgeon may actively alter the circumference of device (600) based on the fluid within inflatable ring (604), thereby allowing the surgeon to fine tune the engagement between device (600) and the surrounded anatomical structure after device (600) is implanted.

Figure 51A:
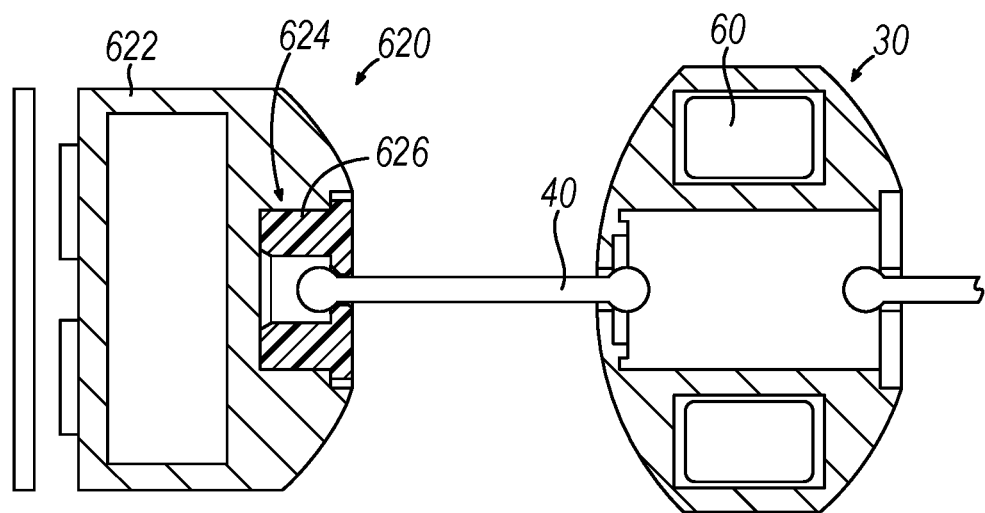
FIG. 51A depicts a cross-sectional view of a clasp feature and a bead connected to each other by a link at a first predetermined length.
Figure 51B:
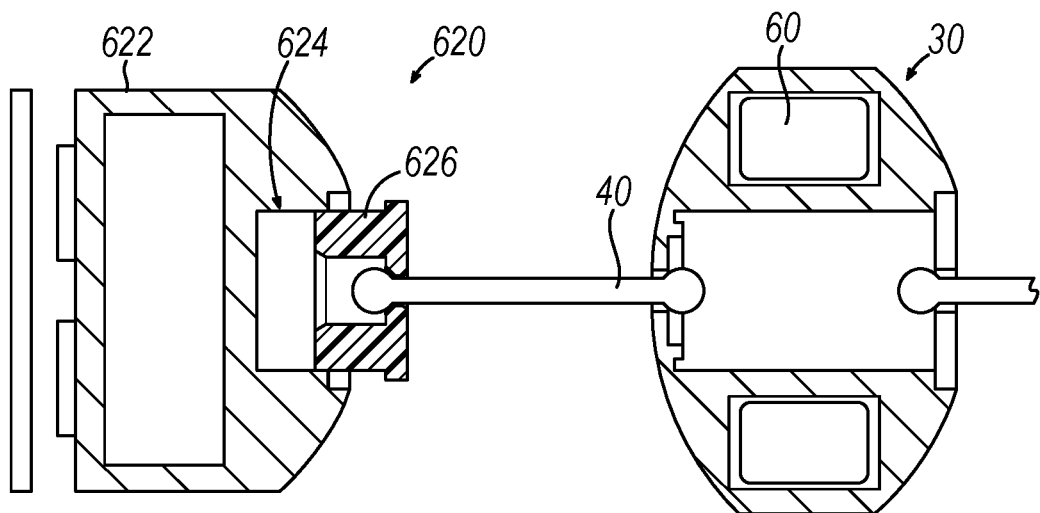
FIG. 51B depicts a cross-sectional view of the clasp feature and the bead of FIG. 51A connected to each other by the link at a second predetermined length.

FIGS. 51A-51B shows another active length adjustment feature (620) that may be readily incorporated into device (600) to thereby actively control the circumference of device (600) in the contracted state. Length adjustment feature (620) includes a clasp feature (622) defining a recessed opening (624), and an adjustable link coupling body (626) housed within recessed opening (624).

Clasp feature (622) may function substantially similar to clasp feature (602) described above. Adjustable link coupling body (626) is suitably attached to a link (40). In some instances, link (40) may be slidably attached to link coupling body (626). In other instances, link (40) may be attached relative to link coupling body (626) such that link (40) may not slide relative to body (626).

Recessed opening (624) suitably engages adjustable link coupling body (626) such that a surgeon may activate change the length at which link coupling body (626) extends from recessed opening (624), as shown between FIG. 51A-51B. Once link coupling body (626) is moved to the desired length relative to clasp feature (622), link coupling body (626) may be substantially fixed relative to clasp feature (622) during exemplary use of device (600) after implantation. Therefore, a surgeon may utilize clasp feature (622) to place implant device (600) around an anatomical structure in accordance with the description herein. Thereafter, if the surgeon desires to increase the circumference of device (600) after implantation, the surgeon may extend body (626) to the position shown in FIG. 51B, or any suitably position in between those shown in FIGS. 51A-51B. Conversely, if the surgeon desires to decreases the circumference of device (600) after implantation, the surgeon may retract body (62) to the position shown in FIG. 51A.

Any suitable components may be used to provide selective adjustability between body (626) and clasp feature (622) as would be apparent to one skilled in the art in view of the teachings herein. For example, a body (626) and clasp feature (622) may have a threaded engagement between each other to actively adjust the length body (626) extends from recessed opening (624).

In some instances, just adjustability is configured to be irreversible. For example, body (626) may be maintained in an initial position within recessed opening (624) via a suitable fusion material, and if the surgeon desires to irreversibly extend the length, the surgeon may break the coupling of a suitable fusion material via ultrasound or RF energy to thereby allow body (626) to extend relative to clasp feature (622). Once the fusion material is broken, the fusion material may no longer maintain the initial position of body (626) within recessed opening (624).

In some instances, body (626) and clasp feature (622) may be provided with RF antennas for receiving internal power. Such internal power may allow for the adjustment between body (626) and clasp feature (622). Such adjustments may be malleable or may cause expansion between body (626) and clasp feature (622) by snapping body (626) into various adjustments sizes. For instance, a body (626) and/or clasp feature (622) may include a two-part capsule with epoxy fusing materials that may be ruptured remotely via application of ultrasonic and/or RF energy. When such a capsule is ruptured, the rupture of the capsule may allow enlargement of the effective length defined by the combination of body (626) and link (40) (e.g., similar to the transition shown from FIG. 51A to FIG. 51B). In some such cases, the enlargement of the effective length defined by the combination of body (626) and link (40) may be permanent.

Figure 52A:
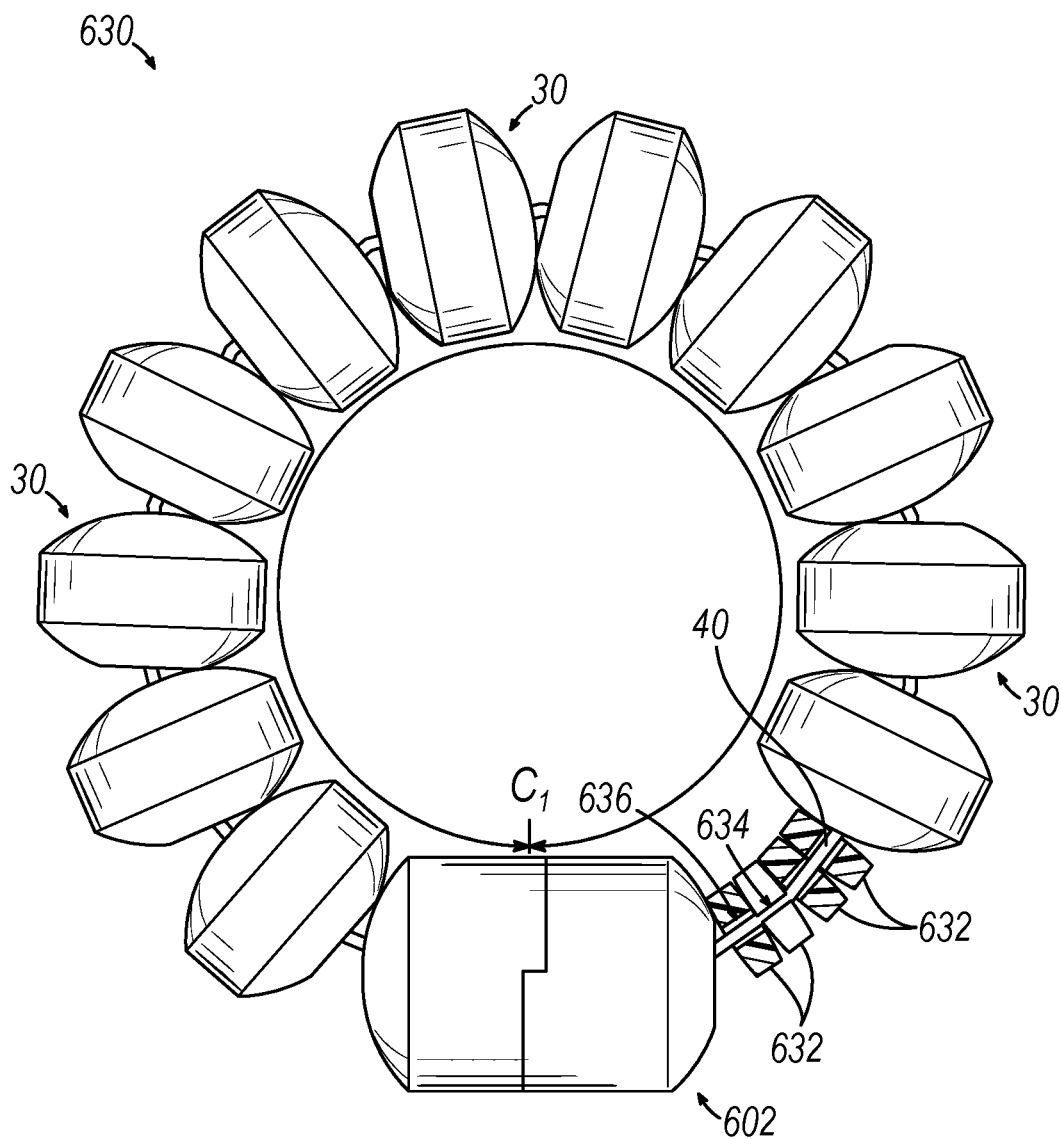
FIG. 52A depicts a top plan view of an alternative sphincter augmentation device in a first circumferential size in the contracted configuration.
Figure 52B:
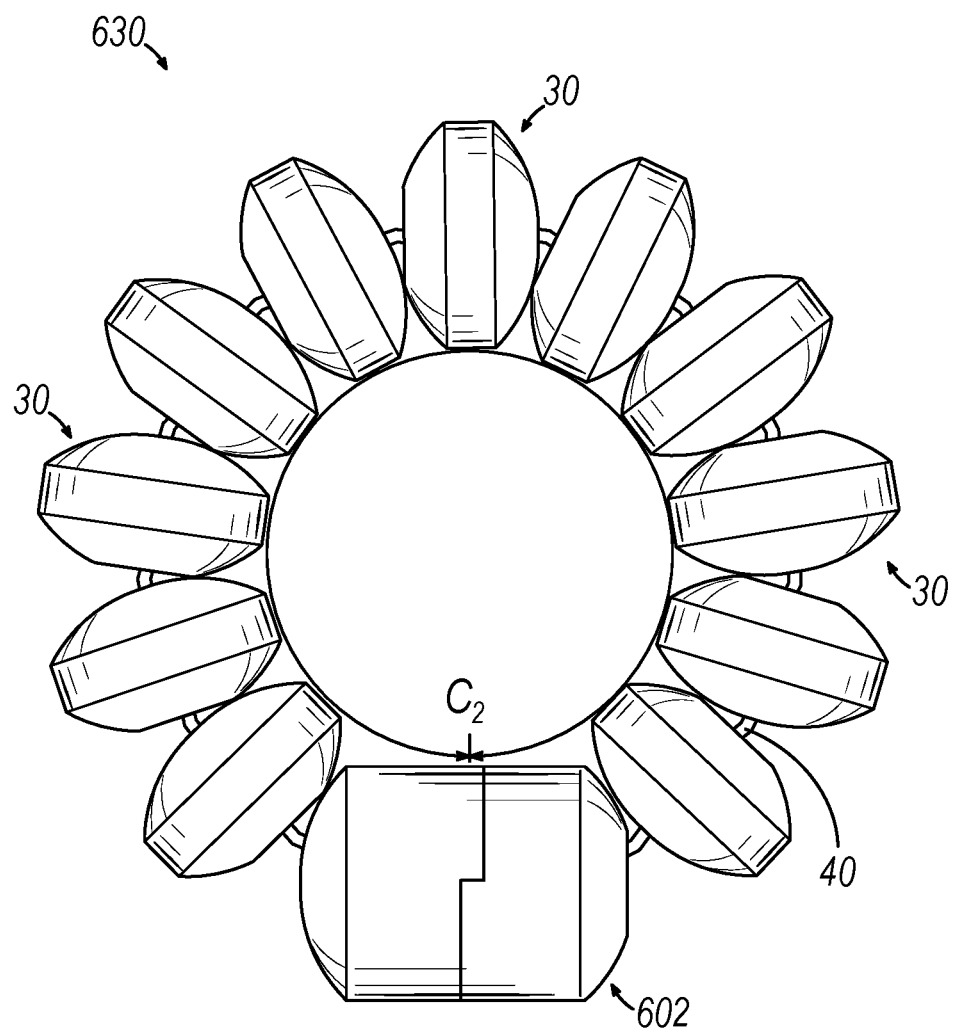
FIG. 52B depicts a top plan view of the sphincter augmentation device of FIG. 52A in a second circumferential size in the contracted configuration.

FIG. 52A-52B show another exemplary alternative sphincter augmentation device (630) that may be used in replacement of sphincter augmentation device (20) described above. Therefore, device (630) may be substantially similar to device (20) described above, with differences elaborated below. Similar to device (20) described above, device (630) includes a plurality of beads (30), each housing at least one magnet (60), where beads (30) are joined together by a plurality of links (40). Device (630) also includes clasping feature (602), which may function similar to fastener features (50) to allow the ends of device (630) to be coupled together to form a loop. Device (630) is configured to transition between a contracted state and an expanded state in similar fashion to device (20) described above.

Device (630) also includes a plurality of removable spacers (632) that may be attached to a link (40) connecting a bead (30) to clasping feature (602). Removable spacers (632) may be formed of any suitable material as would be apparent to one skilled in the art in view of the teachings herein. Removable spacers (632) define a pathway (636) dimensioned to slidably house link (40). Additionally, removeable spacers (632) include a snap-fit attachment feature (634) that allow spacers (632) to be selectively attached to and removed from link (40).

Removable spacers (632) may be selectively attached to and/or removed from link (40) in order to control the distance between clasping feature (602) and the adjacent bead (30). Therefore, removeable spacers (632) may be added and/or removed in order to control the contracted circumference of device (630). For example, if a surgeon desires to increase the circumference of device (630) in the contracted state, the surgeon may add spacers (632) onto link (40) as shown in FIG. 52A to achieve circumference size ($C_1$). If surgeon desires to decrease the circumference of device (630) in the contracted state, surgeon may remove spacers (632) from link (40) as shown in FIG. 53B all the way until the smallest circumference size ($C_2$) is achieved.

Removeable spacers (632) may be added before implanting device (630) within patient or removed prior to implanting device (630) within patient. In the current example, removable spacers (632) are associated with a single link (40). However, in some instances, removable spacers (632) may be associated with different links (40). Any suitable combination of spacers (632) and links (40) may be utilized as would be apparent to one skilled in the art in view of the teachings herein. In some instances, removeable spacers (632) may be configured to be placed between clasp features (602), thereby increasing the overall length of clasp features (602).

In some instances, as mentioned above, it may be desirable to passively adjust the contracted circumference of device (20) such that the contracted circumference is at least partially based on the radial forces acting on device (20) after implantation.

Figure 53A:
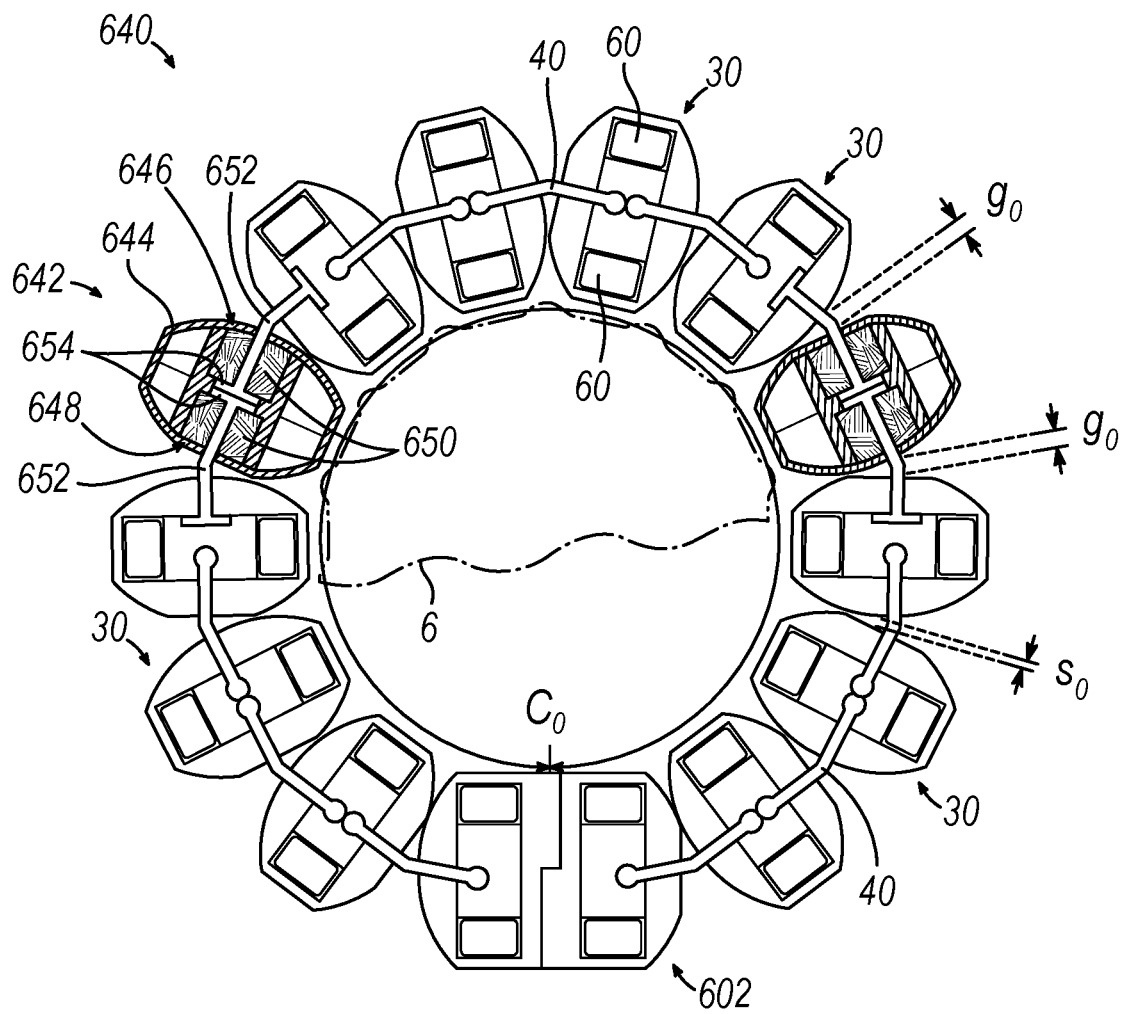
FIG. 53A depicts a cross-sectional view of an alternative sphincter augmentation device in a first circumferential size in the contracted configuration after being initially implanted into a patient.
Figure 53B:
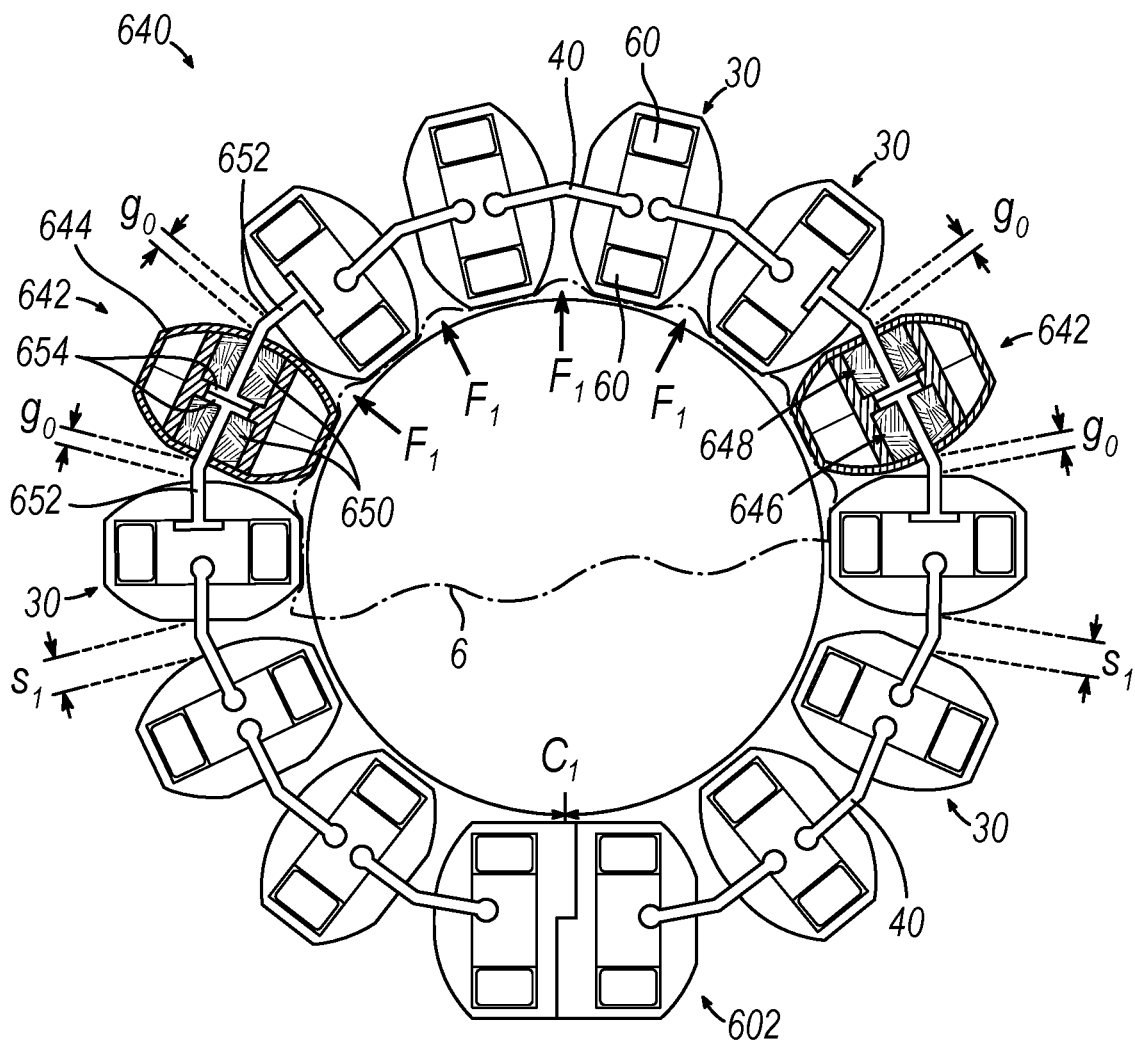
FIG. 53B depicts a cross-sectional view of the sphincter augmentation device of FIG. 53B in a second, slightly larger, circumferential size in the contracted configuration after a first period of time being implanted into the patient.
Figure 53C:
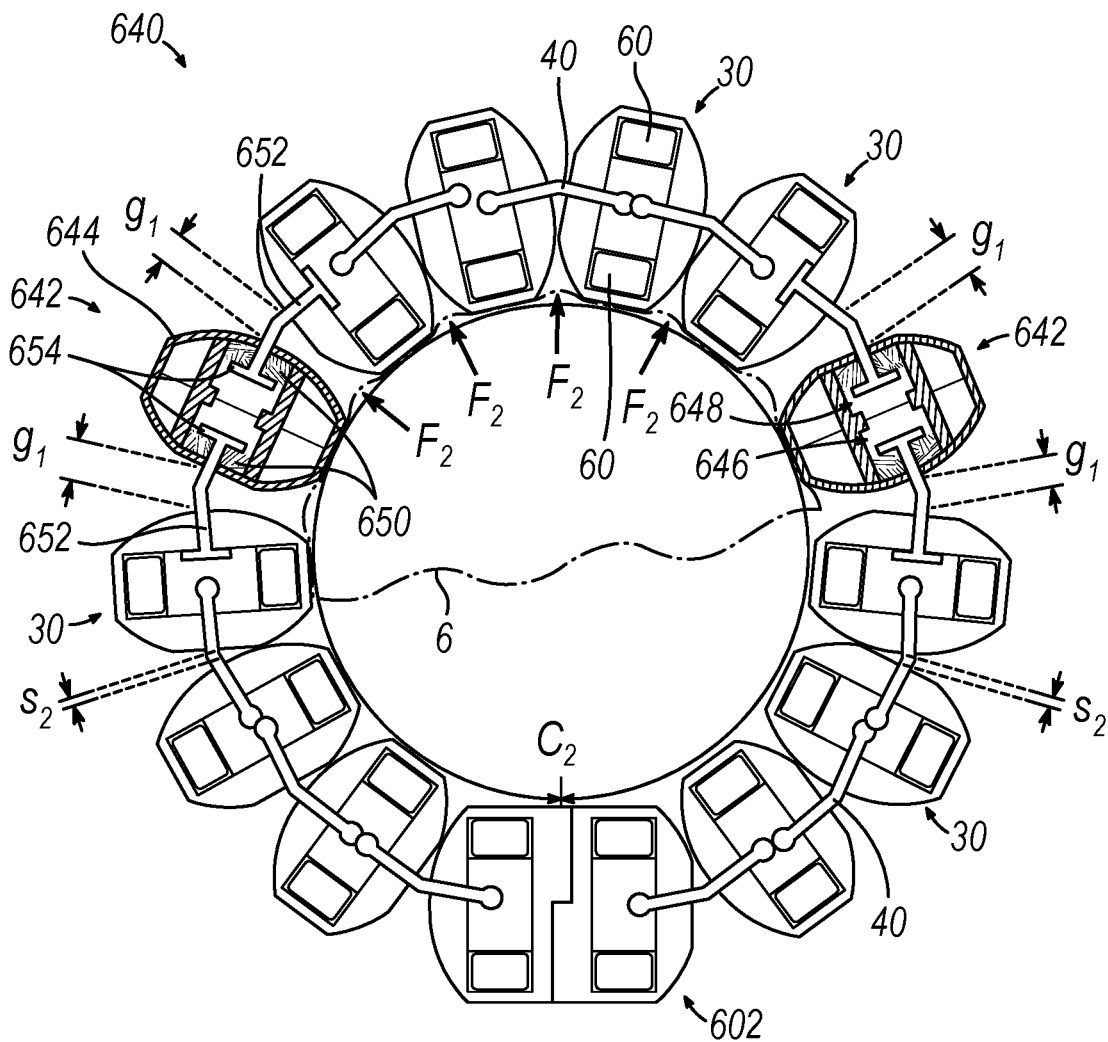
FIG. 53C depicts a cross-sectional view of the sphincter augmentation device of FIG. 53B in a third, even larger, circumferential size in the contracted configuration after a second period of time being implanted into the patient.

FIGS. 53A-53C show another exemplary alternative sphincter augmentation device (640) that may be used in replacement of sphincter augmentation device (20) described above. Therefore, device (640) may be substantially similar to device (20) described above, with differences elaborated below. Similar to device (20) described above, device (640) includes a plurality of beads (30), each housing at least one magnet (60), where beads (30) are joined together by a plurality of links (40). Device (640) also includes clasping feature (602), which may function similar to fastener features (50) to allow the ends of device (640) to be coupled together to form a loop. Device (640) is configured to transition between a contracted state and an expanded state in similar fashion to device (20) described above.

Device (640) also includes two passive length adjustment features (642). As will be described in greater detail below, in instances where device (640) has an operating circumference (in the contacted state or the expanded state) that is smaller than required for device (640) to suitably function about the targeted anatomical passageway in accordance with the description herein, passive length adjustment features (642) may allow for the circumference of device (640) to suitably lengthen as dictated by the targeted anatomical passageway. Therefore, if a patient's anatomical passageway is dimensioned with a size that requires slight adjustments, passive length adjustment features (642) may accommodate for such adjustments.

Each passive length adjustment feature (642) includes a bead housing (644) located between two adjacent beads (30). Bead housing (644) may be shaped similar to beads (30) such that bead housings (644) suitably contact adjacent beads (30) when device (640) is in the contracted state in accordance with the description herein. Bead housing (644) defines a first compression chamber (646) and a second compression chamber (648). First compression chamber (646) houses a first piece of compressible material (650); while second compression chamber (646) houses a second piece of compressible material.

Each passive length adjustment feature (642) also includes a pair of restrain plate links (652), each having a retrain plate (654) housed within a respective compression chamber (646, 648). Restrain plate links (652) extend into a respective bead (30) that is adjacent to bead housing (644). Respective beads (30) adjacent to bead housing (644) are configured to slide along the length restrain plate links (652) in order for device (640) to expand and contract in accordance with the description herein. Therefore, restrain plate links (652) function substantially the same for adjacent beads (30) as links (40).

Each restrain plate link (652) extends through a respective opening defined by bead housing (644) and into a respective compression chamber (646, 648). Each restrain plate link (652) include a restrain plate (654) contained within a respective chamber (646, 648). Restrain plates (654) abut against compressible material (650) within their respective compression chamber (646, 648) such that compressible material (650) is interposed between restrain plate (654) and the respective opening defined by bead housing (644) through which link (652) extends. Restrain plates (654) are configured to compress the adjacent compressible material (650) in response to suitably strong radial forces ($F_1$) imposed on device (640) by the surrounding anatomical passageway. Therefore, compressible material (650) is sufficiently compressible in order to compress in response to such radial forces.

FIGS. 53A-53C show an exemplary use of passive length adjustment features (642) to lengthen device (640) after device (640) is implanted to surround a desired anatomical passageway, such as LES (6). FIG. 53A shows device (640) prior to being implanted to surround the desired anatomical passageway. Therefore, as shown in FIG. 53A, there is no external radial force bearing outwardly on device (640) such that device has an initial contracted circumference ($C_0$). It should be understood that at the moment shown in FIG. 53A, since there is no external radial force bearing outward on device (640), the magnetic attraction between adjacent beads (30) may be sufficient such that the space (so) between adjacent beads (30) is substantially zero; while compressible material (650) may keep restrain plate link (652) suitably housed within chambers (646, 648) such the space ($g_0$) between bead housings (644) and adjacent beads (30) is substantially zero.

Next, as shown in FIG. 53B, device (640) may be initially implanted to surround the desired anatomical passageway. Therefore, an initial external radial force ($F_1$) may start to bear outwardly on device (640), such that the contracted circumference ($C_1$) of device starts to initially expand. At first, the compressible material (650) may remain in the same position as shown in FIG. 53A such that the space ($g_0$) between bead housings (644) and adjacent beads (30) is still substantially zero.

In some instances, the radial force ($F_1$) experienced by device (640) may be greater than preferred. As device (640) experiences the initial radial force ($F_1$) that may be greater than preferred, the magnetic attraction between adjacent beads (30) may be overcome such that adjacent beads (30) may begin to separate an initial distance ($s_1$) from each other. This separation distance ($s_1$) of adjacent bead (30) may be undesirable, as the distance between adjacent magnets (60) may be increased, which in turn may weaken the magnetic field to a lower than desired tesla value. If the resulting tesla value were to remain lower that desired, device (640) may not be able to suitably function in accordance with the description herein.

However, after a suitable period of time, as shown in FIG. 53C, the higher radial force ($F_1$) causes restrain plates (654) to compress compressible materials (650) located within chambers (646, 648). Compression of compressible materials (650) allows beads (30) directly adjacent to adjustment features (642) to separate from such features (642) a predetermined distance (gi). With directly adjacent beads (30) spaced away from such features (642), device (640) may in turn increase its contracted circumference ($C_2$), which may then allow radial force ($F_2$) imparted on device (640) to decrease compared to the previous radial force ($F_1$). As best seen in FIG. 53C, one such result of the decrease in radial force ($F_2$) is the space ($s_2$) between adjacent beads (30) may decrease and the magnetic attraction between adjacent magnetics (60) may increase back toward a desired tesla value such that device (640) may be able to suitably function in accordance with the description herein. Therefore, the passive adjustment features (642) allow device (640) to adjust its length based on the radial forces generated by a specific anatomical structure.

In some instances, compressible material (650) is configured to elastically compress, such that after large radial forces ($F_1$) are no longer present, compressible material (650) eventually returns to its original dimensions. In some other instances, compressible material (650) is configured to plastically compress, such that after large radial forces ($F_1$) are no longer present, compressible material (650) remains in its newly compressed position. Compressible material (650) may thus provide passive adjustment of the maximum diameter defined by device (640) when device (640) is in the fully expanded state. In other words, in versions where compressible material (650) is configured to plastically compress, device (640) may achieve the enlarged maximum diameter when in the fully expanded state without requiring re-compression of compressible material (650).

FIGS. 53A-53C show device (640) with two passive adjustment features (642) that are angularly spaced way from each other. However, any suitable number of adjustment features (642) may be utilized as would be apparent to one skilled in the art in view of the teachings herein. In some instances, passive adjustment features (642) and beads (30) may be organized in an alternating fashion. In some instances, passive adjustment features (642) are present after every two consecutive beads (30), or after any other suitable multiple number of magnetic beads (30) as would be apparent to one skilled in the art in view of the teachings herein.

Figure 54C:
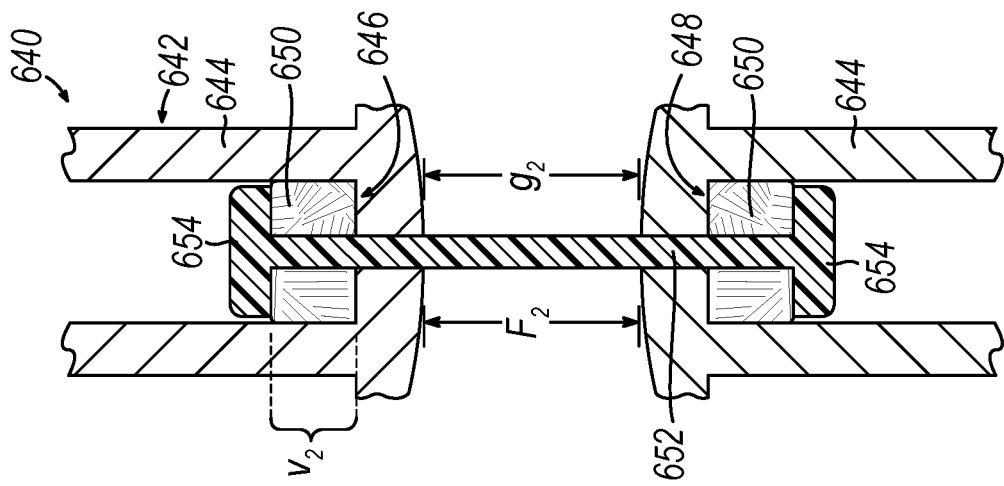
FIG. 54C depicts a cross-sectional view of the passive length adjustment feature of FIG. 54A in a position associated with the second circumferential size shown in FIG. 53C.
Figure 54B:
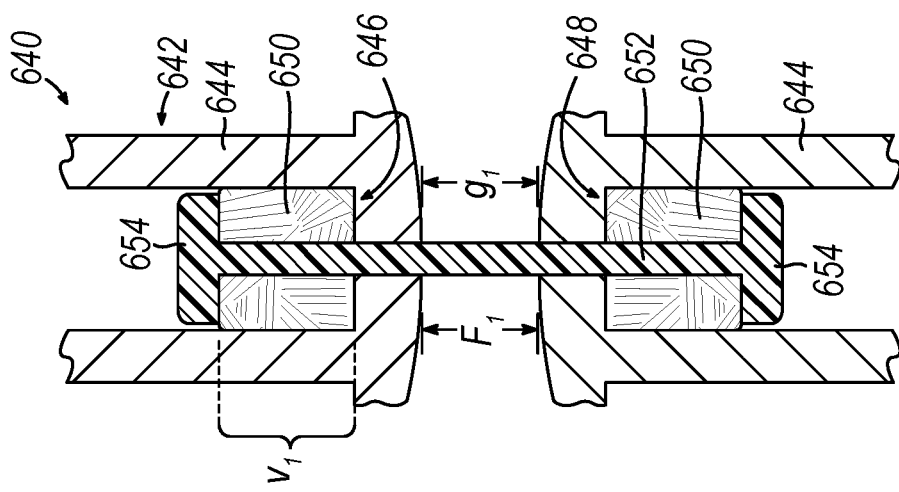
FIG. 54B depicts a cross-sectional view of the passive length adjustment feature of FIG. 54A in a position associated with the second circumferential size shown in FIG. 53B.
Figure 54A:
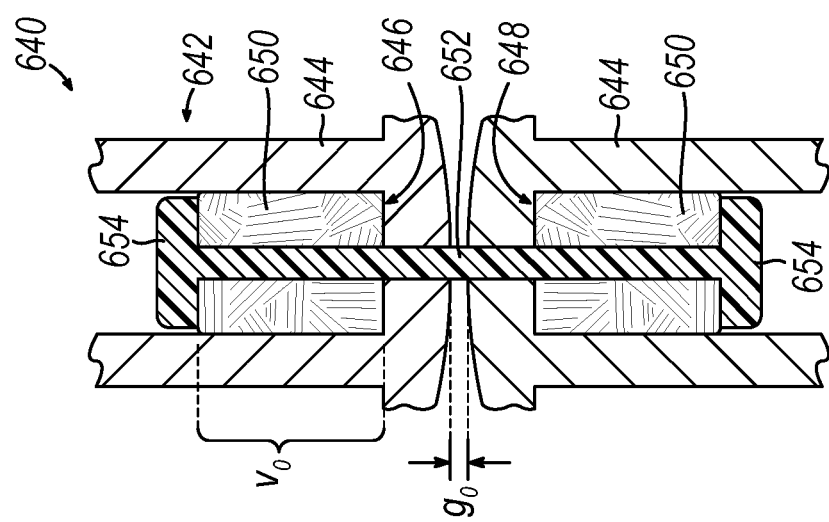
FIG. 54A depicts a cross-sectional view of a passive length adjustment feature of the sphincter augmentation device of FIG. 53A in a position associated with the first circumferential size shown in FIG. 53A.

FIGS. 54A-54C show an exemplary use of two passive length adjustment features (642) connected directly with each other. Therefore, it should be understood that the adjustment progression shown in FIGS. 54A-54C may directly correspond with the respective adjustment progression described above for FIGS. 53A-53C, but with two passive length adjustment features (642) directly adjacent to each other.

In some instances, the radial forces ($F_1$) imposed on device (640) in order to passively lengthen device (640) in accordance with the description herein may be forces naturally generated by the surrounded anatomical passageway, such as may be encountered by the patient swallowing a bolus of food or liquid. In some instances, the radial forces ($F_1$) imposed on device (640) in order to passively lengthen device (640) may be forces artificially generated within the surrounding anatomical passageway, such as a inserting a balloon within the anatomical passageway and inflating the balloon to generate said force.

Any suitable compressible material (650) may be used as would be apparent to one skilled in the art in view of the teachings herein. For example, compressible material (650) may include low density polypropylene.

Figure 55A:
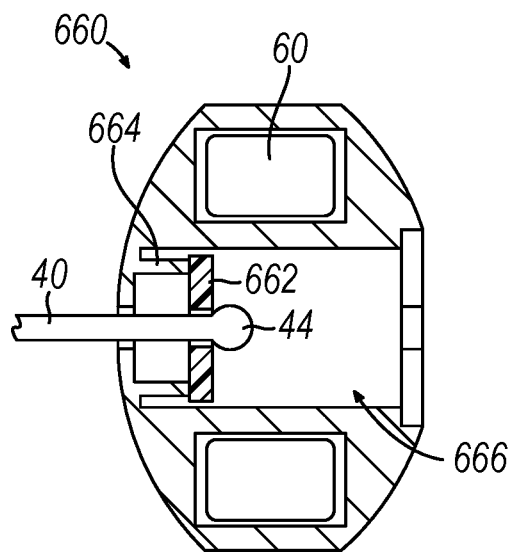
FIG. 55A depicts a cross-sectional view of another passive length adjustment feature in a first position.
Figure 55B:
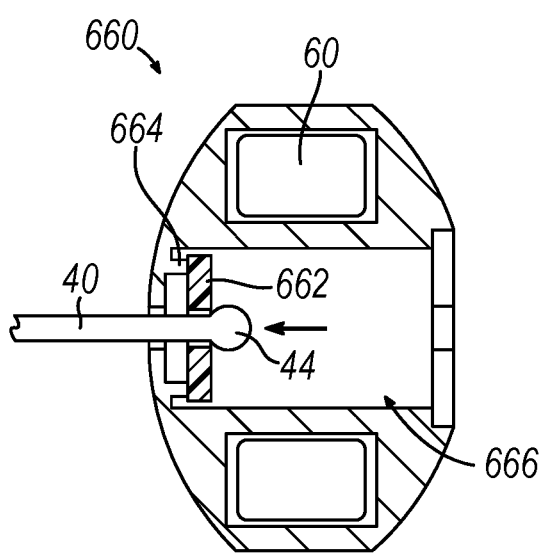
FIG. 55B depicts a cross-sectional view of the passive length adjustment feature of FIG. 55A in a second position.

In some instances, a passive length adjustment feature may be directly incorporated into a magnetic bead (30). FIGS. 55A-55B show an exemplary bead (660) that may be readily incorporated into device (640) in order to provide for passive length adjustment. Bead (660) is substantially similar to bead (30) described above, except bead (660) also has a compressible material (664) and a restraint plate (662) located within a chamber (666) that is substantially similar to chamber (36) described above. Compressible material (664) and restraint plate (662) may be substantially similar to compressible material (650) and restraint plate (654) described above, with differences elaborated below.

Compressible material (664) is interposed between plate (662) and a portion of bead (660) defining chamber (666). Restraint plate (662) is coupled to link (40) such that movement of link (40) may drive movement of plate (662). Restraint plate (662) includes a disk shape with a central opening that receives link (40). Link (40) includes ball tip (44) having an outer diameter that is larger than the inner diameter of the opening formed through plate (662) such that engagement between ball tip (44) and plate (662) may drive movement of plate (662) and thereby drive compression of compressible material (664). Therefore, when bead (660) experiences a larger than expected radial outward force, such as force ($F_1$) described above, link (40) may drive plate (662) against compressible material (664). Compressible material (664) may compress under the urging of drive plate (662), to thereby passively adjust the length of a device (640) utilizing bead (660) in accordance with the description herein. Compressible material (664) may include any suitable material and/or structure as would be apparent to one skilled in the art in view of the teachings herein. For example, compressible material (664) may be in the form of a crush rib, a wave spring, a conical washer, a coil, etc.

Figure 56A:
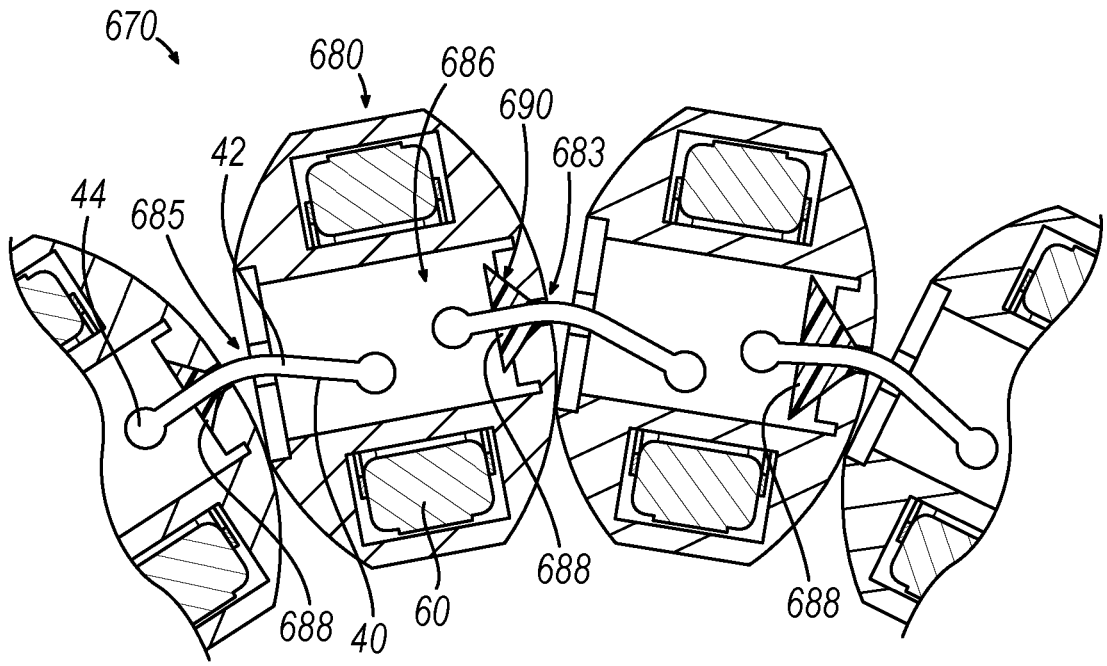
FIG. 56A depicts a cross-sectional view of an alternative sphincter augmentation device in a first circumferential size in the contracted configuration.
Figure 56B:
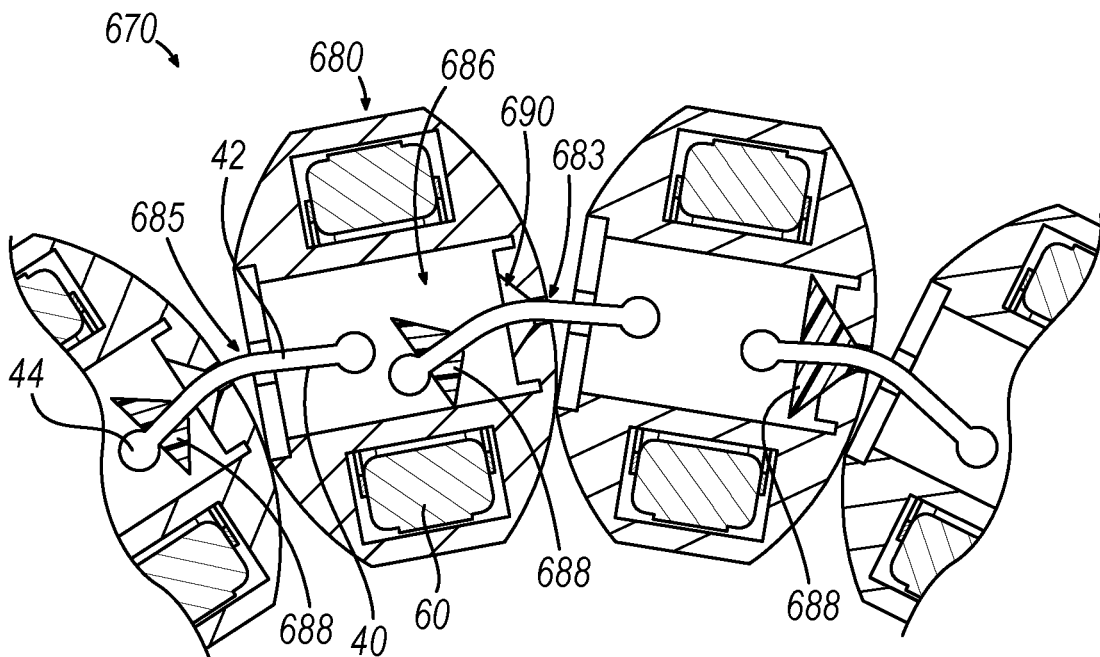
FIG. 56B depicts a cross-sectional view of the sphincter augmentation device of FIG. 56A in a second circumferential size in the contracted configuration.

FIGS. 56A-56B show another exemplary alternative sphincter augmentation device (670) that may be used in replacement of sphincter augmentation device (20) described above. Therefore, device (670) may be substantially similar to device (20) described above, with differences elaborated below. Similar to device (20) described above, device (670) includes a plurality of beads (680). Beads (680) are substantially similar to beads (30) described above, with differences elaborated below. Each bead (680) houses at least one magnet (60). Beads (680) each define a chamber (686) that extends between openings (683, 685) and that is dimensioned to slidably receive links (40). Device (640) is configured to transition between a contracted state and an expanded state in similar fashion to device (20) described above.

Device (670) includes a plurality of cone shaped bodies (688) that attach to a respective link (40). Additionally, each bead (680) in device (670) defines a complementary recess (690) dimensioned to receive a respective cone shaped body (688). Cone shape bodies (688) and recesses (690) are progressively larger along the length/circumference of device (670).

As best shown in FIG. 56A, cone shaped bodies (688) are configured to be initially fixed on link (40) and fit within a complementary recess (690) defined by bead (680). Cone shaped bodies (688) may be initially fixed to link (40) via friction fitting or any other suitable means as would be apparent to one skilled in the art in view of the teachings herein. Cone shaped bodies (688) may remain fixed to links (40) until device (670) experiences a predetermined radial force (similar to radial force ($F_1$) described above). While cone shaped bodies (688) are fixed to link (40), link (40) may only slide between respective beads (680) a predetermined length, thereby limiting the maximum diameter of device (670) in the expanded state.

As shown in FIG. 56B, once device (670) experiences a sufficient predetermined radial force, such force may overcome the frictional force between cone shaped bodies (688) and links (40), such that cone shaped bodies (688) may slide along links (40). Such movement of cone shaped bodies (688) along links (40) allows adjacent beads (680) to separate further from each other than in the state shown in FIG. 56A, which in turn increases the maximum diameter of device (670) in the expanded state. After such an enlargement, device (670) may still return to its original diameter in the contracted state. It should be noted the end of link (40) within a chamber (686) that is not attached to cone shaped body (688) may still freely slide relative to adjacent beads (680).

Device (670) may be configured such that the breakaway between links (40) and corresponding cone shaped bodies (688) occurs at predetermined beads (680) with predetermined forces. Therefore, device (670) may sequentially lengthen as the radial forces experienced by device (670) increase. Such increase in radial forces may be due to any suitable circumstances as would be apparent to one skilled in the art in view of teachings herein. For instances, if the force required to swallow increases due to scar tissue leaving a smaller diameter, device (670) may experience greater radial forces.

Figure 57A:
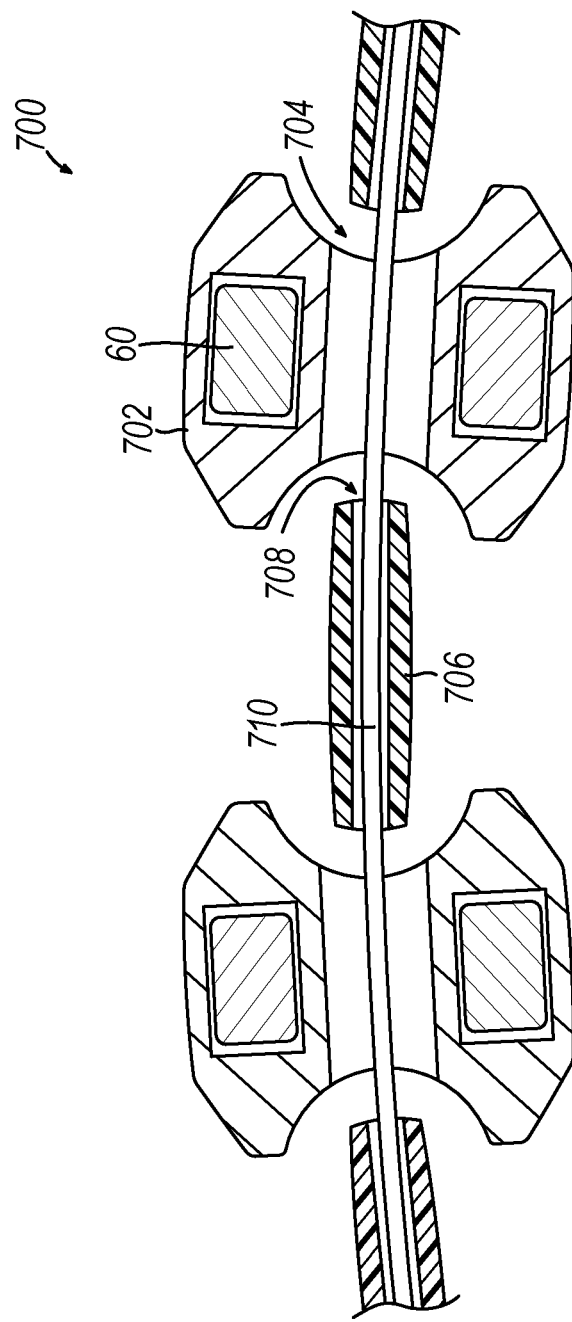
FIG. 57A depicts a cross-sectional view of an alternative sphincter augmentation device in an expanded configuration.
Figure 57B:
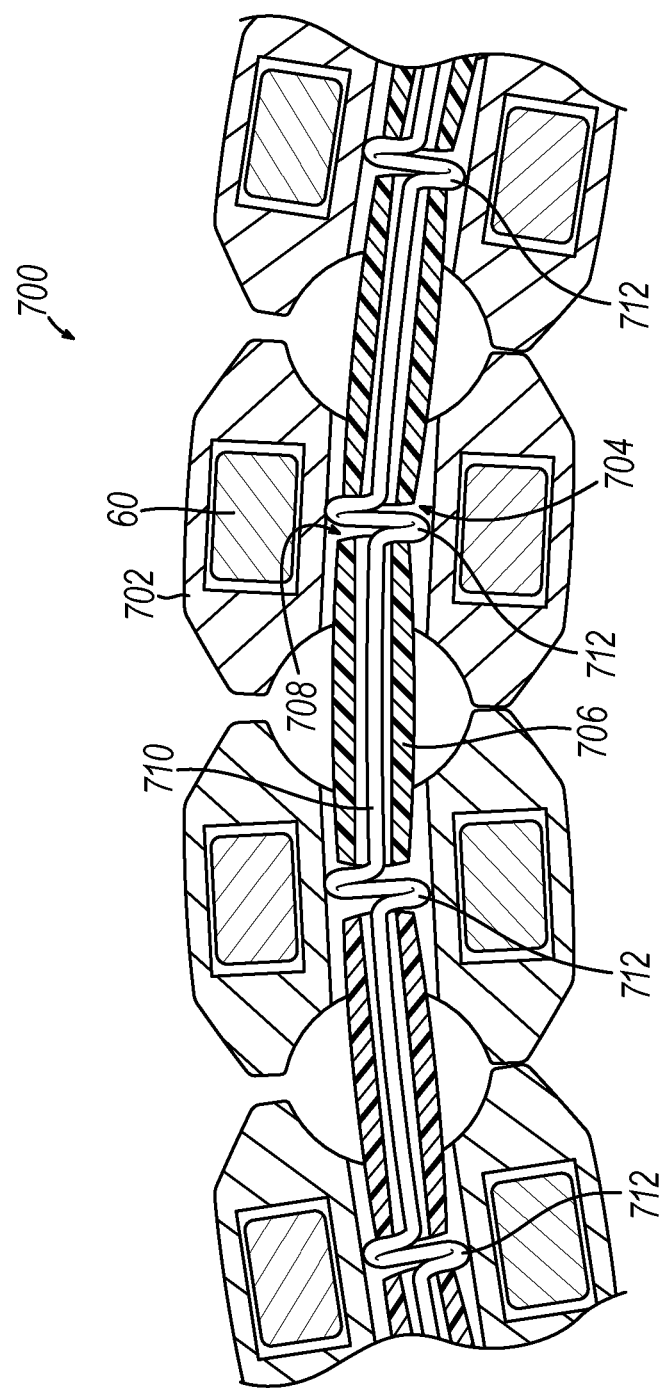
FIG. 57B depicts a cross-sectional view of the sphincter augmentation device of FIG. 57A in the contracted configuration.

FIGS. 57A-57B show another exemplary sphincter augmentation device (700) that may be used in replacement of sphincter augmentation device (20) described above. Device (700) may be substantially similar to device (20) described above, with differences elaborated below. Device (700) is configured to transition between a contracted state (see FIG. 57B) and an expanded state (see FIG. 57A) in order to assist the proper functionality of a desired anatomical structure, in a fashion similar to device (20) described above. Device (700) includes a plurality of magnetic beads (702), a plurality of rice shaped beads (706) interposed between magnetic beads (702), and an elongate braided textile (710) that extends through respective though holes (704, 708) of beads (702, 706) such that beads (702, 706) may slide along the length of elongate braided textile (710).

Magnetic beads (702) each house a respective magnet (60). Beads (702) may function substantially similar to beads (30) described above. Therefore, magnets (60) magnetically bias beads (702) and the rest of device (700) toward the contracted state (see FIG. 57B), while beads (702) may slide along elongate braided textile (710).

Rice shaped beads (706) are dimensioned to fit within through holes (704) of adjacent magnetic beads (702) in the contracted state. In particular, rice shaped beads (706) may fit within adjacent magnetic beds (702) to promote sufficient contact between the interior of magnetic bead (702) defining through hole (704) in order to resist any torsional, twisting, pivoting of adjacent magnetic beads (702), thereby promoting structural stability of device (700) in the contracted state. This may be useful in case device (700) undergoes a force that attempts to twist, bend, pivot magnetic beads (702) relative to each other. One example of such a force may be the magnetic forces generated with respect to magnets (60) when a patient having an implanted device (700) experiences an MRI field.

Elongate braided textile (710) may extend through beads (702, 706) and terminate at ends into a fastening feature, which may be similar to fastening feature (50) or clasping feature (602) described above. In some versions, elongate braided textile (710) is non-extensible. Elongate braided textile (710) may allow device (700) to form into a loop to thereby encircle an anatomical passageway. In the contracted state, elongate braided textile (710) may bunch up near adjacent rice shaped beads (706) as bunched-up regions (712) within through hole (704) defined by bead (702). It should therefore be understood that through hole (704) defined by bead (702) is suitably dimensioned with a diameter large enough to freely accommodate bunched-up regions (712) of elongate braided textile (710) when sphincter augmentation device (700) is in the contracted state. The use of elongate braided textile (710) may be beneficial in providing for an easier assembly of device (700) compared to assembling links (40) of device (20). Additionally, elongate braided textile (710) may be beneficial since braided textile material may inhibit fatigue from cyclical expansion and retraction in accordance with the description herein.

In some instances, it may be desirable to provide a passive change in circumference of device (20) by changing the length of links (40). Link (40) may be formed of a liquid crystal polymer and nylon weave. Having link (40) formed of a liquid crystal polymer and nylon weave may promote plastic deformation of link (40) during exemplary use. Therefore, device (20) may stretch out, and remained stretched out, if placed under suitable outward stress. In other words, the circumference of device (20) may be adjusted over time via changes in the length of link (40) based on the radial force acting on device (20).

In some instances, such as those where a device (20) does not achieve a small enough diameter in the contracted state in order to effectively restrict the targeted anatomical structure, it may be desirable to provide a passive change in the minimum circumference of device (20) via the contact surfaces of beads (30) while in the contracted state. For example, it may be desirable to provide a malleable material at the contact surfaces on beads (30) (i.e., the surfaces that abut against adjacent beads (30) in the contracted state). If a device (20) has too large of a minimum circumference such that device (20) does not suitably engage the desired anatomical structure, the malleable material on the contact surfaces of beads (30) may eventually deform in response to the bearing forces of adjacent beads (30) caused by magnetic attraction between the adjacent beads (30). Such deformation of the malleable material may eventually allow for device (20) to eventually achieve a smaller minimum circumference in the contracted state to thereby suitably restrict flow through the targeted anatomical structure.

X. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a plurality of beads, wherein each bead in the plurality of beads defines a first opening and a second opening; (b) a linking assembly extending through the first opening and the second opening of each bead in the plurality of beads, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; and (c) a 3D printed magnetic element housed within a first bead of the plurality of beads, wherein the 3D printed magnetic element comprises a composite of magnetic granules combined together to generate a magnetic field, wherein the magnetic field generated by the 3D printed magnetic element is configured to contribute to the magnetic bias of the plurality of beads.

Example 2

The apparatus of any one or more of the preceding Examples, further comprising a second 3D printed magnetic element housed within the first bead such that the first 3D printed magnetic element and the second 3D printed magnetic elements are stacked together.

Example 3

The apparatus of any one or more of the preceding Examples, further comprising a second 3D printed magnetic element housed within a second bead of the plurality of beads.

Example 4

The apparatus of any one or more of the preceding Examples, wherein the 3D printed magnetic element comprises a constant cross-sectional geometry.

Example 5

The apparatus of any one or more of the preceding Examples, wherein the 3D printed magnetic element comprises a varying cross-sectional geometry.

Example 6

The apparatus of any one or more of the preceding Examples, wherein the 3D printed magnetic element comprises a first portion having a first density and a second portion having a second density, wherein the first density and the second density are different.

Example 7

The apparatus of any one or more of the preceding Examples, wherein the first portion comprises a first material and the second portion comprises a second material.

Example 8

The apparatus of any one or more of the preceding Examples, wherein the first material comprises a first magnetic material, wherein the second material comprises a second magnetic material.

Example 9

The apparatus of any one or more of the preceding Examples, wherein the first material comprises a magnetic material, wherein the second material comprises a non-magnetic material.

Example 10

The apparatus of any one or more of the preceding Examples, wherein the second material encapsulates the first material.

Example 11

The apparatus of any one or more of the preceding Examples, wherein the 3D printed magnetic element defines a hollow pocket.

Example 12

The apparatus of any one or more of the preceding Examples, wherein the hollow pocket extends annularly within the 3D printed magnetic element.

Example 13

The apparatus of any one or more of the preceding Examples, wherein the 3D printed magnetic element defines a second hollow pocket.

Example 14

The apparatus of any one or more of the preceding Examples, wherein the 3D printed magnetic element comprises an annular shape.

Example 15

The apparatus of any one or more of the preceding Examples, wherein the linking assembly comprises a plurality of links joining the beads together, wherein portions of the links are slidably disposed in a corresponding passageway of the beads such that the plurality of beads is operable to transition between the constricted configuration and the expanded configuration.

Example 16

The apparatus of any one or more of the preceding Examples, wherein each bead of the plurality of beads comprises a magnetically inert housing.

Example 17

An apparatus comprising: (a) a plurality of beads, wherein each bead in the plurality of beads defines: (i) a first opening, (ii) a second opening, and (iii) a chamber; (b) a linking assembly extending through the first opening and the second opening of each bead in the plurality of beads, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; and (c) a magnetic element housed in the chamber of a first bead of the plurality of beads, wherein the magnetic element comprises an orientation feature configured to mate with a complementary orientation feature of the first bead to thereby restrict movement of the magnetic element within the chamber of the first bead, wherein the magnetic element is configured to contribute to the magnetic bias of the beads.

Example 18

The apparatus of any one or more of the preceding Examples, wherein the orientation feature of the magnetic element comprises a 3D printed orientation body, wherein the complementary orientation feature comprises an orientation slot.

Example 19

The apparatus of any one or more of the preceding Examples, wherein the orientation feature comprises a slot, wherein the complementary orientation feature comprises a 3D printed body.

Example 20

An apparatus comprising: (a) a plurality of beads, wherein each bead in the plurality of beads defines: (i) a first opening, (ii) a second opening, and (iii) a chamber isolated from the first opening and the second opening; (b) a linking assembly extending through the first opening and the second opening of each bead in the plurality of beads, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; and (c) a magnetic element housed in a first bead of the plurality of beads within the chamber of the first bead, wherein the magnetic element comprises a first annular body and a 3D printed magnetic body fixed to the first annular body, wherein the first annular body and the 3D printed magnetic body are configured to cooperate to contribute to the magnetic bias of the plurality of beads.

Example 21

An apparatus comprising: (a) a plurality of beads, wherein each bead in the plurality of beads includes: (i) at least one magnet, and (ii) a housing encasing and sealing the at least one magnet, the unibody housing comprising a magnetically inert metallic material, the magnetically inert metallic material being formed of a particulate powder composition; and (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 22

The apparatus of any one or more of the preceding Examples, each unibody housing defining a first opening and a second opening, the linking assembly being disposed through the first opening and the second opening of the unibody housings.

Example 23

The apparatus of any one or more of the preceding Examples, the linking assembly comprising a plurality of links, each bead of the plurality of beads being coupled with two links of the plurality of links.

Example 24

The apparatus of any one or more of the preceding Examples, wherein the housing has a unibody construction.

Example 25

The apparatus of any one or more of the preceding Examples, wherein the housing comprises: (A) a first piece comprising a first annular flange, and (B) a second piece comprising a second annular flange abutting against the first annular flange, wherein the first piece and the second piece together define a magnet chamber, the at least one magnet being housed in the magnet chamber.

Example 26

The apparatus of any one or more of the preceding Examples, wherein the housing further comprises a circumferential weld located at the first annular flange and the second annular flange to form a hermetic seal with the magnet chamber, wherein the first annular flange and the second annular flange are configured to define a circumferential groove extending circumferentially around the housing to receive a weld bead of the circumferential weld.

Example 27

The apparatus of any one or more of the preceding Examples, wherein the first annular flange comprises a first slanted surface at least partially defining the circumferential groove.

Example 28

The apparatus of any one or more of the preceding Examples, wherein the second annular flange comprises a second slanted surface defining the circumferential groove with the first slanted surface.

Example 29

The apparatus of any one or more of the preceding Examples, wherein the second annular flange comprises a square surface defining the circumferential groove with the first slanted surface.

Example 30

The apparatus of any one or more of the preceding Examples, wherein the second annular flange comprises a convex surface defining the circumferential groove with the first slanted surface.

Example 31

The apparatus of any one or more of the preceding Examples, wherein the first annular flange comprises a concave surface at least partially defining the circumferential groove.

Example 32

The apparatus of any one or more of the preceding Examples, wherein the second annular flange comprises a second concave surface defining the circumferential groove with the concave surface of the first annular flange.

Example 33

The apparatus of any one or more of the preceding Examples, wherein the second annular flange comprises a square surface defining the circumferential groove with the concave surface of the first annular flange.

Example 34

The apparatus of any one or more of the preceding Examples, wherein the first annular flange and the second annular flange both project inwardly into the magnet chamber.

Example 35

The apparatus of any one or more of the preceding Examples, wherein the first annular flange comprises a first resilient latch, wherein the second annular flange comprises a second resilient latch, wherein the first resilient latch and the second resilient latch are configured to couple together in order to temporarily inhibit movement of the first piece relative to the second piece.

Example 36

The apparatus of any one or more of the preceding Examples, wherein each bead defines the first opening, wherein the first opening comprises a pair of contact surfaces converging into a targeted contact location configured to guide movement of the linking assembly relative to the housing as the loop transitions between the contracted configuration and the expanded configuration.

Example 37

An apparatus comprising: (a) a plurality of beads, wherein each bead comprises: (i) a housing comprising: (A) a first piece comprising a first latching member, and (B) a second piece comprising a second latching member configured to engage the first latching member to couple the first piece with the second piece, wherein the first latching member and the second latching member define an annular groove extending circumferentially around the housing, wherein the first piece and the second piece together define a magnet chamber, (ii) at least one magnet disposed within the magnet chamber, and (iii) a circumferential weld located at the annular groove to hermetically seal the magnet chamber, wherein the annular groove is configured to receive a weld bead of the circumferential weld; and (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 38

A method comprising: (a) using a magnetically inert particulate powder composition to form a plurality of housings, each housing defining a magnet chamber; (b) positioning one or more magnets in each magnet chamber; (c) hermetically sealing the one or more magnets in each magnet chamber, each housing and hermetically sealed one or more magnets defining a bead; and (d) joining the beads together with a linking assembly, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 39

The method of any one or more of the preceding Examples, the act of using a magnetically inert particulate powder composition to form a plurality of housings comprising one or more processes selected from the group consisting of 3D printing, metal injection molding, or powder metallurgy.

Example 40

The method of any one or more of the preceding Examples, the act of hermetically sealing the one or more magnets in each magnet chamber comprising welding.

Example 41

An apparatus comprising: (a) a plurality of beads, each bead comprising: (i) a housing comprising: (A) a first piece, and (B) a second piece, wherein the first piece and the second piece together define a magnet chamber, (ii) at least one magnet disposed within the magnet chamber, and (iii) a weld joining the first piece and the second piece together, the weld hermetically sealing the magnet chamber, the weld extending along a weld plane, the first piece of the housing further including a mounting feature integrated with a surface of the first piece, wherein the mounting feature is configured to mate with a fixture to constrain the first piece of the housing as the weld is formed; and (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 42

The apparatus of any one or more of the preceding Examples, the first piece comprising a first annular rim, the second piece comprising a second annular rim engaged with the first annular rim, the weld comprising a circumferential weld located at the first annular rim and the second annular rim.

Example 43

The apparatus of any one or more of the preceding Examples, the mounting feature comprising a plurality of recesses defined by an external surface of the first piece.

Example 44

The apparatus of any one or more of the preceding Examples, wherein the fixture comprises a plurality of complementary projections configured to engage the plurality of recesses defined by the external surface of the first piece.

Example 45

The apparatus of any one or more of the preceding Examples, wherein the external surface extends along a plane that is parallel to the weld plane.

Example 46

The apparatus of any one or more of the preceding Examples, wherein the mounting feature is configured to rotationally constrain the first piece relative to the fixture as the weld is formed.

Example 47

The apparatus of any one or more of the preceding Examples, wherein the fixture comprises a complementary surface at least partially defining a housing recess configured to engage an external surface of the first piece adjacent to the mounting feature.

Example 48

The apparatus of any one or more of the preceding Examples, wherein the second piece further comprises a second mounting feature integrated with a surface of the second piece, wherein the second mounting feature is configured to mate with a second fixture to constrain the second piece of the housing as the weld is formed.

Example 49

The apparatus of any one or more of the preceding Examples, wherein the second mounting feature is configured to rotationally constrain the second piece of the housing as the weld is formed.

Example 50

The apparatus of any one or more of the preceding Examples, the mounting feature comprising at least one projection extending outwardly from the surface of the first piece.

Example 51

The apparatus of any one or more of the preceding Examples, the at least one projection comprising a ledge.

Example 52

The apparatus of any one or more of the preceding Examples, the mounting feature comprising at least one dimple formed in the surface of the first piece.

Example 53

The apparatus of any one or more of the preceding Examples, wherein the linking assembly comprises plurality of links joining the beads together, wherein portions of the links are slidably disposed in corresponding beads of the plurality of beads such that the beads are slidable along the links as the loop moves between the contracted configuration and the expanded configuration.

Example 54

The apparatus of any one or more of the preceding Examples, wherein each bead further defines a passageway passing through the first piece and the second piece.

Example 55

The apparatus of any one or more of the preceding Examples, the at least one magnet encircling the passageway.

Example 56

An apparatus comprising: (a) a plurality of beads, each bead comprising: (i) a housing comprising: (A) a first piece comprising a first annular rim, and (B) a second piece comprising a second annular rim configured to engage the first annular rim, wherein the first piece and the second piece together define a magnet chamber, (ii) at least one magnet disposed within the magnet chamber, and (iii) a circumferential weld joining the first piece and the second piece together, the circumferential weld hermetically sealing the magnet chamber, the weld extending along a weld plane, (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; and (c) a mounting plate interface assembly integrally formed with the first piece of the housing, wherein the mounting plate interface assembly is configured to configured to mate with a mounting plate to constrain the first piece of the housing as the weld is formed, the mounting plate interface being parallel with the weld plane.

Example 57

A method comprising: (a) positioning a first bead housing piece in a first mounting fixture, the first bead housing piece and the first mounting fixture comprising complementary alignment features, the act of positioning the first bead housing piece in the first mounting fixture comprising engaging the complementary alignment features of the first bead housing and the first mounting fixture with each other, the engagement of the complementary alignment features of the first bead housing and the first mounting fixture with each other providing a predetermined alignment between the first bead housing piece and the first mounting fixture; (b) positioning at least one magnet relative to the first bead housing piece; (c) positioning a second bead housing piece relative to the at least one magnet and the first bead housing piece; (d) securing the first bead housing piece and the second bead housing piece together, thereby enclosing the at least one magnet in a chamber defined by the first bead housing piece and the second bead housing piece, the first bead housing piece, the second bead housing piece, and the at least one magnet together defining a plurality of beads; (e) repeating steps (a) through (d) to form a plurality of beads; and (f) joining the beads together via a linking assembly.

Example 58

The method of any one or more of the preceding Examples, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 59

The method of any one or more of the preceding Examples, the act of positioning a second bead housing piece relative to the at least one magnet and the first bead housing piece further comprising positioning the second bead housing piece in a second mounting fixture, the second bead housing piece and the second mounting fixture comprising complementary alignment features, the act of positioning the second bead housing piece in the second mounting fixture comprising engaging the complementary alignment features of the second bead housing and the second mounting fixture with each other, the engagement of the complementary alignment features of the second bead housing and the second mounting fixture with each other providing a predetermined alignment between the second bead housing piece and the second mounting fixture.

Example 60

The method of any one or more of the preceding Examples, the act of securing the first bead housing piece and the second bead housing piece together comprising welding the first bead housing piece and the second bead housing piece together.

Example 61

A method of manufacturing a bead assembly for a sphincter augmentation device, the method comprising: (a) initiating 3D printing of a unibody housing such that the unibody housing defines a first opening, a first chamber and a magnet chamber; (b) pausing the 3D printing of the unibody housing; (c) inserting a magnet within the magnet chamber defined by the unibody housing; and (d) resuming 3D printing of the unibody housing to thereby form a hermetic seal between the magnet chamber and an external surface of the unibody housing.

Example 62

The method of any one or more of the preceding Examples, further comprising applying a layer of a second material on an interior surface defining the magnet chamber.

Example 63

The method of any one or more of the preceding Examples, wherein applying the layer of the second material further comprises 3D printing the second material.

Example 64

The method of any one or more of the preceding Examples, wherein 3D printing the second material further comprises 3D printing an annular surface with the second material.

Example 65

The method of any one or more of the preceding Examples, wherein the second material comprises an epoxy material.

Example 66

The method of any one or more of the preceding Examples, wherein the epoxy material comprises an epoxy resin.

Example 67

The method of any one or more of the preceding Examples, wherein resuming 3D printing of the unibody housing comprises 3D printing a unibody housing such that the unibody housing defines a second opening in communication with the first chamber and the first opening.

Example 68

The method of any one or more of the preceding Examples, wherein initiating 3D printing of the unibody housing further comprises 3D printing the unibody housing as to define an open end of the magnet chamber.

Example 69

The method of any one or more of the preceding Examples, wherein inserting the magnet within the magnet chamber further comprises inserting the magnet through the open end of the magnet chamber.

Example 70

The method of any one or more of the preceding Examples, wherein the magnet chamber further comprises an orientation feature, wherein the magnet comprises a complementary orientation feature, wherein inserting the magnet within the magnet chamber further comprises inserting the orientation feature within the complementary orientation feature.

Example 71

The method of any one or more of the preceding Examples, wherein the unibody housing is formed with titanium.

Example 72

The method of any one or more of the preceding Examples, wherein pausing the 3D printing of the unibody housing occurs prior to inserting the magnet within the magnetic chamber.

Example 73

The method of any one or more of the preceding Examples, wherein inserting the magnet into the magnet chamber comprises inserting an annular magnet within the magnet chamber.

Example 74

The method of any one or more of the preceding Examples, wherein interesting the magnet within the magnet chamber comprises inserting a 3D printed magnet into the magnet chamber.

Example 75

The method of any one or more of the preceding Examples, further comprising: (e) repeating steps (a) through (d) to form a plurality of bead assemblies; and (f) joining the plurality of bead assemblies together via a linking assembly, wherein the bead assemblies and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the bead assemblies.

Example 76

A method of manufacturing a bead assembly for a sphincter augmentation device, the method comprising: (a) initiating 3D printing of a unibody housing by 3D printing a titanium material to define a first opening and partially define a first chamber and a magnet chamber; (b) pausing the 3D printing of the unibody housing; (c) inserting a magnet into the magnet chamber defined by the unibody housing such that the magnet rests on a surface defining the magnet chamber; and (d) resuming 3D printing of the unibody housing by 3D printing the titanium material to thereby form a hermetic seal between the magnet chamber and the first chamber of the unibody housing.

Example 77

The method of any one or more of the preceding Examples, further comprising inserting an epoxy material into the magnet chamber prior to inserting the magnet within the magnet chamber.

Example 78

The method of any one or more of the preceding Examples, wherein inserting the magnet into the magnet chamber further comprises inserting the magnet against the epoxy material.

Example 79

The method of any one or more of the preceding Examples, wherein the epoxy material forms an annular surface, wherein inserting the magnet into the magnet chamber further comprise inserting the magnet against the annular surface.

Example 80

A method of manufacturing a bead assembly for a sphincter augmentation device, the method comprising: (a) initiating 3D printing of a unibody housing such that the unibody housing defines a first opening, a first chamber, and a magnet chamber; (b) inserting a magnet within the magnet chamber defined by the unibody housing; and (c) resuming 3D printing of the unibody housing to define a second opening in communication with the first chamber and the first opening and also form a hermetic seal between the magnet chamber and an external surface of the unibody housing.

Example 81

An apparatus comprising: (a) a plurality of beads, wherein each bead of the plurality of beads comprises: (i) a housing defining a magnet chamber, and (ii) a magnet assembly disposed within the magnet chamber, wherein the magnet assembly comprises: (A) at least one annular magnet, and (B) an encasement surrounding the at least one annular magnet to provide a seal between the at least one annular magnet and the magnet chamber; and (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 82

The apparatus of any one or more of the preceding Examples, wherein the at least one annular magnet comprises a plurality of annular magnets stacked together.

Example 83

The apparatus of any one or more of the preceding Examples, wherein the encasement is configured to inhibit movement of individual annular magnets of the plurality of annular magnets relative to each other.

Example 84

The apparatus of any one or more of the preceding Examples, wherein the encasement structurally supports the plurality of annular magnets such that individual annular magnets of the plurality of annular magnets are fixed relative to each other.

Example 85

The apparatus of any one or more of the preceding Examples, wherein the encasement extends between adjacent annular magnets of the plurality of annular magnets such that the encasement is interposed between adjacent annular magnets that are stacked together.

Example 86

The apparatus of any one or more of the preceding Examples, wherein the encasement comprises a first section associated with a first magnetic pole of the at least one annular magnet, wherein the first section comprises a first identification feature.

Example 87

The apparatus of any one or more of the preceding Examples, wherein the encasement further comprises a second section associated with a second magnetic pole of the at least one annular magnet, wherein the second section comprises a second identification feature.

Example 88

The apparatus of any one or more of the preceding Examples, wherein the encasement comprises a plastic material.

Example 89

The apparatus of any one or more of the preceding Examples, wherein the encasement comprises polyether ether ketone.

Example 90

The apparatus of any one or more of the preceding Examples, wherein the encasement comprises an ultra-high molecular-weight polyethylene material.

Example 91

The apparatus of any one or more of the preceding Examples, wherein the encasement comprises a retaining feature configured to inhibit the magnet assembly from moving relative to the magnet chamber in a first direction.

Example 92

The apparatus of any one or more of the preceding Examples, wherein the encasement further comprises a base layer, wherein the retaining feature extends away from the base layer.

Example 93

The apparatus of any one or more of the preceding Examples, wherein the retaining feature is thicker than the base layer.

Example 94

The apparatus of any one or more of the preceding Examples, wherein the encasement comprises a second retaining feature configured to inhibit the magnet assembly from rotating within the magnet chamber.

Example 95

The apparatus of any one or more of the preceding Examples, wherein the encasement comprises an epoxy material.

Example 96

An apparatus comprising: (a) a plurality of beads, wherein at least one bead of the plurality of beads comprises: (i) a housing defining a magnet chamber, and (ii) a magnet assembly disposed within the magnet chamber, wherein the magnet assembly comprises: (A) a plurality of annular magnets stacked together to thereby define a central opening, and (B) an encasement covering the plurality of annular magnets, wherein the encasement is configured to inhibit movement of individual annular magnets of the plurality of annular magnets relative to each other; and (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 97

The apparatus of any one or more of the preceding Examples, wherein the encasement is configured to seal the plurality of annular magnets from an external environment.

Example 98

The apparatus of any one or more of the preceding Examples, wherein the encasement comprises at least one of the following: an injection molded material, a compression molded material, or a vacuum molded material.

Example 99

The apparatus of any one or more of the preceding Examples, wherein the linking assembly comprises at least one metal wire interposed between a first bead of the plurality of beads and a second bead of the plurality of beads.

Example 100

An apparatus comprising: (a) a plurality of beads, wherein at least one bead of the plurality of beads comprises: (i) a housing defining a magnet chamber, and (ii) a magnet assembly disposed within the magnet chamber, wherein the magnet assembly comprises: (A) a stack of magnets within the magnet chamber, and (B) an encasement molding covering the stack of magnets, wherein the encasement molding is configured to inhibit movement of individual magnets of the stack of magnets relative to each other, wherein the encasement molding surrounds the stack of magnets to provide a seal between the stack of magnets and the magnet chamber; and (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

Example 101

An apparatus comprising: (a) a plurality of beads, each bead comprising: (i) a housing defining a first opening, a second opening, and a chamber extending between the first opening and the second opening, and (ii) a magnet assembly contained within the housing; (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads, wherein the linking assembly comprises a link element coupling a first bead of the plurality of beads and a second bead of the plurality of beads, wherein the link element comprises: (i) an elongate coupling body extending within the first opening of the first bead and the second opening of the second bead, and (ii) a first sealing assembly associated with the elongate coupling body and attached to the first opening of the first bead such that the first sealing element is configured to form a seal between the chamber and an exterior of the housing of the first bead.

Example 102

The apparatus of any one or more of the preceding Examples, wherein the first sealing assembly comprises a sealing end cap.

Example 103

The apparatus of any one or more of the preceding Examples, wherein the sealing end cap comprises a thermoform material or an expandable shape memory material.

Example 104

The apparatus of any one or more of the preceding Examples, wherein the sealing end cap comprises a finned shape member plug or an expanding torque plug.

Example 105

The apparatus of any one or more of the preceding Examples, wherein the sealing end cap comprises a sealing flange formed on an interior of the first bead.

Example 106

The apparatus of any one or more of the preceding Examples, wherein a portion of the first bead defining the first opening also defines an annular sealing recess, wherein at least a portion of the sealing end cap is housed within the annular sealing recess.

Example 107

The apparatus of any one or more of the preceding Examples, wherein the sealing end cap is configured to form the seal in response to exposure to a heat source.

Example 108

The apparatus of any one or more of the preceding Examples, wherein the sealing end cap is configured to form the seal in response to exposure to a vacuum source.

Example 109

The apparatus of any one or more of the preceding Examples, wherein the seal formed from the first sealing assembly comprises a hermetic seal.

Example 110

The apparatus of any one or more of the preceding Examples, wherein the link element comprises a second sealing assembly associated with the elongate coupling body and attached to the second opening of the second bead such that the second sealing element is configured to form a second seal between the chamber and an exterior of the housing of the second bead.

Example 111

The apparatus of any one or more of the preceding Examples, wherein the elongate coupling body comprises a woven stranded cable.

Example 112

The apparatus of any one or more of the preceding Examples, wherein the woven stranded cable is configured to slide relative to the first sealing assembly.

Example 113

The apparatus of any one or more of the preceding Examples, wherein the woven stranded cable is configured to deform as the plurality of beads transition into the contracted configuration.

Example 114

The apparatus of any one or more of the preceding Examples, wherein the first sealing assembly comprises a snap-fit sealing end cap.

Example 115

The apparatus of any one or more of the preceding Examples, wherein the snap-fit sealing end cap comprises a compression cap dimensioned to form a snap-fit seal with the first opening.

Example 116

An apparatus comprising: (a) a plurality of beads, each bead comprising: (i) a housing defining a first opening, a second opening, and a chamber extending between the first opening and the second opening, and (ii) a magnet assembly contained within the chamber of the housing, (b) a linking assembly coupling the plurality of beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads, wherein the linking assembly comprises a link coupling a first bead of the plurality of beads and a second bead of the plurality of beads, wherein the link comprises: (i) a woven stranded cable extending within the first opening of the first bead and the second opening of the second bead, and (ii) a first sealing element associated with the woven stranded cable, wherein the first sealing element is housed within the first opening of the first bead such that the first sealing element is configured to provide a hermetic seal between the chamber and an exterior of the housing of the first bead.

Example 117

The apparatus of any one or more of the preceding Examples, wherein the first sealing element is configured to expand against a portion of the first bead defining the first opening in order to form the hermetic seal.

Example 118

The apparatus of any one or more of the preceding Examples, wherein the woven stranded cable comprises a portion fixed to the first sealing element.

Example 119

The apparatus of any one or more of the preceding Examples, wherein the link comprises a second sealing element located within the second opening of the second bead, wherein the second sealing element is configured to provide a second hermetic seal between the chamber and the exterior of the housing of the second bead.

Example 120

An apparatus comprising: (a) a plurality of beads, each bead comprising: (i) a housing defining a first opening, a second opening, and a chamber extending between the first opening and the second opening, and (ii) a magnet assembly contained within the housing, (b) a linking assembly coupling the plurality of beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads, wherein the linking assembly comprises a first link element extending within the first opening of a first bead of the plurality of beads, wherein the first link element comprises: (i) an elongate body extending into the chamber of the first bead, and (ii) a sealing element attached to the elongate body and housed within the first opening of the first bead to thereby form a hermetic seal.

Example 121

An apparatus comprising: (a) a plurality of beads comprising: (i) a first bead, wherein the first bead comprises a first housing and a first external contact surface, wherein the first bead defines a first through hole, and (ii) a second bead located adjacent to the first bead, wherein the second bead comprises a second housing and a second external contact surface, wherein the second bead defines a second through hole; and (b) a linking assembly coupling the plurality of beads together, wherein the linking assembly extends within the first through hole of the first bead and the second through hole of the second bead to thereby couple the first bead with the second bead; wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; wherein the first external contact surface and the second external contact surface are configured to engage each other as the loop transitions into the contracted configuration to thereby drive the first bead and the second bead into a predetermined orientation relative to each other about the linking assembly in the contracted configuration Example 122

The apparatus of any one or more of the preceding Examples, wherein the first external contact surface is configured to nest with the second external contact surface to thereby drive the first bead and the second bead into the predetermined orientation.

Example 123

The apparatus of any one or more of the preceding Examples, wherein the first external contact surface comprises a concave profile along a dimension transverse to the linking assembly, wherein the second external contact surface comprises a convex profile along a dimension transverse to the linking assembly.

Example 124

The apparatus of any one or more of the preceding Examples, wherein the convex profile of the second external contact surface is configured to nest with the concave profile of the first external surface while the loop is in the contracted configuration.

Example 125

The apparatus of any one or more of the preceding Examples, wherein the first external contact surface and the second external contact surface are configured to engage each other to inhibit the first bead and the second bead from slipping relative to each other in a direction transverse to the linking assembly while the loop is in the contracted configuration.

Example 126

The apparatus of any one or more of the preceding Examples, wherein the first external contact surface comprises a radially constraining profile.

Example 127

The apparatus of any one or more of the preceding Examples, wherein the second external contact surface comprises a radially constraining profile complementary to the radially constraining profile of the first external contact surface.

Example 128

The apparatus of any one or more of the preceding Examples, wherein the radially constraining profile of the first external contact surface and the complementary radially constraining profile of the second external contact surface are configured to nest with each other while the loop is in the contracted configuration.

Example 129

The apparatus of any one or more of the preceding Examples, wherein the radially constraining profile of the first external contact surface and the complementary radially constraining profile of the second external contact surface are each curved profiles.

Example 130

The apparatus of any one or more of the preceding Examples, wherein each curved profile comprises an undulating configuration.

Example 131

The apparatus of any one or more of the preceding Examples, wherein the first bead comprises a first inner diameter surface associated with an inner diameter of the loop.

Example 132

The apparatus of any one or more of the preceding Examples, wherein the first inner diameter surface comprises conical shaped perimeter.

Example 133

The apparatus of any one or more of the preceding Examples, wherein the conical shaped perimeter is concentric around an expansion and contraction axis of the loop.

Example 134

The apparatus of any one or more of the preceding Examples, wherein the first bead comprises a first outer diameter surface associated with an outer diameter of the loop, wherein the first outer diameter surface comprises a spherical shape.

Example 135

The apparatus of any one or more of the preceding Examples, wherein the first bead comprises a magnet, wherein the second bead is a non-magnetic bead.

Example 136

An apparatus comprising: (a) a plurality of beads comprising: (i) a first bead, wherein the first bead comprises a first housing and a first external contact surface, wherein the first external contact surface comprises a curved profile, and (ii) a second bead located adjacent to the first bead, wherein the second bead comprises a second housing and a second external contact surface; and (b) a linking assembly coupling the plurality of beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; wherein the second external contact surface comprises a curved profile configured to nest within the curved profile of the first external contact surface of the first bead while the loop is in the contracted configuration.

Example 137

The apparatus of any one or more of the preceding Examples, wherein the curved profile of the first bead includes a concave region and a convex region, the concave region of the first bead curved profile being associated with an inner diameter region of the loop, the convex region of the first bead curved profile being associated with an outer diameter region of the loop.

Example 138

The apparatus of any one or more of the preceding Examples, wherein the curved profile of the second bead includes a concave region and a convex region, the concave region of the second bead curved profile being associated with an outer diameter region of the loop, the convex region of the second bead curved profile being associated with an inner diameter region of the loop.

Example 139

The apparatus of any one or more of the preceding Examples, the first bead defining a first passageway extending along a first axis, a portion of the linking assembling being disposed in the first passageway, the first bead being asymmetric about the first axis; the second bead defining a second passageway extending along a second axis, a portion of the linking assembling being disposed in the second passageway, the second bead being asymmetric about the second axis.

Example 140

An apparatus comprising: (a) a plurality of beads comprising: (i) a first bead, wherein the first bead comprises a first undulating engagement surface, and (ii) a second bead located adjacent to the first bead, wherein the second bead comprises a second undulating engagement surface; and (b) a linking assembly coupling the plurality of beads together, wherein the linking assembly extends within the first through hole of the first bead and the second through hole of the second bead to thereby couple the first bead with the second bead; wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; wherein the second undulating surface of the second bead is configured to abut against the first undulating engagement surface of the first bead to thereby drive the first bead and the second bead into a predetermined orientation relative to each other as the loop transitions to the contracted configuration.

Example 141

An apparatus comprising: (a) a plurality of beads; (b) a linking assembly coupling the plurality of beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads, wherein the beads and the linking assembly are configured to define a maximum radius in the expanded state and a minimum radius in the contracted state; and (c) an integrated adjustment assembly integrated with the plurality of beads or the linking assembly, wherein the integrated adjustment assembly is operable to selectively adjust either the maximum radius or the minimum radius while remaining integrated with the plurality of beads or the linking assembly.

Example 142

The apparatus of any one or more of the preceding Examples, wherein the integrated adjustment assembly comprises an inflatable bladder associated with the linking assembly.

Example 143

The apparatus of any one or more of the preceding Examples, wherein the inflatable bladder is interposed between a first bead and a second bead of the plurality of beads.

Example 144

The apparatus of any one or more of the preceding Examples, wherein the inflatable bladder comprises an inflation port configured to transfer fluid to and from the inflatable bladder.

Example 145

The apparatus of any one or more of the preceding Examples, wherein the inflatable bladder is configured to adjust the minimum radius of the plurality of beads and the linking assembly.

Example 146

The apparatus of any one or more of the preceding Examples, wherein the integrated adjustment assembly is configured to be adjusted when the apparatus is initially implanted in a patient.

Example 147

The apparatus of any one or more of the preceding Examples, wherein the integrated adjustment assembly is configured to be adjusted after the apparatus is initially implanted in a patient.

Example 148

The apparatus of any one or more of the preceding Examples, wherein the integrated adjustment assembly is configured to be adjusted based on forces experienced by the apparatus after being implanted.

Example 149

The apparatus of any one or more of the preceding Examples, wherein the integrated adjustment assembly is configured to elastically adjust the maximum radius while remaining integrated with the plurality of beads or the linking assembly.

Example 150

The apparatus of any one or more of the preceding Examples, wherein the integrated adjustment assembly is configured to plastically adjust the maximum radius while remaining integrated with the plurality of beads or the linking assembly.

Example 151

The apparatus of any one or more of the preceding Examples, wherein the integrated adjustment assembly comprises a link coupling body associated with a first bead and a link of the linking assembly, wherein the link coupling body is configured to selectively extend relative to the first bead to thereby adjust either the maximum radius or the minimum radius while remaining integrated with the plurality of beads or the linking assembly.

Example 152

The apparatus of any one or more of the preceding Examples, wherein the link coupling body is coupled to the first bead via a threaded relationship.

Example 153

The apparatus of any one or more of the preceding Examples, wherein the integrated adjustment assembly comprises a plurality of spacers associated with a link of the linking assembly.

Example 154

The apparatus of any one or more of the preceding Examples, wherein the integrated adjustment assembly comprises a compressible material contained within a housing, wherein the housing is coupled to a first bead via a restrain plate link.

Example 155

The apparatus of any one or more of the preceding Examples, wherein the restrain plate link comprises a restrain plate configured to compress the compressible material to thereby adjust the minimum radius.

Example 156

An apparatus comprising: (a) a plurality of beads; (b) a linking assembly coupling the plurality of beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads, wherein the beads and the linking assembly are configured to define a maximum radius in the expanded state and a minimum radius in the contracted state; and (c) an adjustment assembly integrated with the plurality of beads and the linking assembly, wherein the adjustment assembly configured to selectively adjust either the maximum radius or the minimum radius after the apparatus has been implanted.

Example 157

The apparatus of any one or more of the preceding Examples, wherein the adjustment assembly comprises a body frictionally fit to a link of the linking assembly.

Example 158

The apparatus of any one or more of the preceding Examples, wherein the body is slidable along the link in response to a predetermined force, wherein the body is configured to resist sliding along the link in response to forces lower than the predetermined force.

Example 159

The apparatus of any one or more of the preceding Examples, wherein the linking assembly comprises an elongate woven member.

Example 160

An apparatus comprising: (a) a plurality of beads, wherein each bead in the plurality of beads houses at least one magnet; (b) a linking assembly coupling the plurality of beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads, wherein the beads and the linking assembly are configured to define a maximum radius in the expanded state and a minimum radius in the contracted state; and (c) an adjustment assembly attached to the linking assembly, wherein the adjustment assembly is configured to adjust either the maximum radius or the minimum radius after the apparatus is implanted in a patient, in response to forces exerted against the apparatus by an anatomical structure of the patient.

XI. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a plurality of beads, each bead comprising:
        (i) a housing comprising:
            (A) a first piece extending between a first end and a second end, wherein the first end defines a link receiving opening, wherein the second end comprises an annular weld location, and
            (B) a second piece, wherein the first piece and the second piece together define a magnet chamber,
        (ii) at least one magnet disposed within the magnet chamber, and
        (iii) a weld joining the first piece and the second piece together, the weld hermetically sealing the magnet chamber, the weld extending along a weld plane,
        the first piece of the housing further including a mounting feature integrated with an external surface of the first piece, wherein the mounting feature faces in a direction away from the weld, wherein the mounting feature is located closer to the first end compared to the second end, wherein the mounting feature is configured to mate with a fixture to constrain the first piece of the housing as the weld is formed; and
    (b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

2. The apparatus of claim 1, the first piece comprising a first annular rim, the second piece comprising a second annular rim engaged with the first annular rim, the weld comprising a circumferential weld located at the first annular rim and the second annular rim.

3. The apparatus of claim 1, the mounting feature comprising a plurality of recesses defined by an external surface of the first piece.

4. The apparatus of claim 3, wherein the fixture comprises a plurality of complementary projections configured to engage the plurality of recesses defined by the external surface of the first piece.

5. The apparatus of claim 3, wherein the external surface extends along a plane that is parallel to the weld plane.

6. The apparatus of claim 1, wherein the mounting feature is configured to rotationally constrain the first piece relative to the fixture as the weld is formed.

7. The apparatus of claim 1, wherein the fixture comprises a complementary surface at least partially defining a housing recess configured to engage an external surface of the first piece adjacent to the mounting feature.

8. The apparatus of claim 1, wherein the second piece further comprises a second mounting feature integrated with a surface of the second piece, wherein the second mounting feature is configured to mate with a second fixture to constrain the second piece of the housing as the weld is formed.

9. The apparatus of claim 8, wherein the second mounting feature is configured to rotationally constrain the second piece of the housing as the weld is formed.

10. The apparatus of claim 1, the mounting feature comprising at least one projection extending outwardly from the surface of the first piece.

11. The apparatus of claim 10, the at least one projection comprising a ledge.

12. The apparatus of claim 1, the mounting feature comprising at least one dimple formed in the surface of the first piece.

13. The apparatus of claim 1, wherein the linking assembly comprises plurality of links joining the beads together, wherein portions of the links are slidably disposed in corresponding beads of the plurality of beads such that the beads are slidable along the links as the loop moves between the contracted configuration and the expanded configuration.

14. The apparatus of claim 1, wherein each bead further defines a passageway passing through the first piece and the second piece.

15. The apparatus of claim 14, the at least one magnet encircling the passageway.

16. An apparatus comprising:
(a) a plurality of beads, each bead comprising:
  (i) a housing comprising:
    (A) a first piece comprising a first end and a second end, wherein the first end defines a link receiving opening, wherein the second end comprises a first annular rim, and
    (B) a second piece comprising a second annular rim configured to engage the first annular rim, wherein the first piece and the second piece together define a magnet chamber,
  (ii) at least one magnet disposed within the magnet chamber, and
  (iii) a circumferential weld joining the first piece and the second piece together, the circumferential weld hermetically sealing the magnet chamber, the weld extending along a weld plane,
(b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads; and
(c) a mounting plate interface assembly integrally formed with an external surface of the first piece of the housing facing away from the circumferential weld, wherein the mounting plate interface assembly is located closer to the first end compared to the second end, wherein the mounting plate interface assembly is configured to configured to mate with a mounting plate to constrain the first piece of the housing as the weld is formed, the mounting plate interface being parallel with the weld plane.

17. An apparatus comprising:
(a) a plurality of beads, each bead comprising:
  (i) a housing comprising:
    (A) a first piece extending between a first end and a second end, the first end defining a link receiving opening, the second end comprising an annular weld location, and
    (B) a second piece, wherein the first piece and the second piece together define a magnet chamber,
  (ii) at least one magnet disposed within the magnet chamber, and
  (iii) a weld joining the first piece and the second piece together, the weld hermetically sealing the magnet chamber, the weld extending along a weld plane,
  the first piece of the housing further including a mounting feature integrated with a surface of the first piece, wherein the mounting feature is located closer to the first end compared to the second end, wherein the mounting feature is configured to mate with a fixture to constrain the first piece of the housing as the weld is formed; and
(b) a linking assembly joining the beads together, wherein the beads and the linking assembly are configured to be arranged in an annular arrangement, wherein the annular arrangement is sized and configured to form a loop around an anatomical structure in a patient, wherein the loop is configured to move between a contracted configuration and an expanded configuration, wherein the loop in the contracted configuration is configured to prevent fluid flow through the anatomical structure, wherein the loop in the expanded configuration is configured to permit fluid flow through the anatomical structure, wherein the loop is magnetically biased toward the contracted configuration by a magnetic bias of the beads.

* * * * *